(12) United States Patent
Cooper et al.

(10) Patent No.: US 11,548,945 B2
(45) Date of Patent: *Jan. 10, 2023

(54) T-CELL RECEPTOR (TCR)-BINDING ANTIBODIES AND USES THEREOF

(71) Applicant: BOARD OF REGENTS, THE UNIVERSITY OF TEXAS SYSTEM, Austin, TX (US)

(72) Inventors: Laurence J. N. Cooper, Houston, TX (US); Bipulendu Jena, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 208 days.

This patent is subject to a terminal disclaimer.

(21) Appl. No.: 16/834,562

(22) Filed: Mar. 30, 2020

(65) Prior Publication Data

US 2020/0299386 A1  Sep. 24, 2020

Related U.S. Application Data

(63) Continuation of application No. 15/759,148, filed as application No. PCT/US2016/051847 on Sep. 15, 2016, now Pat. No. 10,633,445.

(60) Provisional application No. 62/218,990, filed on Sep. 15, 2015.

(51) Int. Cl.
| | |
|---|---|
| C07K 16/28 | (2006.01) |
| A61K 39/395 | (2006.01) |
| C07K 14/725 | (2006.01) |
| C12N 5/0783 | (2010.01) |

(52) U.S. Cl.
CPC .... *C07K 16/2809* (2013.01); *A61K 39/39558* (2013.01); *C07K 14/7051* (2013.01); *C07K 16/2833* (2013.01); *C07K 16/2896* (2013.01); *C12N 5/0636* (2013.01); *C07K 2317/34* (2013.01); *C07K 2317/56* (2013.01); *C07K 2317/565* (2013.01); *C07K 2317/622* (2013.01)

(58) Field of Classification Search
None
See application file for complete search history.

(56) References Cited

U.S. PATENT DOCUMENTS

| | | |
|---|---|---|
| 9,629,877 B2 | 4/2017 | Cooper et al. |
| 9,701,758 B2 | 7/2017 | Cooper et al. |
| 10,633,445 B2 | 9/2020 | Cooper et al. |
| 2006/0052585 A1 | 3/2006 | Grawunder et al. |
| 2014/0147447 A1 | 5/2014 | Klimatcheva et al. |
| 2014/0349402 A1 | 11/2014 | Cooper et al. |
| 2016/0096902 A1 | 4/2016 | Cooper et al. |
| 2016/0158285 A1 | 6/2016 | Cooper et al. |
| 2016/0256487 A1 | 9/2016 | Cooper et al. |
| 2017/0044500 A1 | 2/2017 | Cooper et al. |
| 2017/0158749 A1 | 6/2017 | Cooper et al. |
| 2017/0183407 A1 | 6/2017 | Cooper et al. |
| 2017/0333480 A1 | 11/2017 | Cooper et al. |
| 2017/0334968 A1 | 11/2017 | Cooper et al. |
| 2018/0051265 A1 | 2/2018 | Cooper et al. |
| 2018/0298349 A1 | 10/2018 | Rushworth et al. |

FOREIGN PATENT DOCUMENTS

| | | |
|---|---|---|
| CN | 1633448 | 6/2005 |
| CN | 103347896 | 10/2013 |
| WO | WO 90/06758 | 6/1990 |
| WO | WO 2011/150454 | 12/2011 |
| WO | WO 2013/074916 | 5/2013 |
| WO | WO 2014/078475 | 5/2014 |
| WO | WO 2014/140368 | 9/2014 |
| WO | WO 2014/186469 | 11/2014 |
| WO | WO 2014/190273 | 11/2014 |
| WO | WO 2015/061694 | 4/2015 |
| WO | WO 2015/123642 | 8/2015 |
| WO | WO 2015/164594 | 10/2015 |
| WO | WO 2015/164740 | 10/2015 |
| WO | WO 2016/073629 | 5/2016 |
| WO | WO 2016/073755 | 5/2016 |
| WO | WO 2016/138091 | 9/2016 |
| WO | WO 2016/145146 | 9/2016 |
| WO | WO 2017/075147 | 5/2017 |

OTHER PUBLICATIONS

Kunik, Vered, Bjoern Peters, and Yanay Ofran. "Structural consensus among antibodies defines the antigen binding site." *PLoS Comput Biol* 8.2 (2012): e1002388.
Office communication issued in corresponding European Application No. 16 770 634.0, dated Sep. 30, 2020.
Office communication issued in corresponding Japanese Application No. 2018-513633, dated Aug. 24, 2020. English Translation.
De Pascalis, Roberto, et al. "Grafting of "abbreviated" complementarity-determining regions containing specificity-determining residues essential for ligand contact to engineer a less immunogenic humanized monoclonal antibody." *The Journal of Immunology* 169.6 (2002): 3076-3084.
Goel, Manisha, et al. "Plasticity within the antigen-combining site may manifest as molecular mimicry in the humoral immune response." *The Journal of Immunology* 173.12 (2004): 7358-7367.
Khan, Tarique, and Dinakar M. Salunke. "Adjustable locks and flexible keys: plasticity of epitope-paratope interactions in germline antibodies." *The Journal of Immunology* 192.11 (2014): 5398-5405.
MacCallum, Robert M., Andrew CR Martin, and Janet M. Thornton. "Antibody-antigen interactions: contact analysis and binding site topography." *Journal of Molecular Biology* 262.5 (1996): 732-745.
Mariuzza, R. A., S. E. V. Phillips. and R. J. Poljak. "The structural basis of antigen-antibody recognition." *Annual Review of Biophysics and Biophysical Chemistry* 16.1 (1987): 139-159.

(Continued)

*Primary Examiner* — Nora M Rooney
(74) *Attorney, Agent, or Firm* — Parker Highlander PLLC

(57) ABSTRACT

Antibodies and antigen binding fragments thereof are provided that bind to T-cell receptors (e.g., TCRα), essentially independent of T-cell epitope specificity. Methods for manipulation of T-cells and methods of treatment using such antibodies are likewise provided.

14 Claims, 41 Drawing Sheets

Specification includes a Sequence Listing.

(56) References Cited

OTHER PUBLICATIONS

PCT International Preliminary Report on Patentability issued in International Application No. PCT/US2016/051847, dated Mar. 29, 2018.

PCT International Search Report and Written Opinion issued in International Application No. PCT/US2016/051847, dated Jan. 31, 2017.

Poosarla, Venkata Giridhar, et al. "Computational de novo design of antibodies binding to a peptide with high affinity." *Biotechnology and Bioengineering* 114.6 (2017): 1331-1342.

He et al., "Inhibitory effects of HIV-1 gp41 fusion peptide on CD3 antibody activated regulatory T cells", *J. Cell. Mol. Immunol.*, 28(11):1121-1125, 2012. English abstract.

Office Action issued in corresponding Chinese Application No. 201680066388.2, dated Mar. 8, 2021. English translation appended.

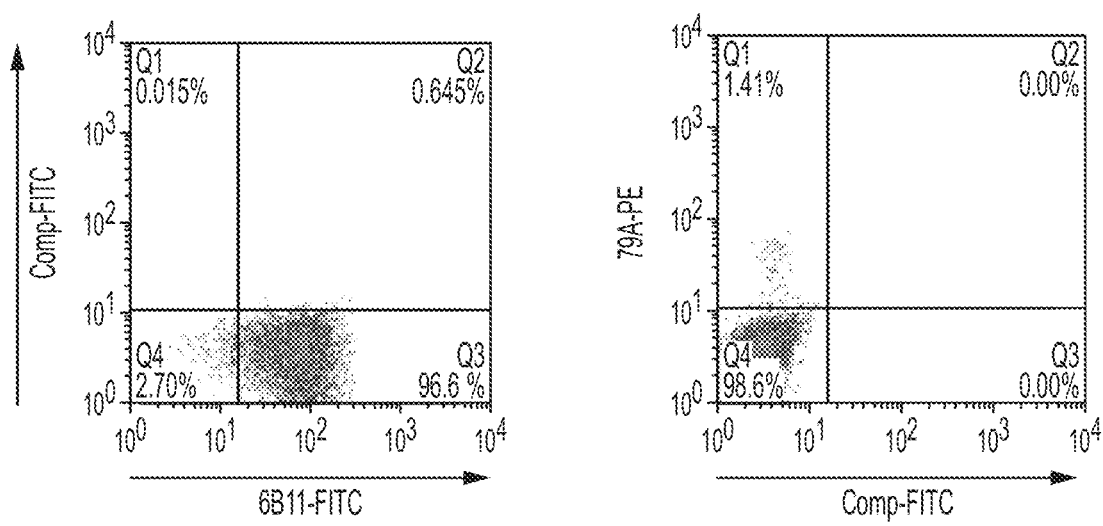
FIG. 1E(ii)

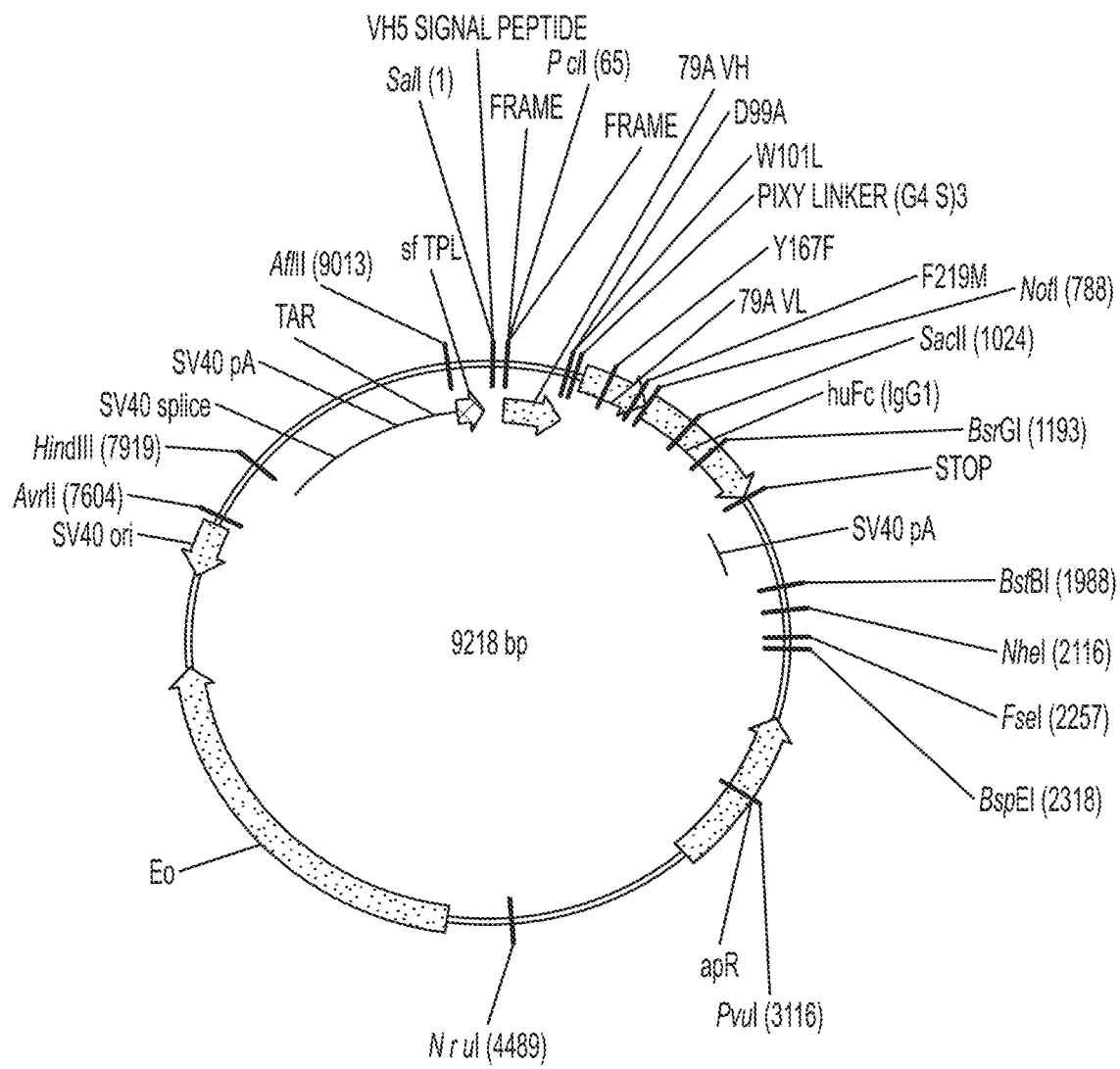
FIG. 5A(ii)

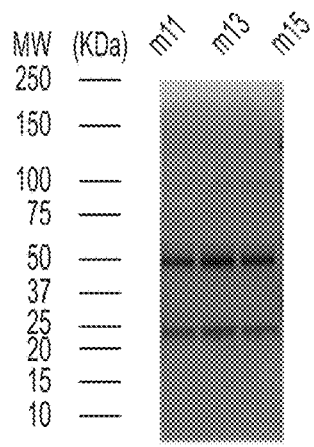
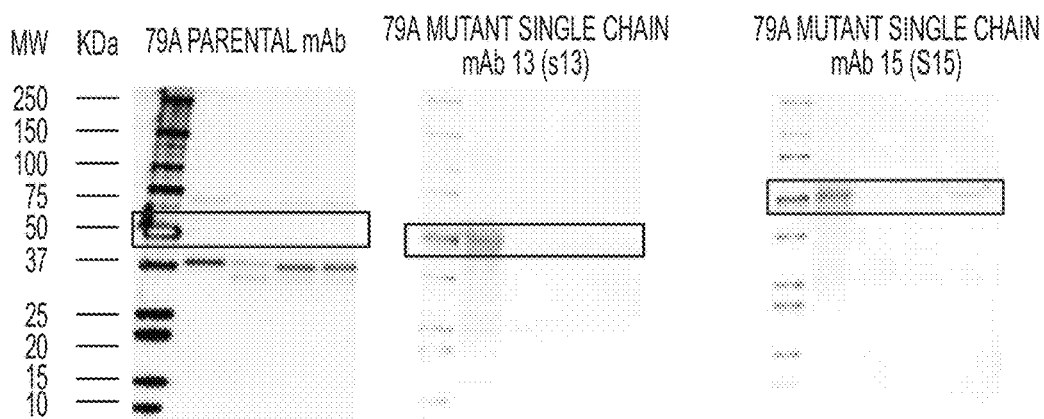
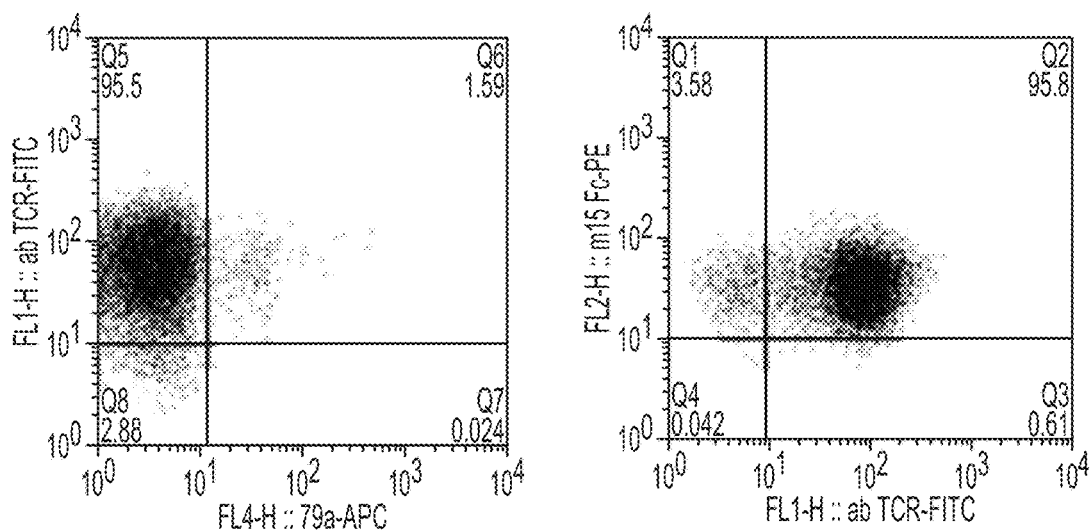
FIGS. 6A-C

|  | OKT3 T CELLS | PBMC_T CELLS | CS1S15 |
|---|---|---|---|
| OKT3 T CELLS |  | $r^2=0.055$<br>$O=0.172$ | $r^2=0.040$<br>$O=0.224$ |
| PBMC_T CELLS | $r^2=0.055$<br>$O=0.172$ |  | $r^2=0.043$<br>$O=0.472$ |
| CS1S15 | $r^2=0.040$<br>$O=0.224$ | $r^2=0.043$<br>$O=0.472$ |  |

FIG. 8D

T-CELL RECEPTOR (TCR)-BINDING ANTIBODIES AND USES THEREOF

This application is a continuation of U.S. application Ser. No. 15/759,148, filed Mar. 9, 2018, as a national phase application under 35 U.S.C. § 371 of International Application No. PCT/US2016/051847, filed Sep. 15, 2016, which claims the benefit of U.S. Provisional Application No. 62/218,990, filed on Sep. 15, 2015, the entirety of each of which is incorporated herein by reference.

INCORPORATION OF SEQUENCE LISTING

The instant application contains a Sequence Listing which has been submitted electronically in ASCII format and is hereby incorporated by reference in its entirety. Said ASCII copy, created on Mar. 30, 2020, is named UTSCP1281USC1_ST25.txt and is 25 kb in size.

BACKGROUND OF THE INVENTION

Field of the Invention

The present invention relates generally to the field of molecular biology and immunology. More particularly, it concerns monoclonal recombinant antibodies that bind αβ-TCR (T-cell receptors) and the use of such antibodies in the manipulation of αβ-TCR$^+$ T-cells inside and outside the body.

Description of Related Art

T-cell based therapies are currently being explored for treatment of a wide range of diseases. However, one of the major hurdles in any T-cell-based therapy is efficient selection (isolation) and numeric expansion of T-cells for use in the therapy. Furthermore, T cells can be altered inside the body for activation and immune suppression. Thus, there remains a need for new methods and compositions that can be used for manipulation of T-cells in vivo and ex vivo.

SUMMARY OF THE INVENTION

The invention provides an isolated antibody or antigen-binding fragment thereof that specifically binds to an epitope of T-cell receptor alpha (TCRα) polypeptide comprising sequence GSTLRG (SEQ ID NO:1).

In embodiments, the antibody or antigen binding fragment thereof specifically binds to an epitope of T-cell receptor alpha (TCRα) polypeptide comprising the sequence GSTLRG (SEQ ID NO:1) with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{10}$ M, $10^{-10}$ M, $5 \times 10^{-11}$ M, $10^{-11}$ M, $5 \times 10^{-12}$ M, $10^{-12}$ M, $8.4 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M. In embodiments, the $K_D$ is about $5 \times 10^{-9}$ M to about $6 \times 10^{-9}$ M. In further embodiments, the $K_D$ is about $1 \times 10^{-9}$ M to about $2 \times 10^{-9}$ M.

In further embodiments, the invention relates to an antibody or antigen-binding fragment thereof that specifically binds to TCRα polypeptide, comprising (a) HCDR1 at least 80%, 85%, 90% or 95% identical to SEQ ID NO: 2; (b) HCDR2 at least 80%, 85%, 90% or 95% identical to SEQ ID NO: 3; (c) HCDR3 identical to CDYW (SEQ ID NO:21); CAYW (SEQ ID NO:23); or CAYL (SEQ ID NO:22); (d) LCDR1 at least 80%, 85%, 90% or 95% identical to SEQ ID NO: 4 or SEQ ID NO: 9; (e) LCDR2 at least 80%, 85%, 90% or 95% identical to SEQ ID NO: 5; and (f) LCDR3 at least 80%, 85%, 90% or 95% identical to SEQ ID NO: 6 or SEQ ID NO: 10.

The invention further provides an antibody or antigen-binding fragment thereof that specifically binds to TCRα polypeptide comprising (a) HCDR1 at least 80%, 85%, 90% or 95% identical to $V_H$ CDR1 of 79A-15 SEQ ID NO: 2; (b) HCDR2 at least 80%, 85%, 90% or 95% identical to $V_H$ CDR2 of 79A-15 SEQ ID NO: 3; (c) HCDR3 at least 80%, 85%, 90% or 95% identical to $V_H$ CDR3 of 79A-15 (SEQ ID NO:22); (d) LCDR1 at least 80%, 85%, 90% or 95% identical to $V_L$ CDR1 of 79A-15 SEQ ID NO: 9; (e) LCDR2 at least 80%, 85%, 90% or 95% identical to $V_L$ CDR2 of 79A-15 SEQ ID NO: 5; and (f) LCDR3 at least 80%, 85%, 90% or 95% identical to $V_L$ CDR3 of 79A-15 SEQ ID NO: 10.

In further aspects, the invention provides an isolated antibody or antigen binding fragment thereof that specifically binds to TCRα polypeptide, comprising (a) HCDR1 at least 80%, 85%, 90% or 95% identical to $V_H$ CDR1 of 79A-13 KASGYTFTDYYMNWV (SEQ ID NO: 2); (b) HCDR2 at least 80%, 85%, 90% or 95% identical to $V_H$ CDR2 of 79A-13 WIGEINPNN (SEQ ID NO: 3); (c) HCDR3 at least 80%, 85%, 90% or 95% identical to $V_H$ CDR3 of 79A-13 CAYL (SEQ ID NO:22); (d) LCDR1 at least 80%, 85%, 90% or 95% identical to $V_L$ CDR1 of 79A-13 NTYLEWY (SEQ ID NO: 4); (e) LCDR2 at least 80%, 85%, 90% or 95% identical to $V_L$ CDR2 of 79A-13 KLLIYKVSNRFS (SEQ ID NO: 5); and (f) LCDR3 at least 80%, 85%, 90% or 95% identical to $V_L$ CDR3 of 79A-13 MQGSHVPW (SEQ ID NO: 10).

In embodiments, the invention further relates to an antibody or antigen-binding fragment thereof that specifically binds to TCRα polypeptide, comprising (a) HCDR1 at least 80%, 85%, 90% or 95% identical to $V_H$ CDR1 of 79A-11 KASGYTFTDYYMNWV (SEQ ID NO: 2); (b) HCDR2 at least 80%, 85%, 90% or 95% identical to $V_H$ CDR2 of 79A-11 WIGEINPNN (SEQ ID NO: 3); (c) HCDR3 at least 80%, 85%, 90% or 95% identical to $V_H$ CDR3 of 79A-11 CAYW (SEQ ID NO:23); (d) LCDR1 at least 80%, 85%, 90% or 95% identical to $V_L$ CDR1 of 79A-11 NTYLEWF (SEQ ID NO: 9); (e) LCDR2 at least 80%, 85%, 90% or 95% identical to $V_L$ CDR2 of 79A-11 KLLIYKVSNRFS (SEQ ID NO: 5); and (f) LCDR3 at least 80%, 85%, 90% or 95% identical to $V_L$ CDR3 of 79A-11 MQGSHVPW (SEQ ID NO: 10).

The invention also provides an isolated antibody or antigen binding fragment thereof that specifically binds to TCRα polypeptide, comprising (a) HCDR1 at least 80%, 85%, 90% or 95% identical to $V_H$ CDR1 of 79A KASGYTFTDYYMNWV (SEQ ID NO: 2); (b) HCDR2 at least 80%, 85%, 90% or 95% identical to $V_H$ CDR2 of 79A WIGEINPNN (SEQ ID NO: 3); (c) HCDR3 at least 80%, 85%, 90% or 95% identical to $V_H$ CDR3 of 79A CDYW (SEQ ID NO:21); (d) LCDR1 at least 80%, 85%, 90% or 95% identical to $V_L$ CDR1 of 79A NTYLEWY (SEQ ID NO: 4); (e) LCDR2 at least 80%, 85%, 90% or 95% identical to $V_L$ CDR2 of 79A KLLIYKVSNRFS (SEQ ID NO: 5); and (f) LCDR3 at least 80%, 85%, 90% or 95% identical to $V_L$ CDR3 of 79A FQGSHVPW (SEQ ID NO: 6).

In embodiments, the invention provides an isolated antibody or antigen binding fragment thereof that specifically binds to TCRα polypeptide, comprising (a) HCDR1 at least 80%, 85%, 90% or 95% identical to KASGYTFTGYYMNWV (SEQ ID NO:15); (b) HCDR2 at least 80%, 85%, 90% or 95% identical to WIGGINPNN (SEQ ID NO:16); (c) HCDR3 identical to CRYW (SEQ ID NO:17); (d) LCDR1 at least 80%, 85%, 90% or 95% identical to QSIVHGGGNTY (SEQ ID NO:18); (e) LCDR2 at least 80%, 85%, 90% or 95% identical to KLLIYKVSNRFS (SEQ ID NO: 5); and (f) LCDR3 at least 80%, 85%, 90% or 95% identical to FQGSHVPW (SEQ ID NO: 6).

In additional aspects, the invention further provides an isolated polynucleotide comprising a nucleic acid encoding an antibody or antigen binding fragment thereof that specifically binds to a T-cell Receptor α chain (TCRα), said antibody binding to an epitope of TCRα polypeptide comprising the sequence GSTLRG (SEQ ID NO: 1).

In further embodiments, the invention provides a vector comprising the polynucleotides encoding an antibody or antigen binding fragment thereof that specifically binds to a T-cell Receptor α chain (TCRα), said antibody binding to an epitope of TCRα polypeptide comprising the sequence GSTLRG (SEQ ID NO: 1).

In still further embodiments, the invention provides a method of manufacturing an antibody or antigen binding fragment thereof comprising: (a) expressing one or more polynucleotide molecule(s) encoding a $V_L$ and $V_H$ chain of an antibody in a cell; and (b) purifying the antibody from the cell, wherein the antibody specifically binds to a T-cell Receptor α chain (TCRα).

The invention further provides a method for selecting a cell comprising a T-cell Receptor α chain (TCRα) comprising: (a) contacting the cell with an antibody or antigen fragment thereof that binds to a TCRα chain, wherein the antibody or fragment binds to T-cells having a plurality of T-cell epitope specificities; and (b) selecting a cell comprising the TCR α chain based on binding of the antibody or fragment.

In additional embodiments, the invention provides a method for expanding and/or activating T-cells comprising contacting the T-cells with artificial antigen presenting cells (aAPCs) in the presence of an antibody or antigen binding fragment thereof that binds to an epitope of a T-cell Receptor (TCR), wherein said epitope is a polypeptide comprising sequence GSTLRG (SEQ ID NO:1).

In certain aspects, the invention provides a method of treating an autoimmune disease or a T cell leukemia in an animal in need of treatment, comprising administering to said animal a host cell comprising a chimeric antigen receptor targeting TCRα polypeptide comprising sequence GSTLRG (SEQ ID NO:1).

In further embodiments, the invention provides a host cell comprising one or more polynucleotide molecules encoding an antibody or antigen binding fragment thereof that binds to a TCRα chain comprising GSTLRG (SEQ ID NO:1), wherein the antibody or antigen binding fragment thereof selectively binds to T-cells having a plurality of T-cell epitope specificities.

A further embodiment provides a kit comprising an antibody of the present embodiments or a host cell comprising one or more polynucleotide molecule(s) encoding an antibody that binds to a T-Cell Receptor (TCR) wherein the antibody binds to T-cells having a plurality of T-cell epitope specificities and at least a first agent for increasing proliferation of mammalian T-cells. In certain aspects, kit additionally comprises an APC.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 8A-8D. A) TCRVβ repertoire of healthy donor PBMC derived T cells compared with activated T cells expanded on aAPC by S15 or OKT3-CD3ε stimulation shows generation of population of T cells with heterogeneous T-cell repertoire. No unexpected skewing of repertoire in activated in vitro expanded T cells are noticed. B) TCRVβ repertoire of activated T cells grown by either S15 stimulation (CS1S15) of by OKT3 T cells. The repertoire represents a polyclonal T cell population without any specific growth of clonotypes. C) Next generation deep sequence survey of T cell clone frequency and distribution after ex vivo propagation. Commonality in clonotypes are seen to be aligned with PBMC better after S15 mediated activation as compared to OKT3 stimulation D) Table shows Pearson coefficient values ($r^2$) representing clonal frequency of T cells generated after activation. T cell clone frequencies are compared between T cells stimulated with (Parental K562/ACT), with (K562-S15-Co-stims) and (K562-OKT3-Co-stims). Sample overlap as compared to PBMC shows $r^2$ values 0.043 and o=0.472 for S15 T cells and $r^2$=0.055 and sample overlap o=0.172 for OKT3-PBMC. Clonal overlap is superior for S15 activated T cells.

DESCRIPTION OF ILLUSTRATIVE EMBODIMENTS

I. Definitions

Figure 1A:
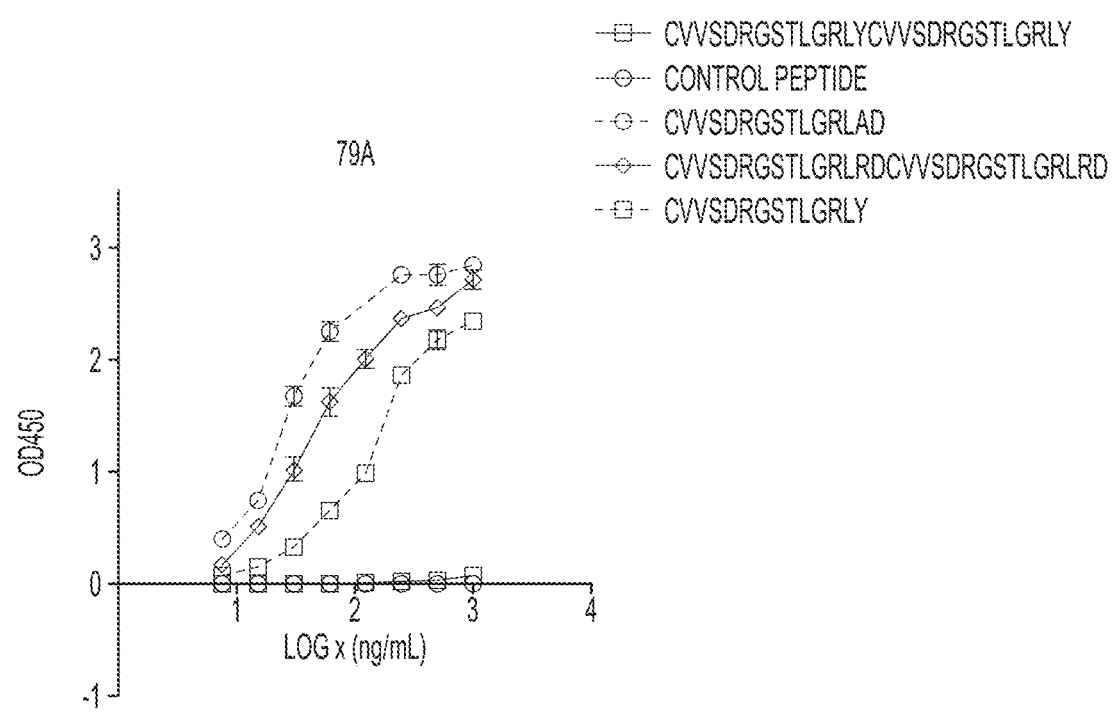
FIGS. 1A-1E(i), 1E(ii). A) Binding specificity of monoclonal antibody (Clone 79A). ELISA performed on solid phase coated with linear TCR-invariant chain specific synthetic peptides. Antibody dose curve were run with a concentration range from 1000 ng/mL to 7.5 ng/mL. Controls include non-specific peptides, secondary antibody control and buffer control in the assay. Assay plate was read at OD450 by Victor™ plate reader. Samples were run in duplicate. B) Ala-Scan library confirmed linear epitope specificity of mAb 79A on lyophilized peptides (Mimotope™ Ala-scan peptide library) coated onto solid phase ELISA. Graph shows highest binding intensity of 79A mAb upon substitution with selected AA with Alanine. C) Moderate binding of 79A to specific peptides as shown in figure substituted with alanine. D) GSTLGR (SEQ ID NO:1) represents junction of TCR Va24 and Ja18 where 79A binding focuses as substitution of these AA by alanine completely abrogates binding. E(i) and E(ii)) 79A lacks conformational fit to TCR-CDR3 invariant chain. Flow cytometry assay shows that 79A fails to bind either purified iNKT cell (in image) or regular αβ⁺-T cells (shown later) where as iNKT-specific mAb 6B11 detects conformational epitopes on iNKT cells.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore preferably below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides that do not possess a defined three-dimensional structure, but rather can adopt a large number of different conformations, are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Synthetic recombinant polypeptides and/or proteins expressed in host cells are considered isolated for purpose of the invention, as are native or recombinant polypeptides that have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative," and "analog" when referring to anti-TCR antibodies or antibody polypeptides of the present invention include any polypeptides that retain at least some of the antigen-binding properties of the corresponding antibody or antibody polypeptide of the invention. Fragments of polypeptides of the present invention include proteolytic fragments, as well as deletion fragments, in addition to specific antibody fragments discussed elsewhere herein. Variants of anti-TCR antibodies and antibody polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions, or additions. Variant polypeptides may also be referred to herein as "polypeptide analogs," As used herein a "derivative" of an anti-TCR antibody or antibody polypeptide refers to a subject polypeptide having one or more residues chemically derivatized by reaction of a functional side group. Also included as "derivatives" are those peptides that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. Derivatives of anti-TCR antibodies and antibody polypeptides of the present invention, may include polypeptides that have been altered so as to exhibit additional features not found on the reference antibody or antibody polypeptide of the invention.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, that has been removed from its native environment. For example, a recombinant polynucleotide encoding an anti-TCR binding molecule, e.g., an antibody or antigen binding fragment thereof, contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

As used herein, a "coding region" is a portion of nucleic acid that consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding an anti-TCR antibody or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid that encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit .beta.-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to, ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions that encode secretory or signal peptides, which direct the secretion of a polypeptide encoded by a polynucleotide of the present invention. According to the signal hypothesis, proteins secreted by mammalian cells have a signal peptide or secretory leader sequence that is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucoronidase.

As used herein, the term "TCR" refers to "T cell receptor." A T cell receptor is a molecule on the surface of T lymphocytes ("T cells"). In embodiments, the receptor is an αβ-TCR receptor, meaning that the T cell receptor comprises an alpha (α) and beta (β) chain, which is typically expressed as part of a complex with CD3 chain molecules. Thus, an "αβ-TCR+ T cell" is a T lymphocyte that contains a T cell receptor on its surface that comprises α and β chains. Both the α and β chains are highly variable, although the T-cell receptor α chain contains a constant (preserved region), i.e., the Va24-Ja18 junction (amino acid sequence GSTLGR (SEQ ID NO:1)).

A "binding molecule" or "antigen binding molecule" of the present invention refers in its broadest sense to a molecule that specifically binds an antigenic determinant. In one embodiment, the binding molecule specifically binds to TCR, e.g., a T-cell receptor, e.g., a T-cell receptor α chain. In embodiments, the binding molecule specifically binds to the Va24-Ja18 junction (amino acid sequence GSTLGR (SEQ ID NO:1)) of the T-cell receptor α-chain. In another embodiment, a binding molecule of the invention is an antibody or an antigen binding fragment thereof that includes point mutations to increase affinity. In another embodiment, a binding molecule of the invention comprises at least one heavy or light chain CDR of an antibody molecule. In another embodiment, a binding molecule of the invention comprises at least two CDRs from one or more antibody molecules. In another embodiment, a binding molecule of the invention comprises at least three CDRs from one or more antibody molecules. In another embodiment, a binding molecule of the invention comprises at least four CDRs from one or more antibody molecules. In another embodiment, a binding molecule of the invention comprises at least five CDRs from one or more antibody molecules. In another embodiment, a binding molecule of the invention comprises at least six CDRs from one or more antibody molecules.

The present invention is directed to certain anti-TCR antibodies, or antigen-binding fragments, variants, or derivatives thereof. Unless specifically referring to a full length antibodies such as naturally occurring antibodies, the term "anti-TCR antibodies" encompasses antigen-binding fragments, variants, analogs, or derivatives of such antibodies, e.g., naturally occurring antibody or immunoglobulin molecules or engineered antibody molecules or fragments that bind antigen in a manner similar to antibody molecules.

As used herein, "human" or "fully human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example, in U.S. Pat. No. 5,939,598 by Kucherlapati et "Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s).

"Human" or "fully human" antibodies also include "human" or "fully human" antibodies, as described above, that comprise, consist essentially of, or consist of, variants (including derivatives) of antibody molecules (e.g., the VH regions and/or VL regions) described herein, which antibodies or fragments thereof immunospecifically bind to a TCR or fragment or variant thereof. Standard techniques known to those of skill in the art can be used to introduce mutations in the nucleotide sequence encoding a human anti-TCR antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, HCDR1. HCDR2, HCDR3, VL region, LCDR1, LCDR2, or LCDR3.

In certain embodiments, the amino acid substitutions are conservative amino acid substitution, discussed further below. Alternatively, mutations can be introduced randomly along all or part of the coding sequence, such as by saturation mutagenesis, and the resultant mutants can be screened for biological activity to identify mutants that retain activity (e.g., the ability to bind a TCR polypeptide, e.g., human, murine, or both human and murine TCR). Such variants (or derivatives thereof) of "human" or "fully human" antibodies can also be referred to as human or fully human antibodies that are "optimized" or "optimized for antigen binding" and include antibodies that have improved affinity to antigen.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al. (1988) Antibodies: A Laboratory Manual (2nd ed.; Cold Spring Harbor Laboratory Press).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, with some subclasses among them (e.g., gamma1-gamma4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention. The following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL or VK) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs) within these variable domains, of an antibody combine to form the variable region that defines a three-dimensional antigen binding site. This quaternary antibody structure forms the antigen binding site present at the end of each arm of the Y. More specifically, the antigen binding site is defined by three CDRs on each of the VH and VL chains. As used herein, the terms HCDR1, HCDR2, HCDR3 refer to VH CDR1, VH CDR2, VH CDR3, respectively. Likewise, as used herein, the terms LCDR1, LCDR2, LCDR3, refer to VL CDR1, VL CDR2, and VL CDR3, respectively. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three-dimensional configuration in an aqueous environment. The remainder of the amino acids in the antigen binding domains, referred to as "framework" regions, show less inter-molecular variability. The framework regions largely adopt a sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see below).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest," by Chothia and Lesk, J. Mol. Biol. 196:901-917 (1987), and updated recently by Kunik et al., Nucl. Acids Res. 40:W521-W524 (2012), which are incorporated herein by reference, where the definitions include overlapping or subsets of amino acid residues when compared against each other. Nevertheless, application of any definition to refer to a CDR of an antibody or variants thereof is intended to be within the scope of the term as defined and used herein. The appropriate amino acid residues that encompass the CDRs as defined by each of the above cited references are set forth below in Table 1 as a comparison. The exact residue numbers that encompass a particular CDR will vary depending on the sequence and size of the CDR. Those skilled in the art can routinely determine which residues comprise a particular CDR given the variable region amino acid sequence of the antibody.

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest."

Kunik et al., Nucl. Acids Res. 40:W521-W524 (2012) disclosed an online tool, Paratome, for systematic identification of antigen-binding regions in antibodies based on sequence or structure. Usually the Paratome-based analysis matches with Kabat numbering, but may also include residues adjacent to conventional CDRs. Unless otherwise specified, references to the numbering of specific amino acid residue positions in an anti-TCR antibody CDRs or antigen-binding fragment, variant, or derivative thereof of the present invention are according to the numbering system based on Paratome identification.

Antibodies or antigen-binding fragments, variants, or derivatives thereof of the invention include, but are not limited to, polyclonal, monoclonal, multispecific, human, humanized, primatized, or chimeric antibodies, single-chain antibodies, epitope-binding fragments, e.g., Fab, Fab' and F(ab')$_2$, Fd, Fvs, single-chain Fvs (scFv), disulfide-linked Fvs (sdFv), fragments comprising either a VL or VH domain, fragments produced by a Fab expression library, and anti-idiotypic (anti-Id) antibodies (including, e.g., anti-Id antibodies to anti-TCR antibodies disclosed herein). ScFv molecules are known in the art and are described, e.g., in U.S. Pat. No. 5,892,019. Immunoglobulin or antibody molecules of the invention can be of any type IgG, IgE, IgD, IgA, and IgY), class (e.g., IgG1, IgG2, IgG3, IgG4, IgA1, and IgA2, etc.), or subclass of immunoglobulin molecule.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain anti-TCR antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody.

The heavy chain portions of a binding molecule for use in the diagnostic and treatment methods disclosed herein may be derived from different immunoglobulin molecules. For example, a heavy chain portion of a polypeptide may comprise a C.sub.H1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain, e.g., a kappa or lambda light chain. Preferably, the light chain portion comprises at least one of a VL or CL domain.

Anti-TCR antibodies, or antigen-binding fragments, variants, or derivatives thereof disclosed herein may be described or specified in terms of the epitope(s) or portion(s) of an antigen, e.g., a target polypeptide disclosed herein (e.g., TCR) that they recognize or specifically bind. The portion of a target polypeptide that specifically interacts with the antigen binding domain of an antibody is an "epitope," or an "antigenic determinant." A target polypeptide may comprise a single epitope, but typically comprises at least two epitopes, and can include any number of epitopes, depending on the size, conformation, and type of antigen. Furthermore, it should be noted that an "epitope" on a target polypeptide may be or may include non-polypeptide elements, e.g., an epitope may include a carbohydrate side chain.

The minimum size of a peptide or polypeptide epitope for an antibody, is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. A peptide or polypeptide epitope recognized by anti-TCR antibodies of the present invention may contain a sequence of at least 4, at least 5, at least 6, at least 7, more preferably at least 8, at least 9, at least 10, at least 15, at least 20, at least 25, or between about 15 to about 30 contiguous or non-contiguous amino acids of TCR.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to quality the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope. An antibody or antigen-binding fragment, variant, or derivative disclosed herein may be said to bind a target polypeptide disclosed herein (e.g., TCR, e.g., human, murine, or both human and murine TCR) or a fragment or variant thereof with an off rate (k(off)) of less than or equal to $5 \times 10^{-2}$ sec$^{-1}$, $10^{-3}$ sec$^{-1}$, $5 \times 10^{-3}$ sec$^{-1}$ or $10^{-3}$ sec$^{-1}$. More preferably, an antibody of the invention may be said to bind a target polypeptide disclosed herein (e.g., TCR, e.g., human, murine, or both human and murine TCR) or a fragment or variant thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$ or $10^{-7}$ sec$^{-1}$.

Anti-TCR antibodies or antigen binding fragments, variants or derivatives thereof of the invention may be "multi-specific," bispecific, trispecific, or of greater muitispecific-ity, meaning that it recognizes and binds to two or more different epitopes present on one or more different antigens (e.g., proteins) at the same time. Thus, whether an anti-TCR antibody is "monospecific" or "multispecific," e.g., "bispe-cific," refers to the number of different epitopes with which a binding polypeptide reacts. Multispecific antibodies may be specific for different epitopes of a target polypeptide described herein or may be specific for a target polypeptide as well as for a heterologous epitope, such as a heterologous polypeptide or solid support material.

As used herein the term "valency" refers to the number of potential binding domains, e.g., antigen binding domains present in a binding polypeptide or TCR binding molecule, e.g., an antibody or antigen binding fragment thereof. Each binding domain specifically binds one epitope. When a binding polypeptide or TCR binding molecule comprises more than one binding domain, each binding domain may specifically bind the same epitope, for an antibody with two binding domains, termed "bivalent monospecific," or to different epitopes, for an antibody with two binding domains, termed "bivalent bispecific." An antibody or anti-gen binding fragment thereof may also be bispecific and bivalent for each specificity (termed "bispecific tetravalent antibodies"). In another embodiment, tetravalent minibodies or domain deleted antibodies can be made.

Bispecific bivalent antibodies, and methods of making them, are described, for instance in U.S. Pat. Nos. 5,731,168; 5,807,706; 5,821,333; and U.S. Patent Appl. Publ. Nos. 2003/020734 and 2002/0155537, the disclosures of all of which are incorporated by reference herein. Bispecific tet-ravalent antibodies, and methods of making them are described, for instance, in WO 02/096948 and WO 00/14788, the disclosures of both of which are incorporated by reference herein. See generally, PCT publications WO 93/17715; WO 92/08802; WO 91/00360; WO 92/05793; Tutt et al., J. Immunol. 147:60-69 (1991); U.S. Pat. Nos. 4,471,893; 4,714,681; 4,925,648; 5,573,920; 5,601,819; Kostelny et al., J. Immunol. 148: 1547-1553 (1992).

As previously indicated, the subunit structures and three-dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU num-bering system; see Kabat E A et al.). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 resi-dues.

As used herein, the term "hinge region" includes the portion of a heavy chain molecule that joins the CH1 domain to the CH2 domain. This hinge region comprises approxi-mately 25 residues and is flexible, thus allowing the two N-terminal antigen binding regions to move independently. Hinge regions can be subdivided into three distinct domains: upper, middle, and lower hinge domains (Roux et al., J. Immunol. 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant invention) is obtained from a second species. In embodiments, the target binding region or site will be from anon-human source mouse or primate) and the constant region is human.

As used herein, the term "engineered antibody" refers to an antibody in which the variable domain in either the heavy or light chain or both is altered by at least partial replace-ment of one or more CDRs from, an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable domain to transfer the antigen binding capacity of one variable domain to another. Rather, it may only be necessary to transfer those residues that are necessary to maintain the activity of the target binding site.

It is further recognized that the framework regions within the variable domain in a heavy or light chain, or both, of a humanized antibody may comprise solely residues of human origin, in which case these framework regions of the humanized antibody are referred to as "fully human framework regions." Alternatively, one or more residues of the framework region(s) of the donor variable domain can be engineered within the corresponding position of the human framework region(s) of a variable domain in a heavy or light chain, or both, of a humanized antibody if necessary to maintain proper binding or to enhance binding to the TCR antigen. A human framework region that has been engineered in this manner would thus comprise a mixture of human and donor framework residues, and is referred to herein as a "partially human framework region."

For example, humanization of an anti-TCR antibody can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent or mutant rodent CDRs or CDR sequences for the corresponding sequences of a human anti-TCR antibody. See also U.S. Pat. Nos. 5,225,539; 5,585,089; 5,693,761; 5,693,762; 5,859,205; herein incorporated by reference. The resulting humanized anti-TCR antibody would comprise at least one rodent or mutant rodent CDR within the fully human framework regions of the variable domain of the heavy and/or light chain of the humanized antibody. In some instances, residues within the framework regions of one or more variable domains of the humanized anti-TCR antibody are replaced by corresponding non-human (for example, rodent) residues (see, for example, U.S. Pat. Nos. 5,585,089; 5,693,761; 5,693,762; and 6,180,370), in which case the resulting humanized anti-TCR antibody would comprise partially human framework regions within the variable domain of the heavy and/or light chain.

Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the CDRs correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details, see Jones et al., Nature 331:522-525 (1986); Riechmann et al., Nature 332:323-329 (1988); and Presta, Curr. Op. Strict. Biol. 2:593-596 (1992); herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

As used herein, the terms "linked," "fused," or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the terms "treat" or "treatment" refer to both therapeutic treatment and prophylactic or preventative measures, wherein the object is to prevent or slow down (lessen) an undesired physiological change or disorder, such as the progression of multiple sclerosis, arthritis, or cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on.

As used herein, phrases such as "a subject that would benefit from administration of an anti-TCR antibody" and "an animal in need of treatment" and "a subject in need thereof" includes subjects, such as mammalian subjects, that would benefit from administration of an anti-TCR antibody used, e.g., to stimulate certain population of T cells in vivo for numeric expansion, for detection of an anti-TCR polypeptide (e.g., for a diagnostic procedure) and/or from treatment, i.e., palliation or prevention of a disease, with an anti-TCR antibody. As described in more detail herein, an anti-TCR antibody can be used in unconjugated form or can be conjugated, e.g., to a drug, prodrug, or an isotope.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

II. INTRODUCTION

Figure 8A:
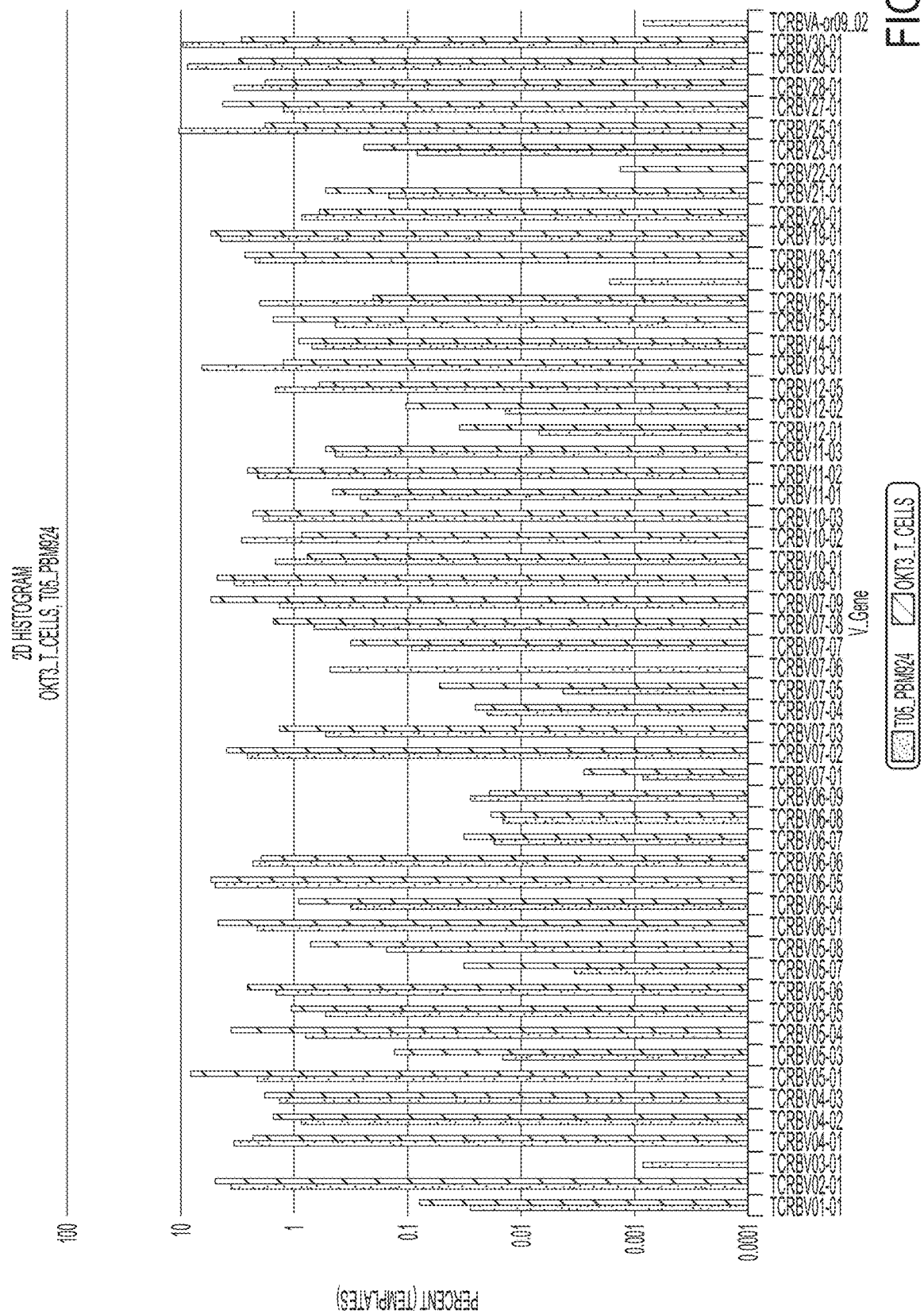
Figure 8A:
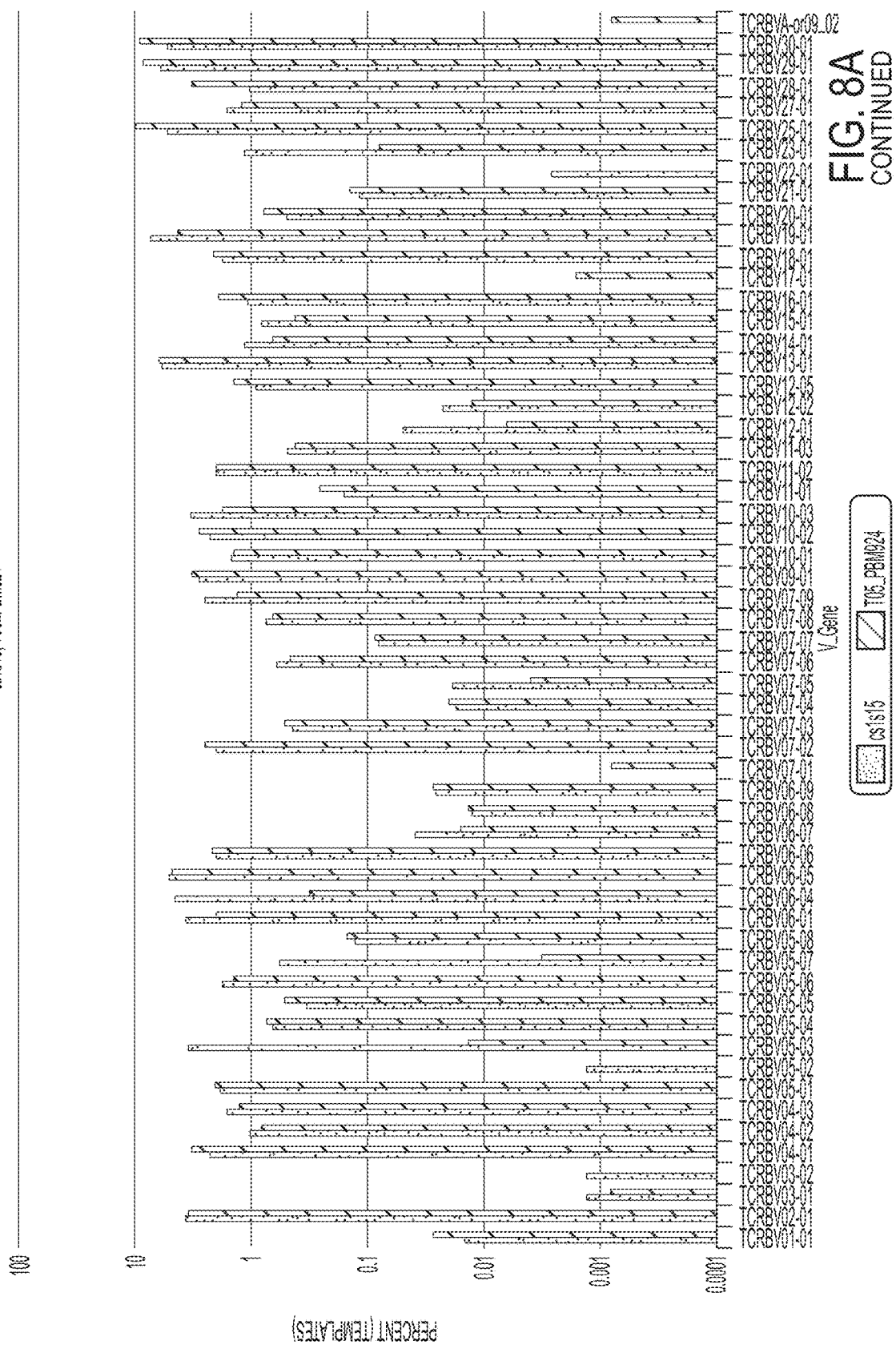
Figure 8B:
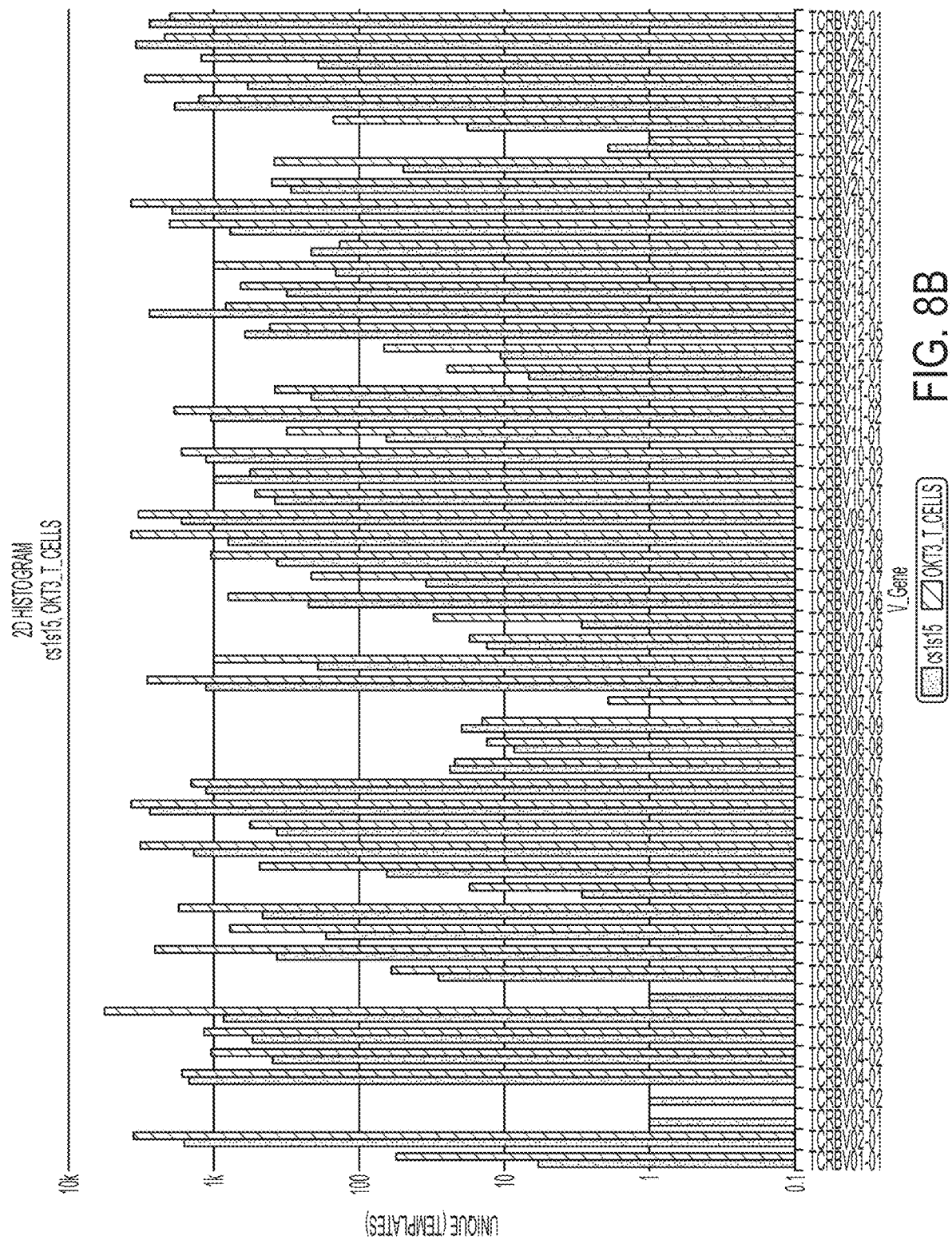
Figure 8C:
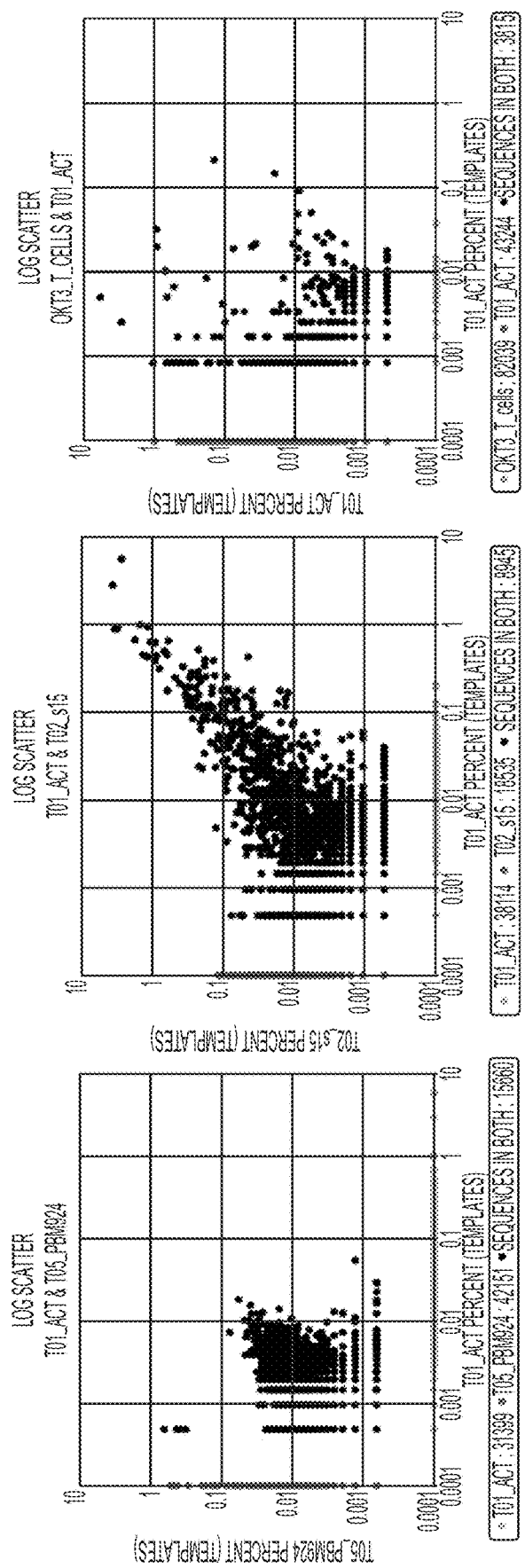
Figure 9:
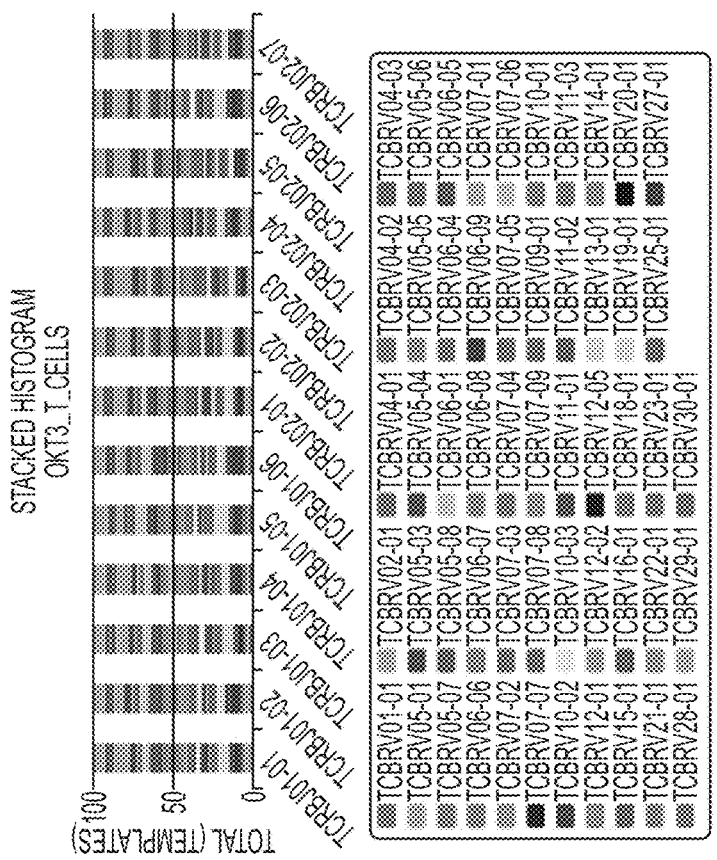
FIG. 9. V-J Paired gene frequency. Stalked histograms show V-J paired gene frequency in any particular locus for T cells grown on K562-S15 with co-stimulation (clone CS1S15) and for T cells grown on K562-OKT3 (Clone K562 OKT3) with co-stimulation.
Figure 9:
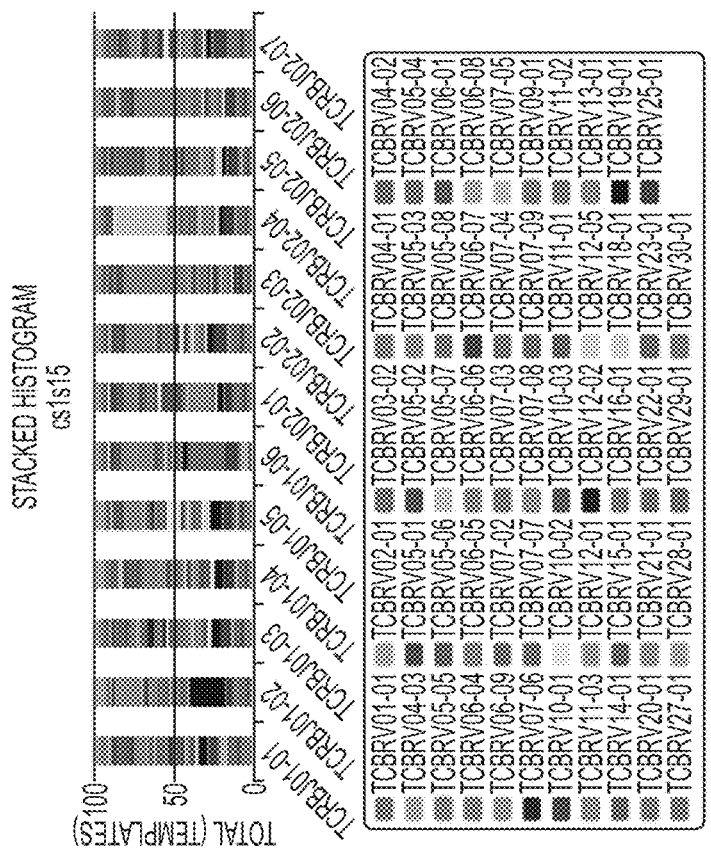
Figure 10:
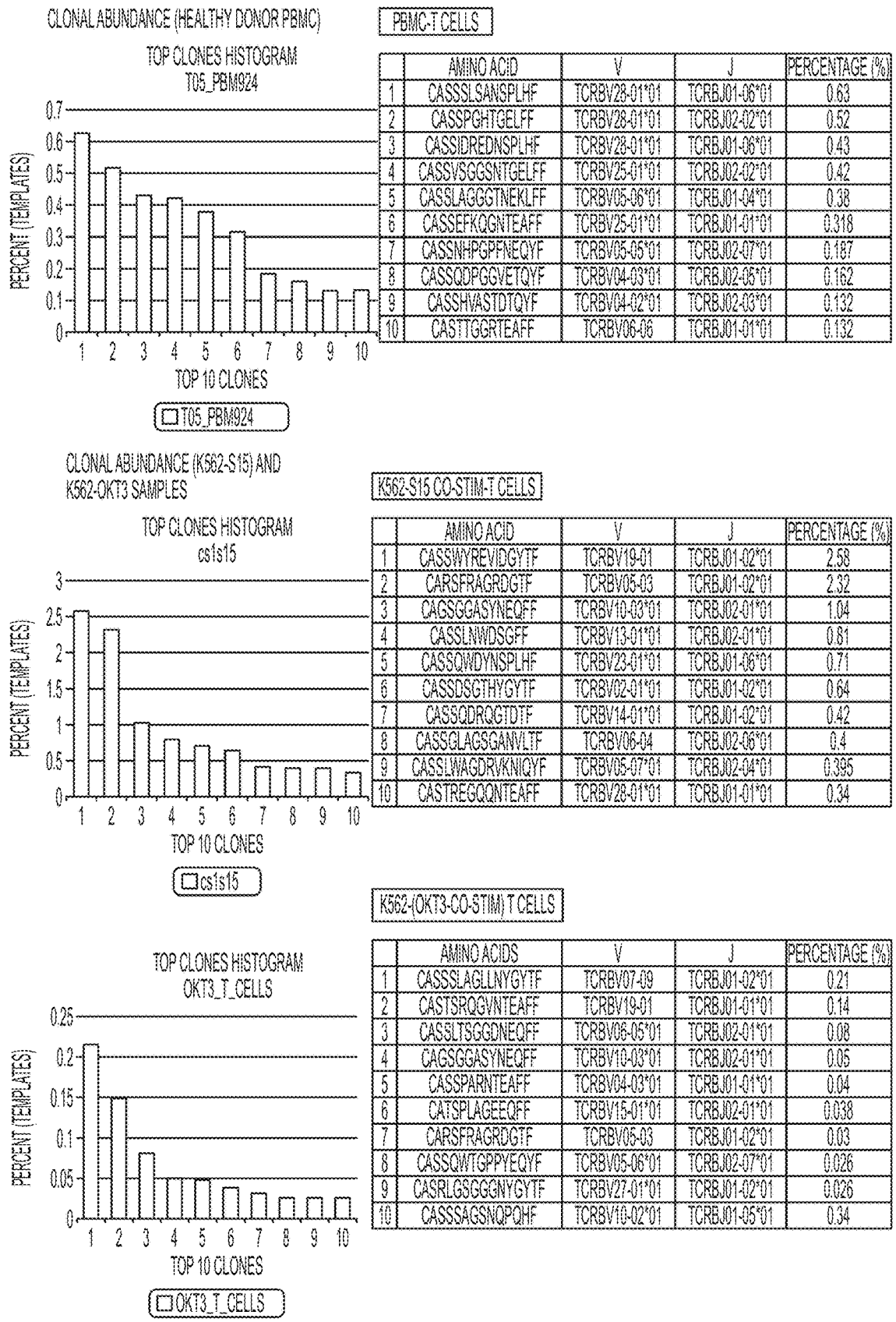
FIG. 10. Clonal hierarchy of unmanipulated T cells versus activated T cells as analyzed from NGS data after deep sequencing. Clones in highest ranking (1-10) based on percentage of productive sequencing reads represented by each clone in healthy donor PBMC sample used for T cell activation and propagation (top panel). Table shows amino acid sequences of corresponding TCR CDR3, along with V and J family alleles and respective percentage. A comparison of top clone frequency between T cells activated by K562-S15 vs. K562-OKT3 are shown as histograms (lower panels). Y-axis represents percentage of total counts per samples.

Therapeutics that employ T-cells for targeting specific antigens (e.g., tumor-associated antigens) are currently being investigated for the treatment of a variety of disease from cancers to infectious disease. However, the complexity of these agents requires specialized tools for the purification, propagation and/or activation of T-cells. Embodiments of the application provide antibodies or antigen binding fragments thereof, e.g., scFv, that specifically bind to T-cells, in particular through binding to TCR with moderate affinity and can be used to selectively purify, propagate and/or activate T-cells, independent of the epitope that is recognized by the T-cell. For example, in one aspect, antibodies are provided that specifically bind TCRα chain and engages T-cells that recognize a plurality of T-cell epitopes. The modified 79A-15 ("S15"), 79A-11 ("S11"), 79A-13 ("S13"), 79A-23 ("S23") monoclonal antibodies, for instance, specifically bind to TCRα within specific conformation so as to engage αβ-TCR. This conformational specific binding is used to analyze, isolate or propagate and/or activate T-cells. aAPCs, such as K562 cells, comprising a cell surface anti-TCR antibody of the embodiments can be used to activate and thereby to propagate primary T-cell populations (see, e.g., FIG. 7). In some aspects of the invention, K562 cells are HLAC positive, in other aspects, K562 cells are HLAC negative. Moreover, T-cell populations expanded by such aAPC expressing anti-TCR antibodies demonstrate a wide variety of clonotypes encompassing polyclonal T-cell repertoire (FIGS. 8-10). Further, optimal stimulation of T cells through a TCR directed scFv preserved donor T cells repertoire better than similar other method of T cell stimulation currently in vogue. Thus, the methods detailed herein provide new methods for generalized T-cell expansion.

III. TARGET POLYPEPTIDE

In embodiments, the binding molecules of the invention specifically bind to a T-cell receptor containing an α and a β chain (αβ-TCR). In embodiments, the binding molecules of the invention specifically bind to the invariant region of the TCRα chain, located at the Va24-J18 junction region (GSTLGR (SEQ ID NO:1)) of the T-cell receptor α-chain. In embodiments, T-cells can be expanded and/or activated by αβ-TCR cross-linking via a TCR alpha chain specific binding molecule in αβ TCR$^+$ T-cells. In embodiments, the binding molecules of the invention therefore specifically bind TCRs containing the invariant GSTLGR (SEQ ID NO:1) regardless of T cell clonotype.

IV. ANTI-TCR ANTIBODIES

In certain embodiments, an antibody or a fragment thereof that binds to TCR polypeptide and stimulates T-cell growth ex vivo. In certain aspects, the antibodies provided here bind to TCR essentially independently of epitope recognized by the TCR and can be used to stimulate expansion of T-cells having a variety of clonotypes. The antibody may be selected from the group consisting of a chimeric antibody, an affinity matured antibody, a polyclonal antibody, a monoclonal antibody, a humanized antibody, a human antibody, or an antigen-binding antibody fragment or a natural or synthetic ligand. Preferably, the anti-TCR antibody is a monoclonal antibody or a humanized antibody.

Examples of antibody fragments suitable for the present embodiments include, without limitation: (i) the Fab fragment, consisting of $V_L$, $V_H$, $C_L$, and $C_{H1}$ domains; (ii) the "Fd" fragment consisting of the $V_H$ and $C_{H1}$ domains; (iii) the "Fv" fragment consisting of the $V_L$ and $V_H$ domains of a single antibody; (iv) the "dAb" fragment, which consists of a $V_H$ domain; (v) isolated CDR regions; (vi) F(ab')2 fragments, a bivalent fragment comprising two linked Fab fragments; (vii) single chain Fv molecules ("scFv"), wherein a $V_H$ domain and a $V_L$ domain are linked by a peptide linker that allows the two domains to associate to form a binding domain; (viii) bi-specific single chain Fv dimers (see U.S. Pat. No. 5,091,513); and (ix) diabodies, multivalent or multispecific fragments constructed by gene fusion (US Patent App. Pub. 20050214860). Fv, scFv, or diabody molecules may be stabilized by the incorporation of disulphide bridges linking the $V_H$ and $V_L$ domains. Minibodies comprising a scFv joined to a CH3 domain may also be made (Hu et al., 1996).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

In one embodiment, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881,557). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

An antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

In embodiments, the invention provides an isolated antibody or antigen-binding fragment thereof that specifically binds to an epitope of T-cell receptor alpha (TCRα) polypeptide comprising sequence GSTLRG (SEQ ID NO:1).

In embodiments, the antibody or antigen-binding fragment thereof that specifically binds to TCRα polypeptide, comprises (a) HCDR1 at least 80%, 85%, 90% or 95% identical to SEQ ID NO: 2; (b) HCDR2 at least 80%, 85%, 90% or 95% identical to SEQ ID NO: 3; (c) HCDR3 is identical to CDYW (SEQ ID NO:21); CAYW (SEQ ID NO:23); or CAYL (SEQ ID NO:22); (d) LCDR1 at least 80%, 85%, 90% or 95% identical to SEQ ID NO: 4 or SEQ ID NO: 9; (e) LCDR2 at least 80%,85%, 90% or 95% identical to SEQ ID NO: 5; and (f) LCDR3 at least 80%, 85%, 90% or 95% identical to SEQ ID NO: 6 or SEQ ID NO: 10. In embodiments, The antibody or antigen-binding fragment thereof, comprises (a) HCDR1 identical to SEQ ID NO: 2; (b) HCDR2 identical to SEQ ID NO: 3; (c) HCDR3 identical to CDYW (SEQ ID NO:21); CAYW (SEQ ID NO:23); or CAYL (SEQ ID NO:22); (d) LCDR1 identical to SEQ ID NO: 4; or SEQ ID NO: 9; (e) LCDR2 identical to SEQ ID NO: 5; and (f) LCDR3 identical to SEQ ID NO: 6; or SEQ ID NO: 10.

The invention further provides an antibody or antigen-binding fragment thereof that specifically binds to TCRα polypeptide comprising (a) HCDR1 at least 80%, 85%, 90% or 95% identical to $V_H$ CDR1 of 79A-15 SEQ ID NO: 2; (b) HCDR2 at least 80%, 85%, 90% or 95% identical to $V_H$ CDR2 of 79A-15 SEQ ID NO: 3; (c) HCDR3 at least 80%, 85%, 90% or 95% identical to $V_H$ CDR3 of 79A-15 CAYL (SEQ ID NO:22); (d) LCDR1 at least 80%, 85%, 90% or 95% identical to $V_L$ CDR1 of 79A-15 SEQ ID NO: 9; (e) LCDR2 at least 80%, 85%, 90% or 95% identical to $V_L$ CDR2 of 79A-15 SEQ ID NO: 5; and (f) LCDR3 at least 80%, 85%, 90% or 95% identical to $V_L$ CDR3 of 79A-15 SEQ ID NO: 10.

The invention additionally provides an isolated antibody or antigen binding fragment that specifically binds TCRα polypeptide, comprising a $V_H$ domain at least about 80%, 85%, 90% or 95% identical to the $V_H$ domain of 79A-15 (SEQ ID NO: 11) and a $V_L$ domain at least about 80%, 85%, 90% or 95% identical to the $V_L$ domain of 79A-15 (SEQ ID NO: 12). In embodiments, the isolated antibody or antigen binding fragment comprises a $V_L$ domain between 90% and 99% identical to the $V_H$ domain of 79A-15 (SEQ ID NO: 11) and a VL domain between 90 and 99% identical to the $V_L$ domain of 79A-15 (SEQ ID NO: 12). In additional embodiments, the isolated antibody or antigen binding fragment thereof comprises a $V_H$ domain identical to the $V_H$ domain of 79A15 (SEQ ID NO: 11) and a $V_L$ domain identical to the $V_L$ domain of 79A-15 (SEQ ID NO: 12).

The invention further provides an isolated antibody or antigen binding fragment thereof that specifically binds to TCRα polypeptide, comprising (a) HCDR1 at least 80%, 85%, 90% or 95% identical to $V_H$ CDR1 of 79A-13 KASGYTFTDYYMNWV (SEQ ID NO: 2); (b) HCDR2 at least 80%, 85%, 90% or 95% identical to $V_H$ CDR2 of 79A-13 WIGEINPNN (SEQ ID NO: 3); (c) HCDR3 at least 80%, 85%, 90% or 95% identical to $V_H$ CDR3 of 79A-13 CAYL (SEQ ID NO:22); (d) LCDR1 at least 80%, 85%, 90% or 95% identical to $V_L$ CDR1 of 79A-13 NTYLEWY (SEQ ID NO: 4); (e) LCDR2 at least 80%, 85%, 90% or 95% identical to $V_L$ CDR2 of 79A-13 KLLIYKVSNRFS (SEQ ID NO: 5); and (f) LCDR3 at least 80%, 85%, 90% or 95% identical to $V_L$ CDR3 of 79A-13 MQGSHVPW (SEQ ID NO: 10). In additional embodiments, the invention provides an isolated antibody or antigen binding fragment thereof, comprising (a) HCDR1 identical to KASGYTFTDYYMNWV (SEQ ID NO: 2); (b) HCDR2 identical to WIGEINPNN (SEQ ID NO: 3); (c) HCDR3 identical to CAYL (SEQ ID NO:22); (d) LCDR1 identical to NTYLEWY (SEQ ID NO: 4); (e) LCDR2 is identical to KLLIYKVSNRFS (SEQ ID NO: 5); and (f) LCDR3 identical to MQGSHVPW (SEQ ID NO: 10).

In additional embodiments, the invention provides isolated antibody or antigen binding fragment thereof that specifically binds to TCRα polypeptide comprising a $V_H$ domain at least about 80%, 85%, 90% or 95% identical to the $V_H$ domain of 79A-13 (SEQ ID NO: 11) and a $V_L$ domain at least about 80%, 85%, 90% or 95% identical to the $V_L$ domain of 79A-13 (SEQ ID NO: 14). In embodiments, the isolated antibody or antigen binding fragment comprises a $V_H$ domain between 90% and 99% identical to the $V_H$ domain of 79A-13 (SEQ ID NO: 11) and a $V_L$ domain between 90% and 99% identical to the $V_L$ domain of 79A-13 (SEQ ID NO: 14). In further embodiments, the isolated antibody or antigen binding fragment comprises a $V_H$ domain identical to the $V_H$ domain of 79A-13 (SEQ ID NO: 11) and a $V_L$ domain identical to the $V_L$ domain of 79A-13 (SEQ ID NO: 14).

The invention further provides an antibody or antigen-binding fragment thereof that specifically binds to TCRα polypeptide, comprising (a) HCDR1 at least 80%, 85%, 90% or 95% identical to $V_H$ CDR1 of 79A-11 KASGYTFTDYYMNWV (SEQ ID NO: 2); (b) HCDR2 at least 80%, 85%, 90% or 95% identical to $V_H$ CDR2 of 79A-11 WIGEINPNN (SEQ ID NO: 3); (c) HCDR3 at least 80%, 85%, 90% or 95% identical to $V_H$ CDR3 of 79A-11 CAYW (SEQ ID NO:23); (d) LCDR1 at least 80%, 85%, 90% or 95% identical to $V_L$ CDR1 of 79A-11 NTYLEWF (SEQ ID NO: 9); (e) LCDR2 at least 80%, 85%, 90% or 95% identical to $V_L$ CDR2 of 79A-11 KLLIYKVSNRFS (SEQ ID NO: 5); and (f) LCDR3 at least 80%, 85%, 90% or 95% identical to $V_L$ CDR3 of 79A-11 MQGSHVPW (SEQ ID NO: 10). In embodiments, the antibody or antigen-binding fragment thereof comprises (a) HCDR1 is identical to KASGYTFTDYYMNWV (SEQ ID NO: 2); (b) HCDR2 is identical to WIGEINPNN (SEQ ID NO: 3); (c) HCDR3 is identical to CAYW (SEQ ID NO:23); (d) LCDR1 is identical to NTYLEWF (SEQ ID NO: 9); (e) LCDR2 is identical to KLLIYKVSNRFS (SEQ ID NO: 5); and (f) LCDR3 is identical to MQGSHVPW (SEQ ID NO: 10).

In embodiments, the invention provides an antibody or antigen-binding fragment thereof that specifically binds to TCRα polypeptide, comprising a $V_H$ domain at least about 80%, 85%, 90% or 95% identical to the $V_H$ domain of 79A-11 (SEQ ID NO: 13) and a $V_L$ domain at least about 80%, 85%, 90% or 95% identical to the $V_L$ domain of 79A-11 (SEQ ID NO: 12). In embodiments, the isolated antibody or antigen binding fragment thereof comprises a $V_H$ domain between 90% and 99% identical to the $V_H$ domain of 79A-11 (SEQ ID NO: 13) or a $V_L$ domain between 90% and 99% identical to the $V_L$ domain of 79A-11 (SEQ ID NO: 12). In additional embodiments, the isolated antibody or antigen binding fragment thereof of claim 16, comprising a $V_H$ domain identical to the $V_H$ domain of 79A11 (SEQ ID NO: 13) and a $V_L$ domain identical to the $V_L$ domain of 79A11 (SEQ ID NO: 12).

The invention further provides an isolated antibody or antigen binding fragment thereof that specifically binds to TCRα polypeptide, comprising (a) HCDR1 at least 80%, 85%, 90% or 95% identical to $V_H$ CDR1 of 79A KASGYTFTDYYMNWV (SEQ ID NO: 2); (b) HCDR2 at least 80%, 85%, 90% or 95% identical to $V_H$ CDR2 of 79A WIGEINPNN (SEQ ID NO: 3); (c) HCDR3 at least 80%, 85%, 90% or 95% identical to $V_H$ CDR3 of 79A CDYW (SEQ ID NO:21); (d) LCDR1 at least 80%, 85%, 90% or 95% identical to $V_L$ CDR1 of 79A NTYLEWY (SEQ ID NO: 4); (e) LCDR2 at least 80%, 85%, 90% or 95% identical to $V_L$ CDR2 of 79A KLLIYKVSNRFS (SEQ ID NO: 5); and (f) LCDR3 at least 80%, 85%, 90% or 95% identical to $V_L$ CDR3 of 79A FQGSHVPW (SEQ ID NO: 6). In embodiments, the isolated antibody or antigen binding fragment comprises (a) HCDR1 is identical to KASGYTFTDYYMNWV (SEQ ID NO: 2); (b) HCDR2 is identical to WIGEINPNN (SEQ ID NO: 3); (c) HCDR3 is identical to CDYW (SEQ ID NO:21); (d) LCDR1 is identical to NTYLEWY (SEQ ID NO: 4); (e) LCDR2 is identical to KLLIYKVSNRFS (SEQ ID NO: 5); and (f) LCDR3 is identical to FQGSHVPW (SEQ ID NO: 6).

The invention further provides an isolated antibody or antigen binding fragment thereof that specifically binds to TCRα polypeptide, comprising a $V_H$ domain at least about 80%, 85%, 90% or 95% identical to the $V_H$ domain of 79A (SEQ ID NO: 7) and a $V_L$ domain at least about 80%, 85%, 90% or 95% identical to the $V_L$ domain of 79A (SEQ ID NO: 8). In embodiments, the isolated antibody or antigen binding fragment comprises a $V_H$ domain between 90% and 99% identical to the $V_H$ domain of 79A (SEQ ID NO: 7) or a $V_L$ domain between 90% and 99% identical to the $V_L$ domain of 79A (SEQ ID NO: 8). In embodiments, the isolated antibody or antigen binding fragment comprises a $V_H$ domain identical to the $V_H$ domain of 79A (SEQ ID NO: 7) and a $V_L$ domain identical to the $V_L$ domain of 79A (SEQ ID NO: 8).

In embodiments, the invention provides an isolated antibody or antigen binding fragment thereof that specifically binds to TCRα polypeptide, comprising (a) HCDR1 at least 80%, 85%, 90% or 95% identical to KASGYTFTGYYMNWV (SEQ ID NO:15); (b) HCDR2 at least 80%, 85%, 90% or 95% identical to WIGGINPNN (SEQ ID NO:16); (c) HCDR3 identical to CRYW (SEQ ID NO:17); (d) LCDR1 at least 80%, 85%, 90% or 95% identical to QSIVHGGGNTY (SEQ ID NO:18); (e) LCDR2 at least 80%, 85%, 90% or 95% identical to KLLIYKVSNRFS (SEQ ID NO: 5); and (f) LCDR3 at least 80%, 85%, 90% or 95% identical to FQGSHVPW (SEQ ID NO: 6). In embodiments, the isolated antibody or antigen binding fragment thereof comprises (a) HCDR1 identical to KASGYTFTGYYMNWV (SEQ ID NO:15); (b) HCDR2 identical to WIGGINPNN (SEQ ID NO:16); (c) HCDR3 identical to CRYW (SEQ ID NO:17); (d) LCDR1 identical to QSIVHGGGNTY (SEQ ID NO:18); (e) LCDR2 identical to KLLIYKVSNRFS (SEQ ID NO: 5); and (f) LCDR3 identical to FQGSHVPW (SEQ ID NO: 6).

The invention further provides anti-TCR antibody or antigen binding fragments thereof, comprising a $V_H$ domain at least about 80%, 85%, 90% or 95% identical to the $V_H$ domain of 79A-23 (SEQ ID NO: 19) and a $V_L$ domain at least about 80%, 85%, 90% or 95% identical to the $V_L$ domain of 79A-23 (SEQ ID NO:20). In embodiments, the isolated antibody or antigen binding fragment thereof comprises a $V_H$ domain between 90% and 99% identical to the $V_H$ domain of 79A-23 (SEQ ID NO: 19) and a $V_L$ domain between 90 and 99% identical to the $V_L$ domain of 79A-23 (SEQ ID NO: 20). In further embodiments, the isolated antibody or antigen binding fragment thereof comprises a $V_H$ domain identical to the $V_H$ domain of 79A-23 (SEQ ID NO: 19) and a $V_L$ domain identical to the $V_L$ domain of 79A-23 (SEQ ID NO: 20).

In embodiments, the anti-TCR antibody or antigen binding fragments thereof provided herein are multispecific, e.g., bispecific. In embodiments, the antibodies and antigen-binding fragments provided herein that specifically bind to TCRα polypeptide are a Fab fragment, a Fv fragment and/or are single chain. In embodiments, the anti-TCR antibodies and antigen-binding fragments provided herein are multivalent and comprise at least two heavy chains and at least two light chains. In embodiments, the antibodies and antigen-binding fragments provided herein that specifically bind to TCRα polypeptide comprise a light chain constant region selected from the group consisting of a human kappa constant region and a human lambda constant region.

In embodiments, the anti-TCR antibodies and antigen-binding fragments provided herein comprise a heavy chain constant region or fragment thereof. In embodiments, the antibodies and antigen-binding fragments provided herein that specifically bind to TCRα polypeptide comprise a heavy chain constant region or fragment thereof which is human IgG1, IgG2, IgG3, IgG4, IgM, IgA1, IgA2, IgE, or IgD.

In embodiments, the antibody or antigen binding fragment thereof specifically binds to an epitope of T-cell receptor alpha (TCRα) polypeptide comprising the sequence GSTLRG (SEQ ID NO:1) with an affinity characterized by a dissociation constant ($K_D$) no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $8.4\times10^{-12}$ M, $10^{-12}$ M, $5\times10^{-13}$ M, $10^{-13}$ M, $5\times10^{-14}$ M, $10^{-14}$ M, $5\times10^{-15}$ M or $10^{-15}$ M. In embodiments, the $K_D$ is about $5\times10^{-9}$ M to about $6\times10^{-9}$M. In further embodiments, the $K_D$ is about $1\times10^{-9}$M to about $2\times10^{-9}$M.

In embodiments, the antibodies and antigen-binding fragments provided herein that specifically bind to TCRα polypeptide is humanized, primatized or chimeric. In embodiments, the antibodies and antigen-binding fragments provided herein that specifically bind to TCRα polypeptide is humanized.

In embodiments, the anti-TCR antibody or antigen binding fragment thereof of the invention comprises a VH and VL domain separated by a linker. In embodiments the antibody or antigen binding fragment thereof of the invention, further comprises a transmembrane domain. In embodiments, the antibody or antigen binding fragment thereof comprising a VH and VL domain separated by a linker comprises a VH polypeptide at least 90% identical to a polypeptide selected from the group consisting of a SEQ ID NO:11, SEQ ID NO:13 and SEQ ID NO:19, and the VL is a polypeptide at least 90% identical to a polypeptide selected from the group consisting of SEQ ID NO:12, SEQ ID NO:14 and SEQ ID NO:20.

In embodiments, the anti-TCR antibody or fragment disclosed herein contains a VH polypeptide at least 90% identical to SEQ ID NO:11 and a VL polypeptide at least 90% identical to SEQ ID NO:12, wherein the VH and VL is separated by a linker.

In embodiments, the anti-TCR antibody or fragment disclosed herein contains a VH polypeptide at least 90% identical to SEQ ID NO:13 and a VL polypeptide at least 90% identical to SEQ ID NO:12, wherein the VH and VL is separated by a linker.

The invention further provides an anti-TCR antibody or fragment containing a VH polypeptide at least 90% identical to SEQ ID NO:11 and a VL polypeptide at least 90% identical to SEQ ID NO:14, wherein the VH and VL is separated by a linker.

In embodiments, the anti-TCR antibody or fragment disclosed herein contains a VH polypeptide at least 90% identical to SEQ ID NO:19 and a VL polypeptide at least 90% identical to SEQ ID NO:20, wherein the VH and VL is separated by a linker.

Thus, in embodiments, the anti-TCR antibody or antigen-binding fragment disclosed herein is a single-chain Fv fragment (scFv), e.g., a heterodimer containing the VH and VL domains, which are connected by a linker, forming a single polypeptide.

In embodiments, the linker is a polypeptide between 10-30 amino acids in length, between 15-25 amino acids in length, between 15 and 20 amino acids in length. In embodiments, the linker is 15, 16, 17, 18, 19, 20, 21, 22, 23, or 25 amino acids in length. Suitable linkers for scFv are known to those of skill in the art. For example, multimers of the GGGGS (G45 or Gly4Ser) are suitable linkers. Exemplary G45 multimers include the 15-mer (G4S)$_3$, and the 20-mers (G4s)$_4$. A further exemplary linker is the 18-mer GGSSRSSSSGGGGSGGGG. Exemplary sequences with added functionalities, such as an epitope tag or an encoding sequence containing a Cre-Lox recombination site or sequences improving scFv properties, are also contemplated as linker sequences.

V. POLYNUCLEOTIDES ENCODING ANTI-TCR ANTIBODIES

The present invention also includes fragments of the polynucleotides of the invention, as described elsewhere. Additionally, polynucleotides that encode fusion polypeptides, Fab fragments, and other derivatives, as described herein, are also contemplated by the invention.

The polynucleotides are produced or manufactured by methods known in the art. For example, if the nucleotide sequence of the antibody is known, a polynucleotide encoding the antibody may be assembled from chemically synthesized oligonucleotides (e.g., as described in Kutmeier et al., Bio Techniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an anti-TCR antibody, or antigen-binding fragment, variant, or derivative thereof of the invention, may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, preferably poly A+RNA, isolated from, any tissue or cells expressing the antibody or other anti-TCR antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody or other anti-TCR antibody. Amplified nucleic acids generated by PCR may then be cloned into replicable cloning vectors using any method well known in the art.

Once the nucleotide sequence and corresponding amino acid sequence of the anti-TCR antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al. (1990) Molecular Cloning, A Laboratory Manual (2nd ed.; Cold Spring Harbor Laboratory, Cold Spring Harbor, N.Y.) and Ausubel et al., eds. (1998) Current Protocols in Molecular Biology (John Wiley & Sons, NY), which are both incorporated by reference herein in their entireties), to generate antibodies having a different amino acid sequence, for example to create amino acid substitutions, deletions, and/or insertions.

A polynucleotide encoding an anti-TCR binding molecule, e.g., an antibody, or antigen-binding fragment, variant, or derivative thereof, can be composed of any polyribonucleotide or polydeoxyribonucleotide, which may be unmodified RNA or DNA or modified RNA or DNA. For example, a polynucleotide encoding anti-TCR antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, a polynucleotide encoding an anti-TCR binding molecule, e.g., an antibody, or antigen-binding fragment, variant, or derivative thereof can be composed of triple-stranded regions comprising RNA or DNA or both RNA and DNA. A polynucleotide encoding an anti-TCR binding molecule, e.g., antibody, or antigen-binding fragment, variant, or derivative thereof, may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

In embodiments, the invention provides an isolated polynucleotide comprising a nucleic acid encoding an antibody or antigen binding fragment thereof that specifically binds to a TCRα chain, said antibody binding to an epitope of TCRα polypeptide comprising the sequence GSTLRG (SEQ ID NO: 1).

In embodiments, the invention provides a nucleic acid encoding a VH polypeptide at least 90% identical to SEQ ID NO:11, SEQ ID NO:13 or SEQ ID NO:19. In embodiments, the invention provides a nucleic acid encoding a nucleic acid encoding a VL polypeptide at least 90% identical to, SEQ ID NO:12, SEQ ID NO:14 or SEQ ID NO:20.

The invention further provides a nucleic acid encoding a HCDR1 amino acid sequence identical to SEQ ID NO:2 or SEQ ID NO:15; a HCDR2 amino acid sequence identical to SEQ ID NO:3 or SEQ ID NO:16; and/or a HCDR3 amino acid sequence identical to SEQ ID NO:21, SEQ ID NO:22, SEQ ID NO:23, or SEQ ID NO:17.

The invention further provides a nucleic acid encoding a LCDR1 amino acid sequence identical to SEQ ID NO:4, 9 or 18; a LCDR2 amino acid sequence identical to SEQ ID NO:5, and/or a nucleic acid encoding a LCDR3 amino acid sequence identical to SEQ ID NO:6, or 10.

The invention further provides an isolated polynucleotide comprising a nucleic acid encoding a VH polypeptide, wherein said VH polypeptide comprises HCDR1, HCDR2 and HCDR3 amino acid sequences comprising SEQ ID NOs:2, 3, and 21, respectively, and wherein an antibody or antigen fragment comprising said VH polypeptide specifically binds an epitope of T-cell receptor alpha (TCRα) polypeptide comprising sequence GSTLRG (SEQ ID NO:1).

The invention also provides an isolated polynucleotide comprising a nucleic acid encoding a VH polypeptide, wherein said VH polypeptide comprises HCDR1, HCDR2, and HCDR3 amino acid sequences comprising SEQ ID NOs: 2, 3, and 22, respectively, and wherein an antibody or antigen fragment comprising said VH polypeptide specifically binds an epitope of T-cell receptor alpha (TCRα) polypeptide comprising sequence GSTLRG (SEQ ID NO:1).

In embodiments, the invention is directed to an isolated polynucleotide comprising a nucleic acid encoding a VH polypeptide, wherein said VH polypeptide comprises HCDR1, HCDR2, and HCDR3 amino acid sequences comprising SEQ ID NOs: 2, 3, and 23, respectively, and wherein an antibody or antigen fragment comprising said VH polypeptide specifically binds an epitope of T-cell receptor alpha (TCRα) polypeptide comprising sequence GSTLRG (SEQ ID NO:1).

In further embodiments, the invention provides an isolated polynucleotide comprising a nucleic acid encoding a VH polypeptide, wherein said VH polypeptide comprises HCDR1, HCDR2, and HCDR3 amino acid sequences comprising SEQ ID NOs:15, 16, and 17, respectively, and wherein an antibody or antigen fragment comprising said VH polypeptide specifically binds an epitope of T-cell receptor alpha (TCRα) polypeptide comprising sequence GSTLRG (SEQ ID NO:1).

The invention is further directed to, in embodiments, an isolated polynucleotide comprising a nucleic acid encoding a VL polypeptide, wherein said VL polypeptide comprises LCDR1, LCDR2, and LCDR3 amino acid sequences comprising SEQ ID NOs:4, 5 and 6, respectively, and wherein an antibody or antigen fragment comprising said VL polypeptide specifically binds an epitope of T-cell receptor alpha (TCRα) polypeptide comprising sequence GSTLRG (SEQ ID NO:1).

In embodiments, the invention provides an isolated polynucleotide comprising a nucleic acid encoding a VL polypeptide, wherein said VL polypeptide comprises LCDR1, LCDR2, and LCDR3 amino acid sequences comprising SEQ ID NOs: 9, 5 and 10, respectively, and wherein an antibody or antigen fragment comprising said VL polypeptide specifically binds an epitope of T-cell receptor alpha (TCRα) polypeptide comprising sequence GSTLRG (SEQ ID NO:1).

The invention further provides an isolated polynucleotide comprising a nucleic acid encoding a VL polypeptide, wherein said VL polypeptide comprises LCDR1, LCDR2, and LCDR3 amino acid sequences comprising SEQ ID NOs: 4, 5 and 10, respectively, and wherein an antibody or antigen fragment comprising said VL polypeptide specifically binds an epitope of T-cell receptor alpha (TCRα) polypeptide comprising sequence GSTLRG (SEQ ID NO:1).

In embodiments, the invention provides an isolated polynucleotide comprising a nucleic acid encoding a VL polypeptide, wherein said VL polypeptide comprises LCDR1, LCDR2, and LCDR3 amino acid sequences comprising SEQ ID NOs: 18, 5 and 6, respectively, and wherein an antibody or antigen fragment comprising said VL polypeptide specifically binds an epitope of T-cell receptor alpha (TCRα) polypeptide comprising sequence GSTLRG (SEQ ID NO:1).

VI. FUSION PROTEINS AND ANTIBODY CONJUGATES

As discussed in more detail elsewhere herein, anti-TCR binding molecules, e.g., antibodies of the invention, or antigen-binding fragments, variants, or derivatives thereof, may further be recombinantly fused to a heterologous polypeptide at the N- or C-terminus or chemically conjugated (including covalent and non-covalent conjugations) to polypeptides or other compositions. For example, anti-TCR antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

Anti-TCR antibodies of the invention, or antigen-binding fragments, variants, or derivatives thereof, may include derivatives that are modified, i.e., by the covalent attachment of any type of molecule to the antibody such that covalent attachment does not prevent the antibody from binding to the target TCR. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the derivative may contain one or more non-classical amino acids.

Anti-TCR binding molecules, e.g., antibodies of the invention, or antigen-binding fragments, variants, or derivatives thereof, can be composed of amino acids joined to each other by peptide bonds or modified peptide bonds, i.e., peptide isosteres, and may contain amino acids other than the 20 gene-encoded amino acids. For example, anti-TCR antibodies may be modified by natural processes, such as posttranslational processing, or by chemical modification techniques that are well known in the art. Such modifications are well described in basic texts and in more detailed monographs, as well as in a voluminous research literature. Modifications can occur anywhere in the anti-TCR binding molecule, including the peptide backbone, the amino acid side-chains and the amino or carboxyl termini, or on moieties such as carbohydrates. It will be appreciated that the same type of modification may be present in the same or varying degrees at several sites in a given anti-TCR binding molecule. Also, a given anti-TCR binding molecule may contain many types of modifications. Anti-TCR binding molecules may be branched, for example, as a result of ubiquitination, and they may be cyclic, with or without branching. Cyclic, branched, and branched cyclic anti-TCR binding molecule may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination, (See, for instance, Proteins—Structure and Molecular Properties, T. E. Creighton, W. H. Freeman and Company, NY; 2nd ed. (1993): Johnson, ed. (1983) Posttranslational Covalent Modification of Proteins (Academic Press, NY), pgs. 1-12; Seifter et al., Meth. Enzymol. 182:626-646 (1990); Rattan et al., Ann. NY Acad. Sci. 663:48-62 (1992)).

The present invention also provides for fusion proteins comprising an anti-TCR antibody, or antigen-binding fragment, variant, or derivative thereof, and a heterologous polypeptide. The heterologous polypeptide to which the antibody is fused is useful for function or is useful to target the anti-TCR polypeptide expressing cells. For example, the binding and/or crosslinking of the TCR leads to T-cell effector functions, such as cytokine production, proliferation and killing. In another embodiment, antibody or its derivative including mutants may be fused to transmembrane domains of human immune cell surface receptors for desirable surface expression of the fusion construct on transfected cells(s) and/or for enabling desirable target recognition by the chimera causing improved effector functions.

In one embodiment, a fusion protein of the invention comprises, consists essentially of, or consists of, a polypeptide having the amino acid sequence of any one or more of the VH domains of an antibody of the invention or the amino acid sequence of any one or more of the VL, domains of an antibody of the invention or fragments or variants thereof, and a heterologous polypeptide sequence.

In another embodiment, a fusion protein for use in the diagnostic and treatment methods disclosed herein comprises, consists essentially of, or consists of a polypeptide having the amino acid sequence of any one, two, three of the CDRs of the VH domain of an anti-TCR antibody, or fragments, variants, or derivatives thereof, or the amino acid sequence of any one, two, three of the CDRs of the VL domain an anti-TCR antibody, or fragments, variants, or derivatives thereof, and a heterologous polypeptide sequence. In one embodiment, a fusion protein comprises a polypeptide having the amino acid sequence of at least one VH domain of an anti-TCR antibody of the invention and the amino acid sequence of at least one VL domain of an anti-TCR antibody of the invention or fragments, derivatives or variants thereof, and a heterologous polypeptide sequence. Preferably, the VH and VL domains of the fusion protein correspond to a single source antibody (or scFv or Fab fragment) that specifically binds at least one epitope of TCR. In yet another embodiment, a fusion protein for use in the diagnostic and treatment methods disclosed herein comprises a polypeptide having the amino acid sequence of any one, two, three or more of the CDRs of the VH domain of an anti-TCR antibody and the amino acid sequence of any one, two, three or more of the CDRs of the VL domain of an anti-TCR antibody, or fragments or variants thereof, and a heterologous polypeptide sequence. Preferably, two, three, four, five, six, or more of the CDR(s) of the VH domain or VL domain correspond to single source antibody (or say or Fab fragment) of the invention. Nucleic acid molecules encoding these fusion proteins are also encompassed by the invention.

Exemplary fusion proteins reported in the literature include fusions of the T cell receptor (Gaseoigne et al., Proc. Natl. Acad. Sci. USA 84:2936-2940 (1987)); CD4 (Capon et al., Nature 337:525-531 (1989); Traunecker et al., Nature 339:68-70 (1989); Zettmeissl et al., DNA Cell Biol. USA 9:347-353 (1990); and Byrn et al., Nature 344:667-670 (1990)); L-selectin (homing receptor) (Watson et al., J. Cell. Biol. 110:2221-2229 (1990); and Watson et al., Nature 349:164-167 (1991)); CD44 (Aruffo et al., Cell 61:1303-1313 (1990)); CD28 and 137 (Linsley et al., J. Exp. Med. 173:721-730 (1991)); CTLA-4 (Lisley et al., J. Exp. Med. 174:561-569 (1991)); CD22 (Stamenkovie et al., Cell 66:1133-1144 (1991)); TNF receptor (Ashkenazi et al., Proc. Natl. Acad. Sci. USA 88:10535-10539 (1991); Lesslauer et al., Eur. J. Immunol. 27:2883-2886 (1991); and Peppel et al., J. Exp. Med. 174:1483-1489 (1991)); and IgE receptor α (Ridgway and Gorman, J. Cell. Biol. Vol. 115, Abstract No. 1448 (1991)).

As discussed elsewhere herein, anti-TCR binding molecules, e.g., antibodies of the invention, or antigen-binding fragments, variants, or derivatives thereof, may be fused heterologous polypeptides to increase the in vivo half-life of the polypeptides or for use in immunoassays using methods known in the art. For example, in one embodiment, PEG can be conjugated to the anti-TCR antibodies of the invention to increase their half-life in vivo. See Leong et al., Cytokine 16:106 (2001); Adv. in Drug Deliv. Rev. 54:531 (2002); or Weir et al., Biochem. Soc. Transactions 30:512 (2002).

Moreover, anti-TCR binding molecules, e.g., antibodies of the invention, or antigen-binding fragments, variants, or derivatives thereof, can be fused to marker sequences, such as a peptide to facilitate their purification or detection. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

Fusion proteins can be prepared using methods that are well known in the art (see for example U.S. Pat. Nos. 5,116,964 and 5,225,538). The precise site at which the fusion is made may be selected empirically to optimize the secretion or binding characteristics of the fusion protein. DNA encoding the fusion protein is then transfected into a host cell for expression.

Anti-TCR binding molecules, e.g., antibodies of the present invention, or antigen-binding fragments, variants, or derivatives thereof, may be used in non-conjugated form or may be conjugated to at least one of a variety of molecules, e.g., to improve the therapeutic properties of the molecule, to facilitate target detection, or for imaging or therapy of the patient. Anti-TCR binding molecules, e.g., antibodies of the invention, or antigen-binding fragments, variants, or derivatives thereof, can be labeled or conjugated either before or after purification, or when purification is performed.

In particular, anti-TCR antibodies of the invention, or antigen-binding fragments, variants, or derivatives thereof, may be conjugated to therapeutic agents, prodrugs, peptides, proteins, enzymes, viruses, lipids, biological response modifiers, pharmaceutical agents, or PEG.

Those skilled in the art will appreciate that conjugates may also be assembled using a variety of techniques depending on the selected agent to be conjugated. For example, conjugates with biotin are prepared, e.g., by reacting a binding polypeptide with an activated ester of biotin such as the biotin N-hydroxysuccinimide ester. Similarly, conjugates with a fluorescent marker may be prepared in the presence of a coupling agent, e.g., those listed herein, or by reaction with an isothiocyanate, preferably fluorescein-iso-thiocyanate. Conjugates of the anti-TCR antibodies of the invention, or antigen-binding fragments, variants, or derivatives thereof, are prepared in an analogous manner.

The present invention further encompasses anti-TCR binding molecules, e.g., antibodies of the invention, or antigen-binding fragments, variants, or derivatives thereof, conjugated to a diagnostic or therapeutic agent. The anti-TCR antibodies, including antigen-binding fragments, variants, and derivatives thereof, can be used diagnostically to, for example, monitor the development or progression of a disease as part of a clinical testing procedure to, e.g., determine the efficacy of a given treatment and/or prevention regimen. For example, detection can be facilitated by coupling the anti-TCR antibody, or antigen-binding fragment, variant, or derivative thereof, to a detectable substance. Examples of detectable substances include various enzymes, prosthetic groups, fluorescent materials, luminescent materials, bioluminescent materials, radioactive materials, positron emitting metals using various positron emission topographies, and nonradioactive paramagnetic metal ions. Sec, for example, U.S. Pat. No. 4,741,900 for metal ions which can be conjugated to antibodies for use as diagnostics according to the present invention. Examples of suitable enzymes include horseradish peroxidase, alkaline phosphatase, .beta.-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{111}In$, $^{90}Y$, or $^{99}Tc$.

An anti-TCR binding molecule, e.g., an antibody, or antigen-binding fragment, variant, or derivative thereof, may be conjugated to a therapeutic moiety such as a cytotoxin, a therapeutic agent or a radioactive metal ion. A cytotoxin or cytotoxic agent includes any agent that is detrimental to cells.

An anti-TCR binding molecule, e.g., an antibody, or antigen-binding fragment, variant, or derivative thereof, also can be detectably labeled by coupling it to a reporter, such as a chemiluminescent or fluorescent compound. The presence of the tagged anti-TCR binding molecule is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an anti-TCR antibody, or antigen-binding fragment, variant, or derivative thereof, can be detectably labeled is by linking the same to an enzyme and using the linked product in an enzyme immunoassay (EIA) (Volley, A., "The Enzyme Linked Immunosorbent Assay (ELISA)" Microbiological Associates Quarterly Publication, Walkersville, Md.; Diagnostic Horizons 2:1-7 (1978); Voller et al., J. Clin. Pathol. 31:507-520 (1978); Butler, Meth. Enzymol. 73:482-523 (1981); Maggio, ed. (1980) Enzyme Immunoassay, CRC Press, Boca Raton, Fla.; Ishikawa et al., eds. (1981) Enzyme Immunoassay (Kgaku Shoin, Tokyo). The enzyme, which is bound to the anti-TCR antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the anti-TCR binding molecule, e.g., antibody, or antigen-binding fragment, variant, or derivative thereof, it is possible to detect the binding molecule through the use of a radioimmunoassay (MA) (see, for example, Weintraub (March, 1986) Principles of Radioimmunoassays, Seventh Training Course on Radioligand Assay Techniques (The Endocrine Society), which is incorporated by reference herein). The radioactive isotope can be detected by means including, but not limited to, a gamma counter, a scintillation counter, or autoradiography.

An anti-TCR binding molecule, e.g., antibody, or antigen-binding fragment, variant, or derivative thereof, can also be detectably labeled using fluorescence emitting metals such as 152Eu, or others of the lanthanide series. These metals can be attached to the binding molecule using such metal chelating groups as diethylenetriaminepentacetic acid (DTPA) or ethylenediaminetetraacetic acid (EDTA).

Techniques for conjugating various moieties to an antibody (e.g., an anti-TCR antibody), or antigen-binding fragment, variant, or derivative thereof, are well known, see, e.g., Amon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-56; Hellstrom et al. (1987) "Antibodies for Drug Delivery," in Controlled Drug Delivery, ed. Robinson et al, (2nd ed.; Marcel Dekker, Inc.), pp. 623-53); Thorpe (1985) "Antibody Carriers of Cytotoxic Agents in Cancer Therapy: A Review," in Monoclonal Antibodies '84: Biological and Clinical Applications, ed. Pinchera et al., pp. 475-506; "Analysis, Results, and Future Prospective of the Therapeutic Use of Radiolabeled Antibody in Cancer Therapy," in Monoclonal Antibodies for Cancer Detection and Therapy, ed. Baldwin et al., Academic Press, pp. 303-16 (1985); and Thorpe et al. (1982) "The Preparation and Cytotoxic Properties of Antibody-Toxin Conjug" Immunol. Rev. 62:119-58.

VII. EXPRESSING ANTI-TCR ANTIBODY POLYPEPTIDES

DNA sequences that encode the light and the heavy chains of the antibody may be made, either simultaneously or separately, using reverse transcriptase and DNA polymerase in accordance with well-known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

Following manipulation of the isolated genetic material to provide anti-TCR antibodies, or antigen-binding fragments, variants, or derivatives thereof, of the invention, the polynucleotides encoding the anti-TCR antibodies are typically inserted in an expression vector for introduction into host cells that may be used to produce the desired quantity of anti-TCR antibody.

Recombinant expression of an antibody, or fragment, derivative or analog thereof, e.g., a heavy or light chain of an antibody that binds to a target molecule described herein, e.g., TCR, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods that are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

In particular aspects, the invention provides vectors comprising a polynucleotide encoding the anti-TCR antibodies and antigen binding fragments as disclosed herein. In embodiments, the vectors are viral, non-viral, episomal, or integrating. In embodiments, the vectors are transposons, e.g., sleeping beauty transposons. In embodiments, the vector is a vector comprising lentiviral backbone components. Exemplary backbone components include, but are not limited to, pFUGW, and pSMPUW.

For the purposes of this invention, numerous expression vector systems may be employed. For example, one class of vector utilizes DNA elements that are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells that have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, as well as transcriptional promoters, enhancers, and termination signals.

In particularly preferred embodiments the cloned variable region genes are inserted into an expression vector along with the heavy and light chain constant region genes (preferably human) synthesized as discussed above. Of course, any expression vector that is capable of eliciting expression in eukaryotic cells may be used in the present invention. Examples of suitable vectors include, but are not limited to plasmids pcDNA3, pHCMV/Zeo, pCR3.1, pEF 1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those that express suitably high levels if immunoglobulin heavy and light chains is routine experimentation that can be carried out, for example, by robotic systems.

More generally, once the vector or DNA sequence encoding a monomeric subunit of the anti-TCR antibody has been prepared, the expression vector may be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway (1988) "Mammalian Expression Vectors" in Vectors, ed. Rodriguez and Denhardt (Butterworths, Boston, Mass.), Chapter 24.2, pp. 470-472. Typically, plasmid introduction into the host is via electroporation. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques, and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

"Host cells" refers to cells that harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells that may, when transformed or transfected with the appropriate nucleotide coding sequences, express an antibody molecule of the invention in situ. These include, but are not limited to, microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

The host cell line used for protein expression is often of mammalian origin; those skilled in the art are credited with ability to preferentially determine particular host cell lines that are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, 293, WI38, R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used.

For long-term, high-yield production of recombinant proteins, stable expression is preferred. For example, cell lines that stably express the antibody molecule may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including, but not limited to, the herpes simplex virus thymidine kinase (Wigler et al., Cell 11:223 (1977)), hypoxanthine-guanine phosphoribosyltransferase (Szybalska and Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan and Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshey, Ann. Rev. Pharmacol. Toxicol. 32:573-596 (1993); Mulligan, Science 260: 926-932 (1993); and Morgan and Anderson, Ann. Rev. Biochem. 62:191-217 (1993); TIB TECH 11(5):155-215 (May, 1993); and hygro, which confers resistance to hygromycin (Santerre et al., Gene 30:147 (1984). Methods commonly known in the art of recombinant DNA technology which can be used are described in Ausubel et al. (1993) Current Protocols in Molecular Biology (John Wiley & Sons, NY); Kriegier (1990) "Gene Transfer and Expression" in A Laboratory Manual (Stockton Press, NY); Dracopoli et al. (eds) (1994) Current Protocols in Human Genetics (John Wiley & Sons, NY) Chapters 12 and 13; Colberre-Garapin et al. (1981) J. Mol. Biol. 150:1, which are incorporated by reference herein in their entireties.

The expression levels of an antibody molecule can be increased by vector amplification (for a review, see Bebbington and Hentschel (1987) "The Use of Vectors Based on Gene Amplification for the Expression of Cloned Genes in Mammalian Cells in DNA Cloning" (Academic Press, NY) Vol. 3. When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding anti-TCR antibodies, or antigen-binding fragments, variants, or derivatives thereof of the invention can also be expressed in non-mammalian cells such as insect, bacteria or yeast or plant cells. Bacteria that readily take up nucleic acids include members of the enterobacteriaceae, such as strains of *Escherichia coli* or *Salmonella; Bacillaceae*, such as *Bacillus subtilis; Pneumococcus; Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies (WO 02/096948A2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lacZ coding region so that a fusion protein is produced; ON vectors (Inouye and Inouye, Nucleic Acids Res. 13:3101-3109 (1985); Van Heeke and Schuster, J. Biol. Chem. 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. Saccharomyces cerevisiae, or common baker's yeast, is the most commonly used among eukaryotic microorganisms although a number of other strains are commonly available, e.g., *Pichia pastoris*.

For expression in *Saccharomyces*, the plasmid YRp7, for example, (Stinchcomb et al., Nature 282:39 (1979); Kingsman et al., Gene 7:141 (1979); Tschemper et al., Gene 10:157 (1980)) is commonly used. This plasmid already contains the TRP1 gene, which provides a selection marker for a mutant strain of yeast lacking the ability to grow in tryptophan, for example ATCC No. 44076 or PEP4-1 (Jones, Genetics 85:12 (1977)). The presence of the trp1 lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a preferred method for increasing the affinity of antibodies of the invention is disclosed in U.S. Patent Application Publication No. 2002 0123057 A1.

The invention thus provides a method of manufacturing an antibody or antigen binding fragment thereof comprising: (a) expressing one or more polynucleotide molecule(s) encoding a VL and VH chain of an antibody in a cell; and (b) purifying the antibody from the cell, wherein the antibody specifically binds to a TCRα chain. In embodiments, the antibody or antigen binding fragment thereof selectively binds an epitope of TCRα chain comprising GSTLRG (SEQ ID NO:1).

VIII. METHOD OF SELECTING A TCR-CONTAINING CELL

In a further embodiment, there is provided a method for selecting a cell comprising a T-cell receptor (TCR) comprising: (a) contacting the cell with an antibody that binds to a TCR, wherein the antibody binds to T-cells having a plurality of T-cell epitope specificities; and (b) selecting a cell comprising the TCR based on binding of the antibody. In certain aspects, the antibody: (i) competes for binding of TCR with the 79A, 79A-23, 79A-15, 79A-11 or 79A-13 monoclonal antibody; (ii) binds to T-cells essentially independent of T-cell epitope specificity; (iii) agonizes TCR activity of T-cells; or (iv) stimulates T-cell proliferation.

In some aspects of the methods of selecting a TCR-containing cell, the antibody binds to a TCRα polypeptide. In other aspects, the antibody binds to an epitope of the TCRα polypeptide comprising the sequence GSTLRG (SEQ ID NO: 1). In some aspects, the cell is in vivo. In some aspects, the antibody comprises a reporter and the method comprises selecting cells comprising a TCR by fluorescence-activated cell sorting (FACS). In some aspects, selecting cells comprises selecting using paramagnetic beads. In certain aspects, the antibody is bound to a support. For example, the support is a bead, a surface, a column or host cell. In certain aspects, the method is further defined as a method for purifying or enriching T-cells. In further aspects, contacting the cell with an antibody comprises inducing activation or growth in the cell comprising the TCR. In some aspects, purifying or enriching cells comprising a TCR comprises stimulating proliferation of the cells.

IX. ARTIFICIAL ANTIGEN PRESENTING CELLS (aAPCs)

In some cases, artificial antigen presenting cells ("aAPCs") also referred to as activating and propagating cells (aAPCs) are useful in the expansion, propagation and/or activation of T-cells or T-cell progenitors and in preparing T-cell-based therapeutic compositions and cell therapy products. T-cell therapeutic compositions can include for example, T cells that are genetically modified to include chimeric antigen receptor (CAR), T cell receptors (TCR) or any chimeric receptors.

aAPCs for use according to the embodiments include but are not limited to dendritic cells, macrophages, immortalized cells and artificial antigen presenting cells. In one aspect, the aAPCs may be transgenic K562 cells. In some aspects of the invention, the aAPCs are HLAC negative, and in some aspects of the invention, the aAPCs are HLAC positive. In certain aspects, aAPC are conjugated to an anti-TCR-binding antibody of the embodiments. In further aspects, an aAPC comprises an expression construct for surface expression of an anti-TCR-binding antibody (e.g., a membrane-bound antibody). For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009, each of which is incorporated herein by reference.

The aAPCs may comprise additional molecules that activate or co-stimulate T-cells in some cases. The additional molecules may, in some cases, comprise membrane-bound Cy cytokines. In yet still further aspects, the aAPCs are inactivated or irradiated, or have been tested for and confirmed to be free of infectious material. In still further aspects, culturing the cells in the presence of aAPCs comprises culturing the cells in a medium comprising soluble cytokines, such as IL-15, IL-21 and/or IL-2. The cells may be cultured at a ratio of about 10:1 to about 1:10; about 3:1 to about 1:5; about 1:1 to about 1:3 (immune effector cells to aAPCs); or any range derivable therein. For example, the co-culture of T cells and aAPCs can be at a ratio of about 1:1, about 1:2 or about 1:3. In some aspects, ex vivo culturing the genetically modified T cells or T cells, is for no more than 14 days, no more than 7 days or no more than 3 days. In other aspects, the genetically modified T cells or T cells are cultured ex vivo for less than 21 days, such as for less than 18, 17, 16, 15, 14, 13, 12, 1 1, 10, 9, 8, 7, 6, 5, 4, 3, 2 days, 1 day or less.

For example, the ex vivo culture (e.g., culture in the presence of AaPCs or aAPCs) can be performed for less than one population doubling of the T cells. In still further aspects, the T cells are not cultured ex vivo in the presence of AaPCs or aAPCs.

In one aspect, the aAPCs may express CD137L. In other aspects, the aAPCs may further express CD19, CD64, CD86, or membrane bound IL-15. In some aspects, the membrane-bound IL-15 (mIL-15) comprises a fusion protein between IL-15 and IL-15Ra. In a further aspect, the mIL-15 construct comprises the IL-15 cDNA sequence (NM 000585.4) fused to the full length IL-15Ra (NM 002189.3) with a serine-glycine linker. An IgE signal peptide (gb–AAB59424.1) can be used for the mIL15 fusion construct. An example of mIL-15 is described in WO/2014/186469, herein incorporated by reference.

In embodiments, a truncated CD8 transmembrane protein (tCD8-TM) or truncated human Fc-tCD8-TM domain (with and without HA tag) or similar extracellular scaffolding molecule is fused to an anti-TCR antibody or fragment thereof and expressed on cells, such as derived from K562 along with co-stimulatory ligands C86, CD137L, or IL15 (including as a membrane-bound formulation) or any combination thereof. In aspects of the invention, SEQ ID NO:24 is an example of a human truncated CD8 domain, SEQ ID NO:25 is an example of a human CD8a transmembrane domain, and SEQ ID NO:26 is an example of a hCD8a extracellular domain.

aAPCs may be used to expand and/or activate T cells generally or in a TCR epitope specific manner. During encounter with tumor antigen, the signals delivered to T cells by antigen-presenting cells can affect T-cell programming and their subsequent therapeutic efficacy. This has stimulated efforts to develop artificial antigen-presenting cells that allow optimal control over the signals provided to T cells (Turtle et al., 2010). In addition to antibody, such as TCR-binding antibody, the APC systems may also comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include C86, CD137L and mIL15 or OX40L (CD134L); along with CD70 and B7.1 (also called B7 or CD80), which can bind to CD28, 4-1BB or OX40 molecules on the surface of T cells, thereby affecting, e.g., T-cell expansion, Th1 differentiation, short-term T-cell survival, and cytokine secretion such as interleukin (IL)-2. Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), that promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001, incorporated herein by reference.

In some cases, cells selected to become aAPCs, have deficiencies in intracellular antigen-processing, intracellular peptide trafficking, and/or intracellular MHC Class I or Class II molecule-peptide loading, or are poikilothermic (i.e., less sensitive to temperature challenge than mammalian cell lines), or possess both deficiencies and poikilothermic properties. In some aspects, cells selected to become aAPCs also lack the ability to express at least one endogenous counterpart (e.g., endogenous MHC Class I or Class II molecule and/or endogenous assisting molecules as described above) to the exogenous MHC Class I or Class II molecule and assisting molecule components that are introduced into the cells. Furthermore, aAPCs may retain the deficiencies and poikilothermic properties that were possessed by the cells prior to their modification to generate the aAPCs. Exemplary aAPCs either constitute or are derived from a transporter associated with antigen processing (TAP)-deficient cell line, such as an insect cell line. An exemplary poikilothermic insect cells line is a Drosophila cell line, such as a Schneider 2 cell line (e.g., Schneider, J. m 1972). Illustrative methods for the preparation, growth, and culture of Schneider 2 cells, are provided in U.S. Pat. Nos. 6,225,042, 6,355,479, and 6,362,001, incorporated herein by reference.

aAPCs may be subjected to a freeze-thaw cycle. For example, aAPCs may be frozen by contacting a suitable receptacle containing the aAPCs with an appropriate amount of liquid nitrogen, solid carbon dioxide (dry ice), or similar low-temperature material, such that freezing occurs rapidly. The frozen aAPCs are then thawed, either by removal of the aAPCs from the low-temperature material and exposure to ambient room temperature conditions, or by a facilitated thawing process in which a lukewarm water bath or warm hand is employed to facilitate a shorter thawing time. Additionally, aAPCs may be frozen and stored for an extended period of time prior to thawing. Frozen aAPCs may also be thawed and then lyophilized before further use. Preservatives that might detrimentally impact the freeze-thaw procedures, such as dimethyl sulfoxide (DMSO), polyethylene glycols (PEGs), and other preservatives, may be advantageously absent from media containing aAPCs that undergo the freeze-thaw cycle, or are essentially removed, such as by transfer of aAPCs to media that is essentially devoid of such preservatives.

In other embodiments, xenogenic nucleic acid and nucleic acid endogenous to the aAPCs may be inactivated by crosslinking, so that essentially no cell growth, replication or expression of nucleic acid occurs after the inactivation. For example, aAPCs may be inactivated at a point subsequent to the expression of exogenous MHC and assisting molecules, presentation of such molecules on the surface of the aAPCs, and loading of presented MHC molecules with selected peptide or peptides. Accordingly, such inactivated and selected peptide loaded aAPCs, while rendered essentially incapable of proliferating or replicating, may retain selected peptide presentation function. The crosslinking can also result in APCS that are essentially free of contaminating microorganisms, such as bacteria and viruses, without substantially decreasing the antigen-presenting cell function of the aAPCs. Thus crosslinking can be used to maintain the important APC functions of aAPCs while helping to alleviate concerns about safety of a cell therapy product developed using the aAPCs. For methods related to crosslinking and aAPCs, see for example, U.S. Patent Application Publication No. 20090017000, which is incorporated herein by reference.

X. METHODS OF EXPANDING AND/OR ACTIVATING T CELLS

The invention provides methods of T-cell activation and ex vivo and in vivo propagation to generate T cells. In embodiments concerning ex vivo activation and propagation, the T-cells are clinical grade. In embodiments, the methods activate T cells by αβ-TCR cross-linking using the antibodies or antigen binding fragments of the invention. In embodiments, the T-cell is a peripheral blood mononuclear cell (PBMC). In further embodiments, T cells can include for example, T cells that are genetically modified to include chimeric antigen receptor (CAR), T cell receptors (TCR) or any chimeric receptors. In some aspects, the T cells may also be modified with cytokines that stimulate proliferation and/or survival of T cells. For example, the T cells can comprise membrane-bound versions of IL-7, IL-15 or IL-21. In some aspects, the cytokine is tethered to the membrane by fusion of the cytokine coding sequence with the receptor for the cytokine. For example, a cell can comprise a vector for expression of a IL-15-IL-15Ra fusion protein, see e.g. WO 2014186469, herein incorporated by reference.

In further aspects, the T cells are further modified with a transposase that facilitates integration of a CAR or TCR coding sequence into the genome of the transfected cell. In some aspects, the transposase is provided as DNA expression vector. However, in preferred aspects, the transposase is provided as an expressible RNA or a protein such that long-term expression of the transposase does not occur in the transgenic cells. For example, in some aspects, the transposase is provided as an mRNA (e.g., an mRNA comprising a cap and poly-A tail). Any transposase system may be used in accordance with the embodiments. However, in some aspects, the transposase is salmonid-type Tel-like transposase (SB). For example, the transposase can be the so called "Sleeping beauty" transposase, see e.g., U.S. Pat. No. 6,489,458, incorporated herein by reference. In certain aspects, the transposase is an engineered enzyme with increased enzymatic activity. Some specific examples of transposases include, without limitation, SB 10, SB 11, SB 100× transposase (see, e.g., Mates et ah, 2009, incorporated herein by reference) or SB110× tranposase. For example, a method can involve electroporation of cells with a mRNA encoding a SB 10, SB 11, SB100× or SB110× transposase.

Activating T cells, or T cell activation, includes numeric expansion of T cells (i.e., increasing the number of T cells) (also referred to as T cell expansion) as well as stimulating T cells to produce cytokine and to kill specific cells (e.g., tumor antigen presenting cells).

The methods of expanding and/or activating T-cells of the invention can be used in a clinical setting to expand and/or activate the T cell population of a diseased subject, i.e., a subject in need thereof, or to expand and/or activate the T cell population of a donor, i.e., T cells derived from a source other than the diseased subject.

The invention additionally provides methods for expanding and/or activating T-cells comprising contacting the T-cells with artificial antigen presenting cells (aAPCs) in the presence of an antibody or antigen binding fragment thereof that binds to an epitope of a T-cell Receptor (TCR), wherein said epitope is a polypeptide comprising sequence GSTLRG (SEQ ID NO:1). In embodiments, the aAPCs are conjugated to an antibody or antigen-binding fragment thereof that binds to the TCR epitope. In embodiments, the aAPCs comprise an expression construct for expressing an antibody or antigen binding fragment thereof that binds to said epitope of a TCR. In embodiments, the antibody or antigen binding fragment thereof engages αβ-TCR in a conformation specific manner to elicit polyclonal T cell response through recognition via plurality of T-cell epitope specificities.

In the methods of expanding and/or activating T cells, as disclosed herein, in embodiments, the antibody or antigen-binding fragment is an anti-TCR antibody as disclosed herein. For example, the antibody or antigen-binding fragment thereof comprises HCDR1 at least 95% or 100% identical to SEQ ID NO:2; HCDR2 at least 95% identical to SEQ ID NO:3; HCDR3 identical to CAYL (SEQ ID NO:22). In an additional embodiment, the antibody or antigen-binding fragment thereof comprises LCDR1 at least 95% or 100% identical to SEQ ID NO:9; LCDR2 at least 95% or 100% identical to SEQ ID NO:5; LCDR3 at least 95% identical to SEQ ID NO:10. Further, the antibody or antigen-binding fragment thereof comprises HCDR1 at least 95% or 100% identical to SEQ ID NO:2; HCDR2 at least 95% or 100% identical to SEQ ID NO:3; HCDR3 identical to CAYW (SEQ ID NO:23).

In the methods of expanding and/or activating T cells, as disclosed herein, in embodiments, the antibody or antigen-binding fragment is an anti-TCR antibody as disclosed herein. For example, the antibody or antigen-binding fragment thereof comprises LCDR1 at least 95% or 100% identical to SEQ ID NO:9; LCDR2 at least 95% or 100% identical to SEQ ID NO:5; LCDR3 at least 95% or 100% identical to SEQ ID NO:10. In embodiments, the antibody or antigen-binding fragment thereof comprises LCDR1 at least 95% or 100% identical to SEQ ID NO:4; LCDR2 at least 95% or 100% identical to SEQ ID NO:5; LCDR3 at least 95% or 100% identical to SEQ ID NO:10. In additional embodiments, the antibody or antigen-binding fragment thereof comprises HCDR1 at least 95% or 100% identical to SEQ ID NO:15; HCDR2 at least 95% or 100% identical to SEQ ID NO:16; HCDR3 identical to CRYW (SEQ ID NO:17). In further embodiments, the antibody or antigen-binding fragment thereof comprises LCDR1 at least 95% or 100% identical to SEQ ID NO:18; LCDR2 at least 95% or 100% identical to SEQ ID NO:5; LCDR3 at least 95% or 100% identical to SEQ ID NO:6.

In the methods of expanding and/or activating T cells, as disclosed herein, in embodiments, the antibody or antigen-binding fragment is an anti-TCR antibody as disclosed herein. For example, the antibody or antigen binding fragment comprises a VH and VL domain separated by a linker. In embodiments, the antibody or antigen binding fragment further comprises a transmembrane domain (e.g., hCDalpha (SEQ ID NO:25)). In the methods of expanding and/or activating T cells, as disclosed herein, in embodiments, the antibody or antigen-binding fragment is an anti-TCR antibody as disclosed herein. For example, the VH is a polypeptide at least 90% identical to a polypeptide selected from the group consisting of a SEQ ID NO:11, SEQ ID NO:13 and SEQ ID NO:19, and the VL is a polypeptide at least 90% identical to a polypeptide selected from the group consisting of SEQ ID NO:12, SEQ ID NO:14 and SEQ ID NO:20. In embodiments, the VH is a polypeptide at least 90% identical to SEQ ID NO:11 and said VL is a polypeptide at least 90% identical to SEQ ID NO:12. In further embodiments, the VH is a polypeptide at least 90% identical to SEQ ID NO:13 and said VL is a polypeptide at least 90% identical to SEQ ID NO:12. In additional embodiments, the VH is a polypeptide at least 90% identical to SEQ ID NO:11 and said VL is a polypeptide at least 90% identical to SEQ ID NO:14. In a further embodiment, the VH is a polypeptide at least 90% identical to SEQ ID NO:19 and said VL is a polypeptide at least 90% identical to SEQ ID NO:20.

In certain aspects of the invention, stimulation of primary T cells is achieved by using anti-TCR soluble antibodies or antigen binding fragments of the invention in culture. In other aspects, sustained activation is done by engaging the αβ-TCR of T cells via the soluble anti-TCR antibodies or antigen binding fragments of the invention in the presence of T cell growth promoting cytokines such as IL-2, IL-7, IL-15 or IL-21. In other aspects, T cells are numerically expanded by constant engagement of the TCR ligand through a support (such as magnetic beads/polystyrene surface or through cells like irradiated K562 feeder cells). Culture conditions and mode of ligand presentation will vary to impact activation and stimulation leading to T cell numeric expansion.

XI. TREATMENT METHODS USING THERAPEUTIC ANTI-TCR ANTIBODIES

The invention also provides methods of treating an autoimmune disease or a T cell leukemia or T cell lymphoma, or preventing/controlling rejection of an allogeneic graft (bone marrow or solid organ) in an animal in need of treatment, comprising administering to the animal the anti-TCR antibody and/or antigen binding fragment of the invention as a soluble protein, a portion of the antibody, or as a host cell comprising a chimeric antigen receptor (CAR) targeting TCRα polypeptide comprising sequence GSTLRG (SEQ ID NO:1). In embodiments, the host cell is an NK or gamma delta T cell or T cell that has been engineered to prevent expression of endogenous alpha beta TCR.

A CAR is typically composed of an extracellular antibody-derived single-chain variable domain (scFv) for antigen recognition and is joined by a flexible linker connected to a transmembrane domain and an intracellular signaling domain(s) that includes CD3ζ for T-cell activation. Normally when T cells are activated in vivo they receive a primary antigen induced TCR signal with secondary costimulatory signaling from CD28 that induces the production of cytokines (i.e., IL-2 and IL-21), which then feed back into the signaling loop in an autocrine/paracrine fashion. With this in mind, CARs can include CD28 cytoplasmic signaling domain or other costimulatory molecule signaling domains such as 4-1BB signaling domain. Chimeric CD28 co-stimulation improves T-cell persistence by up-regulation of anti-apoptotic molecules and production of IL-2, as well as expanding T cells derived from peripheral blood mononuclear cells (PBMC).

In one embodiment, CARs are fusions of single-chain variable fragments (scFv) derived from monoclonal antibodies fused to transmembrane domain and CD3-zeta endodomain. Such molecules result in the transmission of a zeta signal in response to recognition by the scFv of its target.

In an embodiment, a CAR may have an ectodomain (extracellular), a transmembrane domain and an endodomain (intracellular). In one embodiment of the CAR ectodomain, a signal peptide directs the nascent protein into the endoplasmic reticulum. This is if the receptor is to be glycosylated and anchored in the cell membrane for example. Any eukaryotic signal peptide sequence is envisaged to be functional. Generally, the signal peptide natively attached to the amino-terminal most component is used (e.g. in a scFv with orientation light chain-linker-heavy chain, the native signal of the light-chain is used). Exemplary signal peptides that can be used include signal peptides from immunoglobulin, CD3, CD3ζ, CD8alpha (CD8a) and CD28.

The antigen recognition domain may be a scFv. There may however be alternatives. An antigen recognition domain from native T-cell receptor (TCR) alpha and beta single chains are envisaged, as they have simple ectodomains (e.g. CD4 ectodomain to recognize HIV infected cells) and as well as other recognition components such as a linked e.g., cytokine (which leads to recognition of cells bearing the cytokine receptor). Almost anything that binds a given target with high affinity can be used as an antigen recognition region. In further aspects, the scFvs can be derived from SEQ ID NOs: 7, 11, 13, 19, 20, 8, 12, 14, 19 and/or 20. In further aspects, the sFcvs comprise SEQ ID NOs: 7 and 8; SEQ ID NOs: 11 and 12; SEQ ID NOs:13 and 14; or SEQ ID NOs:19 and 20, in each case optionally separated by a linker. In yet further aspects, the scFvs include SEQ ID NOs: 2, 3, 21, 4, 5, and/or 6; SEQ ID NOs: 2, 3, 22, 9, 5 and/or 10; SEQ ID NOs: 2, 3, 23, 9, 5 and/or 10; SEQ ID NOs: 2, 3, 22, 4, 5 and/or 10; or SEQ ID NOs: 15, 16, 17, 18, 5 and/or 6.

In general, CARs exist in a dimerized form and are expressed as a fusion protein that links the extracellular scFv (VH linked to VL) region, a stalk domain, a transmembrane domain, and intracellular signaling motifs. The endodomain of the first generation CAR induces T cell activation solely through CD3-ζ signaling. The second generation CAR provides activation signaling through CD3-ζ and CD28, or other endodomains such as 4-1BB or OX40. The 3rd generation CAR activates T cells via a CD3-ζ-containing combination of three signaling motifs such as CD28, 4-1BB, or OX40.

In embodiments, between the extracellular domain and the transmembrane domain of the CAR, there is incorporated a stalk domain. As used herein, the term "stalk domain" generally means any oligonucleotide- or polypeptide that functions to link the transmembrane domain to, either the scFv or, the cytoplasmic domain in the polypeptide chain. A stalk domain can include a flexible hinge such as a Fc hinge and optionally one or two constant domains of Fc.

In aspects of the invention, the sequence of the anti-TCR antibody or antigen binding fragment thereof is used to redirect the specificity or binding of an immune cell. For example, the antigen-binding sequence of the anti-TCR antibody or antigen binding fragment of the invention is used to create a membrane-bound protein which when expressed on an immune cell can be used to redirect the specificity or binding of said immune cell.

In additional embodiments, the invention provides methods of treating disease, such as cancer or infection by a pathogen in an animal in need of treatment, comprising administering to the animal a multi-specific T cell engager comprising (a) an antibody or antigen binding fragment thereof targeting a TCRα polypeptide comprising sequence GSTLRG (SEQ ID NO:1), and (b) at least one antibody or antigen binding fragment thereof targeting a tumor associated antigen. An exemplary antibody or antigen binding fragment thereof targeting a TCRα polypeptide comprising sequence GSTLRG (SEQ ID NO:1) is an scFv. An exemplary antibody or antigen binding fragment thereof targeting a tumor associated antigen is an scFv. An exemplary multi-specific T cell engager is a bispecific T cell engager comprising an scFv targeting the TCRα polypeptide and an scFv targeting a tumor associated antigen. A trispecific T cell engager, for example, comprises an scFv targeting the TCRα polypeptide and a first and second scFv targeting tumor associated antigens. In further aspects, the scFv targeting the TCRα polypeptide in this embodiment comprises SEQ ID NOs: 7, 8, 11, 12, 13, 14, 19, and/or 20. In further aspects, the scFv comprises SEQ ID NOs: 7 and 8; SEQ ID NOs: 11 and 12; SEQ ID NOs: 13 and 14; or SEQ ID NOs: 19 and 20, in each case the sequences are optionally separated by a linker. In yet further aspects, the scFvs comprise SEQ ID NOs: 2, 3, 21, 4, 5, and/or 6; SEQ ID NOs: 2, 3, 22, 9, 5 and/or 10; SEQ ID NOs: 2, 3, 23, 9, 5 and/or 10; SEQ ID NOs: 2, 3, 22, 4, 5 and/or 10; or SEQ ID NOs: 15, 16, 17, 18, 5 and/or 6.

In other embodiments, the exemplary antibody or antigen binding fragment thereof targeting a TCRα polypeptide comprising sequence GSTLRG (SEQ ID NO:1) may be combined with other scFvs or proteins that bind tumor antigen to create a soluble recombinant "binder". Upon engaging tumor, the binder can activate T cells by cross-linking TCR to activate T cells for effector functions such as proliferation, cytokine production and killing.

In the treatment methods of the invention, in certain aspects, the animal in need of treatment is a human.

In certain embodiments, the multi-specific T-cell engager comprises an antibody or antigen binding fragment thereof targeting a tumor associated antigen or a pathogen-specific antigen binding domain including carbohydrate antigen recognized by pattern-recognition receptors, such as Dectin-1. A tumor associated antigen may be of any kind so long as it is expressed on the cell surface of tumor cells. Exemplary embodiments of tumor associated antigens include CD19, CD20, carcinoembryonic antigen, alphafetoprotein, CA-125, MUC-1, CD56, EGFR, c-Met, AKT, Her2, Her3, epithelial tumor antigen, melanoma-associated antigen, mutated p53, mutated ras, and so forth.

In certain embodiments intracellular tumor associated antigens may be targeted, such as HA-1, survivin, WT1, and p53. This can be achieved by a scFv expressed on a universal T cell that recognizes the processed peptide described from the intracellular tumor associated antigen in the context of HLA. In addition, the universal T cell may be genetically modified to express a T-cell receptor pairing that recognizes the intracellular processed tumor associated antigen in the context of HLA. In certain embodiments, the T cell can be co-expressed with a membrane-bound cytokine to improve persistence when there is a low amount of tumor-associated antigen. For example, CAR can be co-expressed with membrane-bound IL-15.

In embodiments, the anti-TCR antibodies and antigen binding fragments of the invention suppress the immune system in a subject in need thereof in vivo, for example by over-activating T cells, leading to the loss of T cells and immune-suppression. For instance, organ, bone marrow and stem cell transplantation can improve quality of life and prolong survival. However, rejection of transplanted tissues requires suppression of the immune system by various means. The invention therefore provides methods of suppressing the immune system comprising administering to a patient in need thereof an anti-TCR antibody or antigen binding fragment thereof. In embodiments, the anti-TCR antibody or antigen binding fragment thereof of the invention is administered to a patient in need thereof via intravenous (IV) injection once per day, twice a day or three times a day for 2 to 21 days at a dosage of 1 to 20 mg per day. In embodiments, anti-TCR antibody or antigen binding fragment thereof of the invention is administered to a patient in need thereof via IV injection once per day for 5 to 15 days at a dosage of 5 to 10 mg/day. In embodiments, anti-TCR antibody or antigen binding fragment thereof of the invention is administered to a patient in need thereof via IV injection once per day for 10 to 14 days at a dosage of 5 mg/day.

In additional embodiments, the anti-TCR antibodies and antigen binding fragments of the invention are administered to a subject in need thereof in a therapeutic method to activate T cells in vivo, and/or for in vivo effector functions, such as antibody-dependent cellular cytotoxicity (ADCC) and complement-dependent cytotoxicity (CDC). In embodiments, the anti-TCR antibody or antigen binding fragment thereof of the invention is administered to a patient in need thereof via intravenous (IV) injection once per day, twice a day or three times a day for 2 to 21 days at a dosage of 1 to 20 mg per day. In embodiments, anti-TCR antibody or antigen binding fragment thereof of the invention is administered to a patient in need thereof via IV injection once per day for 5 to 15 days at a dosage of 5 to 10 mg/day. In embodiments, anti-TCR antibody or antigen binding fragment thereof of the invention is administered to a patient in need thereof via IV injection once per day for 10 to 14 days at a dosage of 5 mg/day.

XII. PHARMACEUTICAL COMPOSITIONS AND ADMINISTRATION METHODS

Methods of preparing and administering the anti-TCR binding molecule, e.g., antibodies, or antigen-binding fragments, variants, or derivatives thereof, of the invention to a subject in need thereof are well known to or are readily determined by those skilled in the art. The route of administration of the anti-TCR binding molecule, e.g, antibody, or antigen-binding fragment, variant, or derivative thereof, may be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as being within the scope of the invention, an example of a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, anti-TCR binding molecules, e.g., antibodies, or antigen-binding fragments, variants, or derivatives thereof of the invention can be delivered directly to the site of the adverse cellular population thereby increasing the exposure of the diseased tissue to the therapeutic agent.

As discussed herein, anti-TCR binding molecules, e.g., antibodies, or antigen-binding fragments, variants, or derivatives thereof of the invention may be administered in a pharmaceutically effective amount for the in vivo treatment of TCR-expressing cell-mediated diseases such as certain types of cancers, autoimmune diseases, inflammatory diseases including central nervous system (CNS) and peripheral nervous system (PNS) inflammatory diseases, and invasive angiogenesis. In this regard, it will be appreciated that the disclosed binding molecules of the invention will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of an anti-TCR binding molecule, e.g., an antibody, or antigen-binding fragment, variant, or derivative thereof conjugated or unconjugated, shall be held to mean an amount sufficient to achieve effective binding to a target and to achieve a benefit, e.g., to ameliorate symptoms of a disease or disorder or to detect a substance or a cell.

The pharmaceutical compositions used in this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Preparations for parenteral administration includes sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. In the subject invention, pharmaceutically acceptable carriers include, but are not limited to, 0.01-0.1 M and preferably 0.05 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences (Mack Publishing Co.) 16th ed. (1980).

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an anti-TCR antibody, or antigen-binding fragment, variant, or derivative thereof, by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in U.S. Publ. No. 2002/0102208. Such articles of manufacture will preferably have labels or package inserts indicating that the associated compositions are useful for treating a subject suffering from, or predisposed to a disease or disorder.

Parenteral formulations may be a single bolus dose, an infusion or a loading bolus dose followed with a maintenance dose. These compositions may be administered at specific fixed or variable intervals, e.g., once a day, or on an "as needed" basis.

Certain pharmaceutical compositions used in this invention may be orally administered in an acceptable dosage form including, e.g., capsules, tablets, aqueous suspensions or solutions. Certain pharmaceutical compositions also may be administered by nasal aerosol or inhalation. Such compositions may be prepared as solutions in saline, employing benzyl alcohol or other suitable preservatives, absorption promoters to enhance bioavailability, and/or other conventional solubilizing or dispersing agents.

The amount of an anti-TCR binding molecule, e.g., antibody, or fragment, variant, or derivative thereof, that may be combined with the carrier materials to produce a single dosage form will vary depending upon the host treated and the particular mode of administration. The composition may be administered as a single dose, multiple doses or over an established period of time in an infusion. Dosage regimens also may be adjusted to provide the optimum desired response (a therapeutic or prophylactic response).

In keeping with the scope of the present disclosure, anti-TCR antibodies, or antigen-binding fragments, variants, or derivatives thereof of the invention may be administered to a human or other animal in accordance with the aforementioned methods of treatment in an amount sufficient to produce a therapeutic effect. The anti-TCR antibodies, or antigen-binding fragments, variants, or derivatives thereof of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of anti-TCR binding molecules, e.g., antibodies, or antigen-binding fragments, variants, or derivatives thereof, of the invention may prove to be particularly effective.

By "therapeutically effective dose or amount" or "effective amount" is intended an amount of anti-TCR binding molecule, e.g., antibody or antigen binding fragment thereof, that when administered brings about a positive therapeutic response with respect to treatment of a patient with a disease to be treated.

Therapeutically effective doses of the compositions of the present invention, for treatment of TCR-expressing cell-mediated diseases such as certain types of cancers, e.g., head and neck, prostate, colon, breast, and lung cancers; autoimmune diseases, e.g., arthritis, multiple sclerosis, inflammatory diseases including central nervous system (CNS) and peripheral nervous system (PNS) inflammatory diseases; and invasive angiogenesis, vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages may be titrated using routine methods known to those of skill in the art to optimize safety and efficacy.

The amount of at least one anti-TCR binding molecule, e.g., antibody or binding fragment thereof, to be administered is readily determined by one of ordinary skill in the art without undue experimentation given the disclosure of the present invention. Factors influencing the mode of administration and the respective amount of at least one anti-TCR binding molecule, e.g., antibody, antigen-binding fragment, variant or derivative thereof include, but are not limited to, the severity of the disease, the history of the disease, and the age, height, weight, health, and physical condition of the individual undergoing therapy. Similarly, the amount of anti-TCR binding molecule, e.g., antibody, or fragment, variant, or derivative thereof, to be administered will be dependent upon the mode of administration and whether the subject will undergo a single dose or multiple doses of this agent.

The present invention also provides for the use of an anti-TCR binding molecule, e.g., an antibody or antigen-binding fragment, variant, or derivative thereof, in the manufacture of a medicament for treating an autoimmune disease and/or inflammatory disease, including, e.g., arthritis, multiple sclerosis, CNS and PNS inflammatory diseases, or a cancer.

The invention also provides for the use of an anti-TCR binding molecule, e.g., antibody of the invention, or antigen-binding fragment, variant, or derivative thereof, in the manufacture of a medicament for treating a subject for treating an autoimmune disease and/or inflammatory disease, or for treating a cancer, wherein the medicament is used in a subject that has been pretreated with at least one other therapy. By "pretreated" or "pretreatment" is intended the subject has received one or more other therapies (e.g., been treated with at least one other cancer therapy) prior to receiving the medicament comprising the anti-TCR binding molecule, e.g., antibody or antigen-binding fragment, variant, or derivative thereof, "Pretreated" or "pretreatment" includes subjects that have been treated with at least one other therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the anti-TCR binding molecule, for example, the monoclonal antibody disclosed herein, or antigen-binding fragment, variant, or derivative thereof. It is not necessary that the subject was a responder to pretreatment with the prior therapy or therapies. Thus, the subject that receives the medicament comprising the anti-TCR binding molecule, e.g., an antibody or antigen-binding fragment, variant, or derivative thereof could have responded, or could have failed to respond (e.g., the cancer was refractory), to pretreatment with the prior therapy, or to one or more of the prior therapies where pretreatment comprised multiple therapies. Examples of other cancer therapies for which a subject can have received pretreatment prior to receiving the medicament comprising the anti-TCR binding molecule, e.g., antibody or antigen-binding fragment, variant, or derivative thereof include, but are not limited to, surgery; radiation therapy; chemotherapy, optionally in combination with autologous bone marrow transplant, where suitable chemotherapeutic agents include, but are not limited to, those listed herein above; other anti-cancer monoclonal antibody therapy; small molecule-based cancer therapy, including, but not limited to, the small molecules listed herein above; vaccine/immunotherapy-based cancer therapies; steroid therapy; other cancer therapy; or any combination thereof. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683, 195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods ID Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods ID Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (WIT. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunnology (4th ed.; H. Freemand & Co.); Roitt et al, (2001) Immunology (6th ed.; London: Mosby); Abbas et al, (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

III. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Ex-Vivo Generation of T Cells and Analysis

Hybridoma—CD1D knockout mice were immunized with mouse L-fibroblast cells expressing fusion protein encoding TCR invariant chain (ICVVSDRGSTLGRL) fused to mCD8a. Hybridoma clones were generated via standard cell fusion method using PEG-1500. Antibody clones specific to invariant chain epitope were selected after screening on L-cells expressing the immunogen. Positive binders were verified with synthetic peptides representing the immunogen by indirect ELISA coated with 100 ng of free peptides (FIG. 1A). A best binder 79A with highest OD450 was chosen for further analysis.

Antibody Generation and characterization—A monoclonal antibody (Clone 79A) with narrow linear epitope specificity towards TCRVa24-Ja18 junction (Amino acid Sequence: GSTLGR (SEQ ID NO:1)) but no apparent conformation specificity towards TCRα-CDR3 α-chain was chosen for antibody modeling and affinity improvement. Specificity of antibody clone 79A was checked by ELISA on linear peptides, confirmed on an ala-peptide library and also by flow cytometry analysis (FIGS. 1B-1D).

Figure 1B:
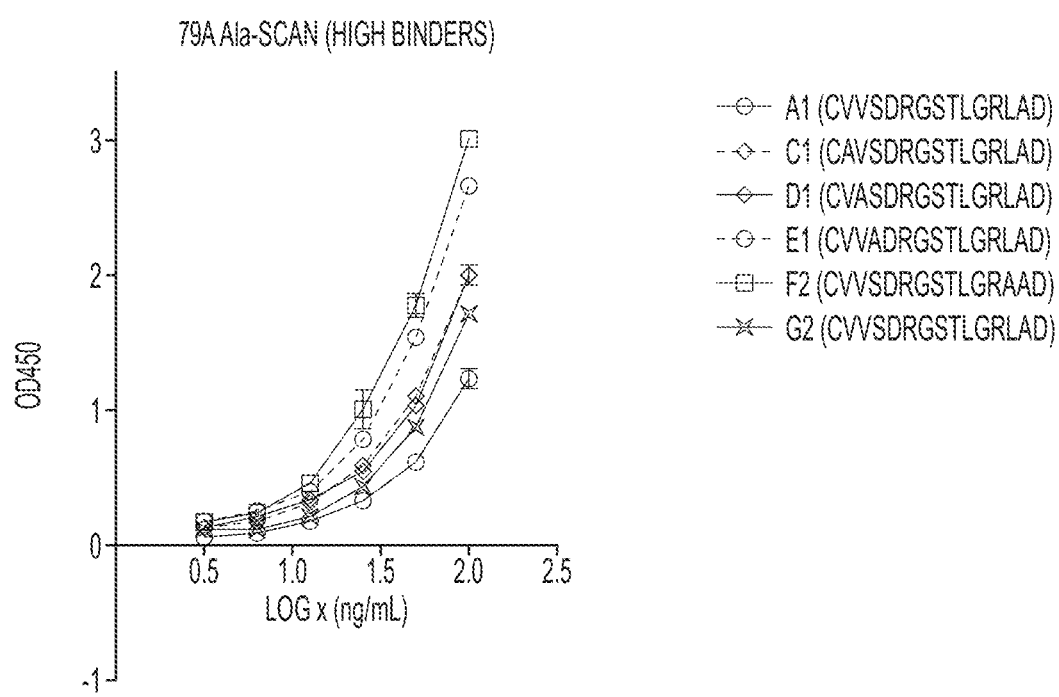
Figure 1C:
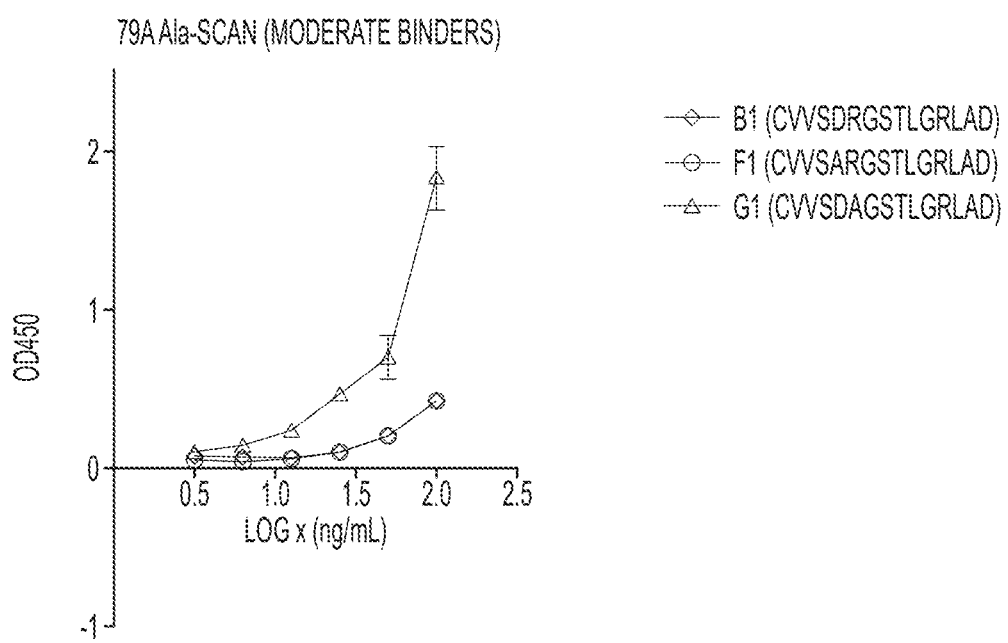
Figure 1D:
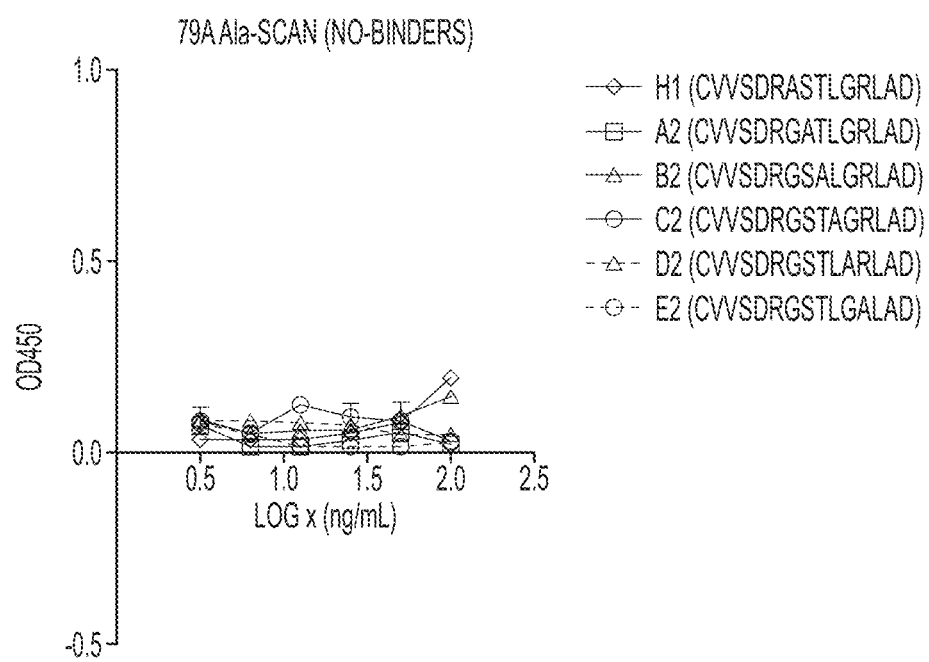
Figure 1E:
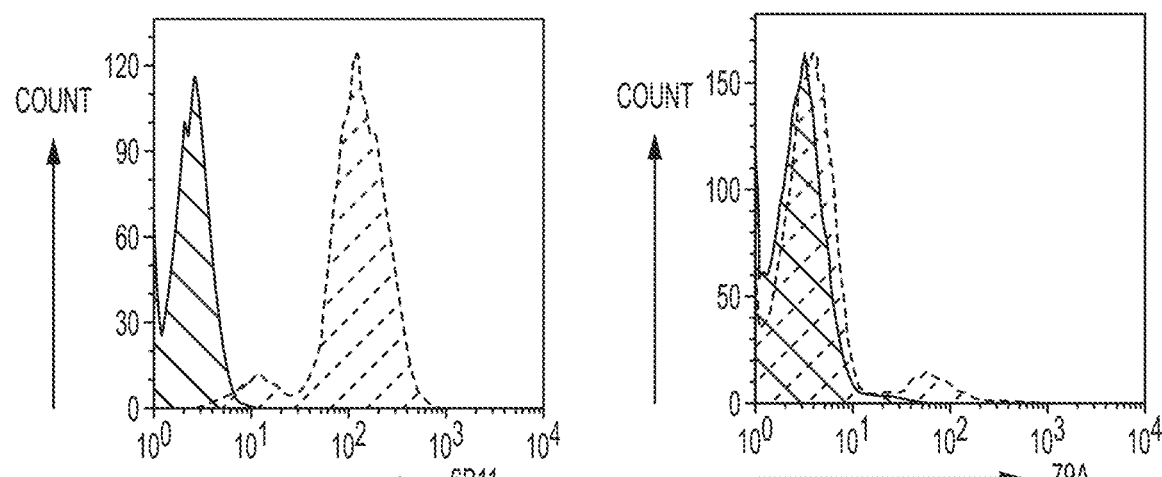

Binding Assay—Binding Assay was Performed on Solid Phase ELISA coated with linear peptides sequence spanning Va24-Ja18 regions (FIG. 1B). Flow cytometry was carried out on PBMC derived live CD3+ T cells using 79A or mutant antibody as primary antibody and matched fluorescent conjugated secondary antibody (either anti-mouse Fab PE or anti-human gamma Fc PE goat Fab polyclonal) for detection (FIG. 1E). Western blot was done on denatured proteins isolated from whole cell lysis (either PBMC, T Cells) resolved on SDS-PAGE.

Figure 2:
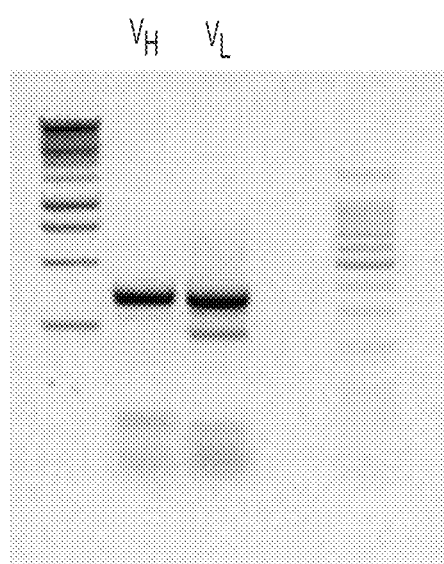
FIG. 2. V-gene amplification of mAb clone 79A. Agarose gel image showing amplification of VH and VL chain of hybridoma clone A79. VH chain (400~bp) shown in image after amplification using a mixture of mouse heavy chain constant region primes (MH-IgG$_1$) along with mouse heavy chain FR1 region primers (contains a mixture of high and low degeneracy), and VL chain (370~bp) after amplification using mixture of mouse kappa chain universal degeneracy primers and kappa-chain constant primers. All 5' primer designed both for VL and VH starting at first nucleotide of FR1.

V-gene amplification and scFv generation—Clone 79A specific to linear epitope GSTLGR (SEQ ID NO:1) was chosen for scFv generation. Antibody V-genes were amplified from 79A cDNA by PCR involving standard mix of degenerate primers of murine VH FR1 for the 5' primers and Ig constant regions for 3' primers (FIG. 2) (Wang, Z., Raifu, M., Howard, M., Smith, L., Hansen, D., Goldsby, R. and Ratner, D. (2000) Universal PCR amplification of mouse immunoglobulin gene variable regions: the design of degenerate primers and an assessment of the effect of DNA polymerase 3' to 5' exonuclease activity. Journal of immunological methods, 233, 167-177). Correct size of VH/VL amplicons were verified by agarose gel electrophoresis. PCR amplified V-gene products were excised from agarose gel, purified by gel purification kit (Qiagen) and the PCR product was cloned into TOPO vector as per manufacturer's instructions. Sequencing for antibody genes was done by Sanger sequencing methods using either T3/T7 or M13F, M13R primers (MD Anderson DNA Sequencing Core). At least 4 clones were used to obtain the consensus sequence of VH and VL on a NCBI BLAST. Antibody CDRs were identified by using consensus VH or VL sequences analyzed with help of IMGT/V-Quest software (available on the World Wide Web at imgt.org/IMGT_vquest/vquest). (Giudicelli, V., Chaume, D. and Lefranc, M. P. (2004) IMGT/V-QUEST, an integrated software program for immunoglobulin and T cell receptor V-J and V-D-J rearrangement analysis. Nucleic acids research, 32, W435-440) CDR positions were further confirmed by another software named V-Base (available on the World Wide Web at vbase2.org).

Figure 3A:
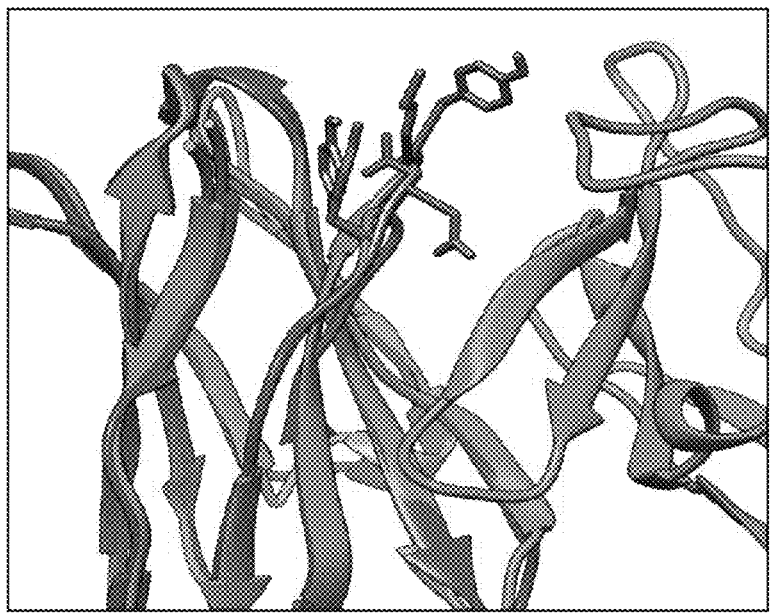
FIGS. 3A-3D. A-B) Antibody (79A) homology model. Construction of 79A homology model based on ABR analyzed by Paratome server (Ref. Kunik, V., Peters, B. and Ofran, Y. (2012) Structural consensus among antibodies defines the antigen binding site. PLoS computational biology, 8, e1002388.) (Kunik et al., 2012. Nucleic Acid Research. 40, W521-524). WAM server (on the World Wide Web at antibody.bath.ac.uk) was used to build VL chain and SWISS-MODEL (on the World Wide Web at swissmodel-.expasy.org) was used to build VH domain because of short VH-Chain CDR. Parameters are as per server specification. C) Z-Docking model of 79A with TCR invariant chain specific peptide. Docked model shows 79A do not induce conformation specific fit with TCR-invariant chain specific peptide derived from 2CDE. D) Docking model showing 79A antibody in complex with αβ-TCR (PDB code 1KGC) built on web server ZDOCK and output was obtained through BuildModel function. Docked model was analyzed by FoldX. Ala-Scan was performed to delineate energy contribution of individual amino acids in the antibody CDR. Total change in interaction energy (ΔΔG) was calculated by subtracting interaction energy of the wildtype from interaction energy of the mutants.
Figure 3B:
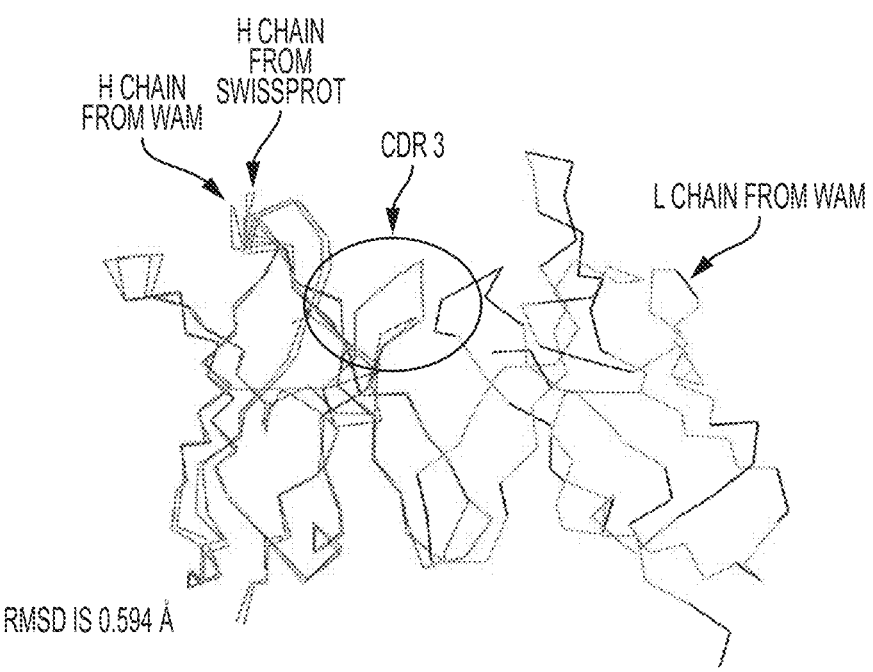
Figure 3C:
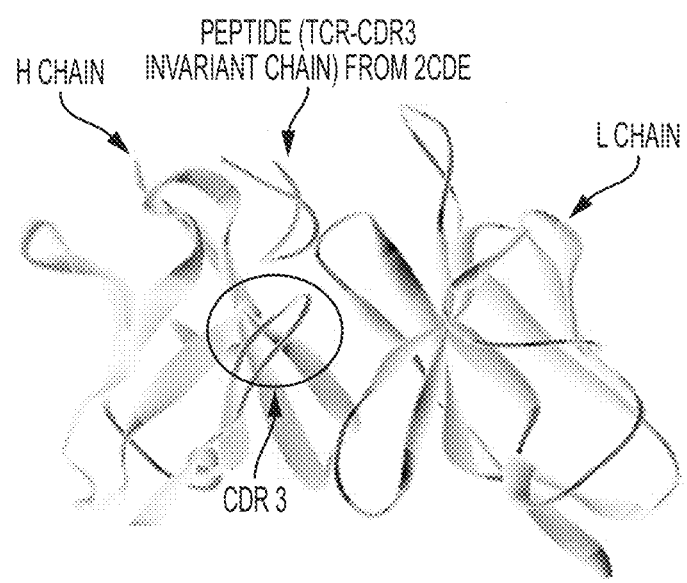
Figure 3D:
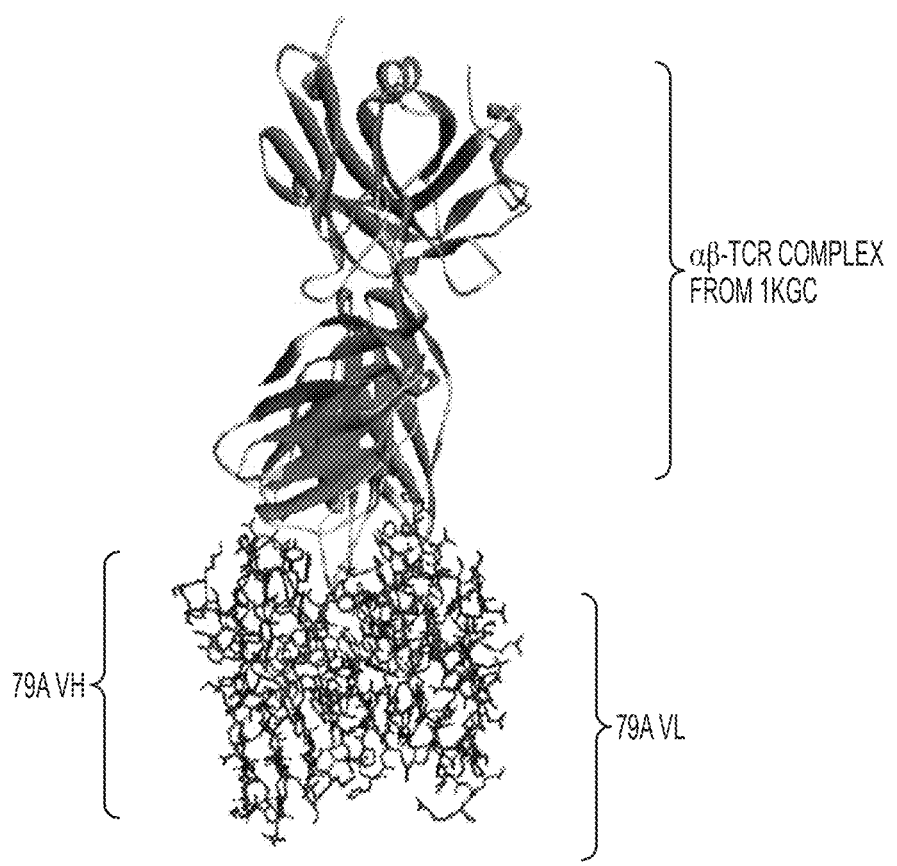

Molecular modeling and docking—Antibody homology modeling and docking was used to study the energetic contribution of residues in antibody (79A) CDRs with linear epitope specificity towards TCR-alpha chain invariant region. 79A scFv sequences were subjected to ABR analysis by Paratome server (FIG. 3A) and confirmed for correct positioning of CDR residues in the VH and VL region. Antibody homology models were developed by WAM server (Whitelegg, N. R. and Rees, A. R. (2000) WAM: an improved algorithm for modelling antibodies on the WEB. Protein engineering, 13, 819-824) and SWISS-Models (FIG. 3B). SWISS-MODEL (Biasini, M., Bienert, S., Waterhouse, A., Arnold, K., Studer, G., Schmidt, T., Kiefer, F., Cassarino, T. G., Bertoni, M., Bordoli, L. et al. (2014) SWISS-MODEL: modelling protein tertiary and quaternary structure using evolutionary information. Nucleic acids research, 42, W252-258) was adapted to build $V_H$ domain as A79 contains a very short CDR3 in its heavy chain. Quality of the final antibody model structure was checked with PROCHECK. 79A and TCR-models (PDB source) were used on ZDOCK server to make a docking model (FIG. 3A, 3B, 3C). In the model percent amino acid residues located in the most favored or generous regions of the Ramachandran plot was 99.4%. Docking model of A79 and TCR [Protein Data Bank (PDB) ID code 1KGC4] was built on ZDOCK server (FIG. 3D). Pierce, B. G., Wiehe, K., Hwang, H., Kim, B. H., Vreven, T. and Weng, Z. (2014) ZDOCK server: interactive docking prediction of protein-protein complexes and symmetric multimers. Bioinformatics (Oxford, England), 30, 1771-1773. For the analysis of docked model, Fold X empirical force field was applied. Complex "Ala scan" function of Fold X was used to identify amino acid residues that could potentially be mutated to increase binding affinity. Mutated A79 models were generated using the "Build Model" function. Change in interaction energy ($\Delta\Delta G$) was calculated as *($\Delta G=\Delta GMU-\Delta GWT$) and then used to define energy contribution of relevant AA (in the CDRs of antibody binding region) towards cognate receptor. The total energy was defined as the binding energy of mutant minus the binding energy of wild type.

Figure 4A:
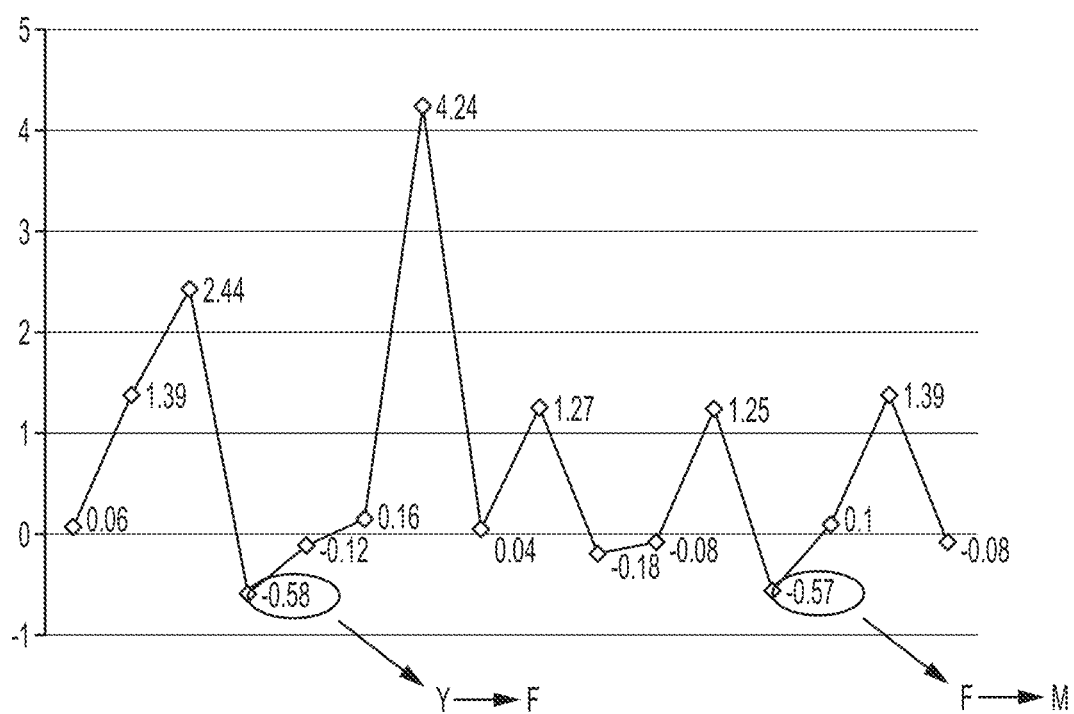
FIGS. 4A-4C. Change in interaction energy (ΔΔG) based on FoldX's complex Ala-scan function. (*ΔΔG=ΔGMU−ΔGWT (−9.98)) Total interaction energy (ΔΔG) obtained from antibody docked model after Ala-scanning. ΔΔG* was calculated by subtracting interaction energy of wild type from that of mutants. Red circle indicates lowest change in interaction energy and residues suitable for mutation. A) Tyrosine (Y) at position 41 of CDR1 of L-chain mutated to Phenylalanine (F). Phenylalanine (F) at position 94 of CDR3 of L-chain changed to Methionine (M). B) Asparitic acid (D) at position 99 of CDR3 of H-chain mutated to Alanine (A). Tryptophan (W) at position 101 of CDR3 of H-chain mutated to Leucine (L). C) Scatter line graph represents distribution of molecular interaction energy ($\Delta\Delta G$) in Kcal/mole along the antibody 79A CDRs (VH and VL regions). Amino acids with low interaction energy (<0.5 Kcal/mol) are considered as candidate for mutation and marked (red arrow). The relevant mutations are Serine to Glycine at position 32 (S32G), Asparagine to Glycine at position 33 (N33G) in 79A light chain CDR1, Aspartic Acid to Glycine at position 31 (D31G) in heavy chain CDR1, Aspartic Acid to Glycine at position 50 (D50G) in heavy chain CDR2 and Aspartic Acid to Arginine at position 99 (D99R) in C Shown in picture pseudocolor plots describing immunophenotype expression of markers in activated T cells harvested at day 7 of co-culture using K562 (parental), K562 S15 with co-stimulation, K562 OKT3 with co-stimulation. H) Ex vivo propagated T cells activated by recombinant antibodies were analyzed for ab-TCR expression and ab-TCR expression shown along with CD3. I) T cell phenotype for CD4 expression before and after activation by antibodies J) T cell phenotype for CD8 expression before and after activation by antibodies K) & L) T cell differentiation markers based on expression of CD45RA and CD45RO to assess level of activation leading to generation of memory or effector memory phenotype. Ex vivo propagated live T cells (fixable viability dye negative) and healthy donor PBMC derived T cells were analyzed by flow cytometry. Cells were stained with CD19 and CD14 to exclude B cells and monocytes. All live cells were gated on CD3+ CD56-negative T cell population. As compared to PBMC derived unmanipulated T-cell population, there appears to be a decrease in CD4+ T cell percentage after OKT3 stimulation while S23 maintains high CD4 composition, in contrast CD8 percentage was highest in OKT3 stimulated group. For cell differentiation, CD45RA negative population was highest in OKT3 group while CD45RA-negative CD45RO positive population remain stable within each group of cells irrespective of antibody clones used for stimulation. (M) Marker for T cell exhaustion PD1 is upregulated in OKT3 stimulated group as compared to S15 or S23 mediated activation.
Figure 4B:
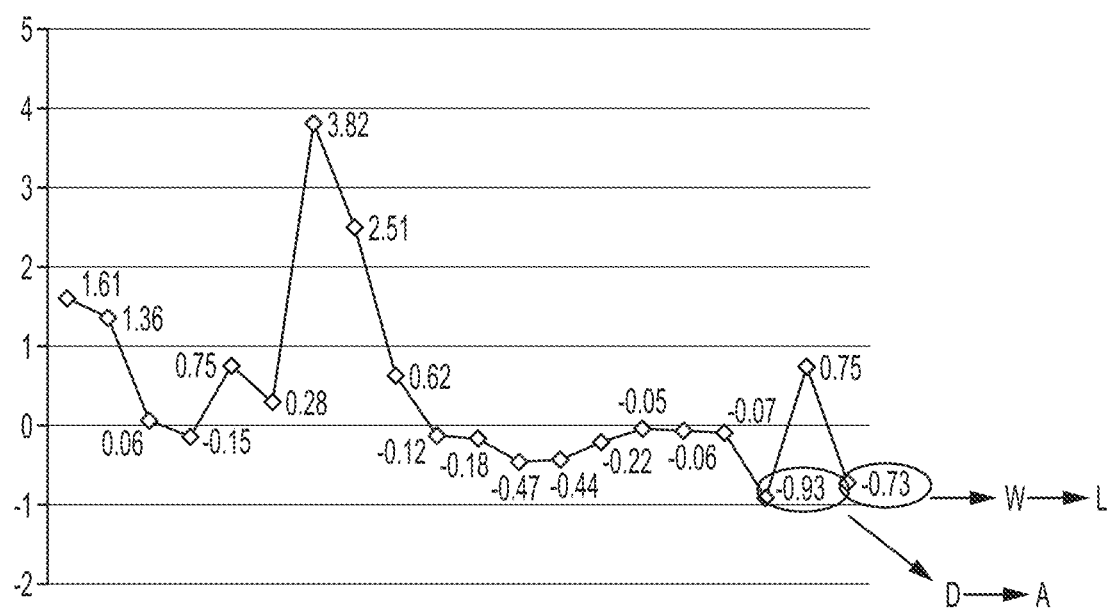
Figure 4C:
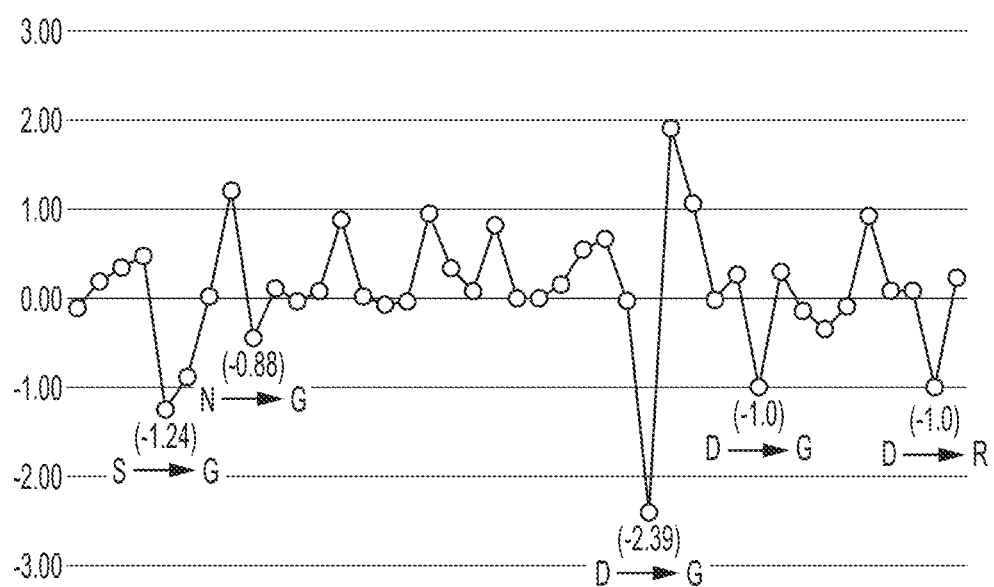

Complex-ALA-Scan function of FoldX software was used to identify potential amino acid (AA) residues for mutation so that affinity enhancement in 79A CDRs towards TCR-alpha chain could be possible (FIGS. 4A, 4C).

Figure 5A:
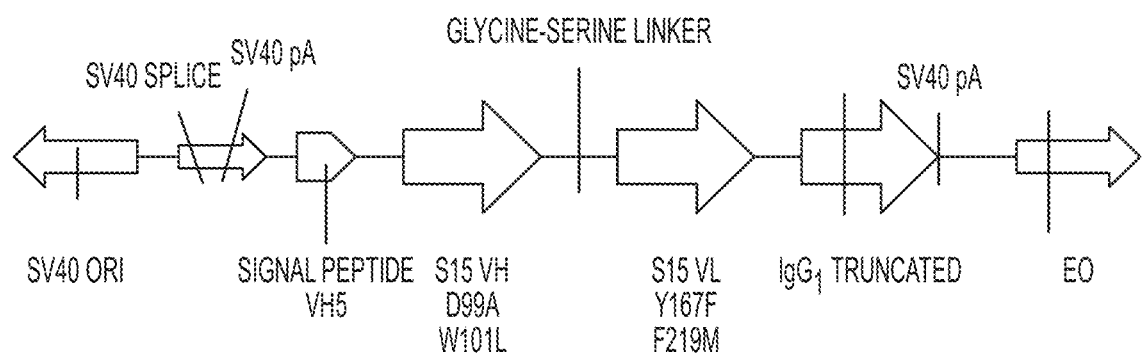
Figure 5B:
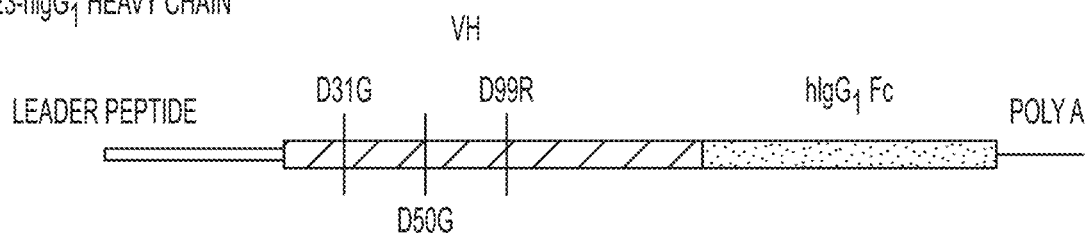
Figure 5B:
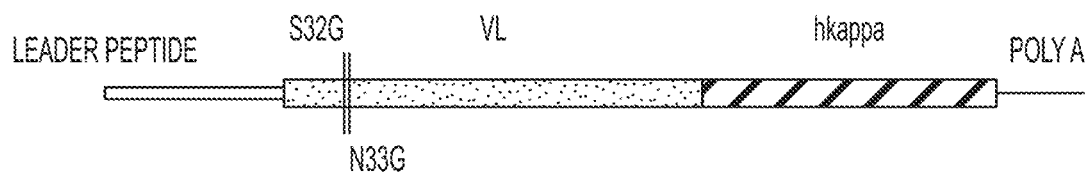

Molecular construct and antibody expression cassette—Schematic of recombinant antibody expression vector (encoding A79 mutant scFv fused to truncated $IgG_1$ Fc), i.e., vector diagram is provided in FIGS. 5A and 5B. In brief, antibody gene expression cassette consists of VH5 signal peptide joined in frame to variable heavy chain (VH-mutant) and variable light chain (VL-mutant). VH and VL are linked by a modified glycine serine G3S sequence to generate A79-scFv. Four such mutants were made (S11, S13, S15 and S23). Out of four mutants two different versions with improved $\Delta\Delta G$ (S15 and S23) were used either as whole IgG or expressed as scFv on K562 cell surface for functionality assays. A79-scFv is then fused in frame with truncated human $IgG_1$-Fc sequence. cDNA representing mutant A79scFv was synthesized de novo as gene string products (Geneart)), then cloned into a plasmid backbone containing SV40 as origin of replication with promoter element ended with SV40 polyA tail. Antibody was expressed as soluble protein in mammalian cells via designated expression plasmid. Secreted antibody was purified from tissue culture supernatant by affinity purification (Protein A) and then dialyzed to PBS (pH 7.2). Recombinant antibody purity was checked on SDS-PAGE, protein concentration was measured by BCA (Thermoscientific). Aliquots of recombinant antibody was stored frozen in −80° C. until use.

Figure 6D:
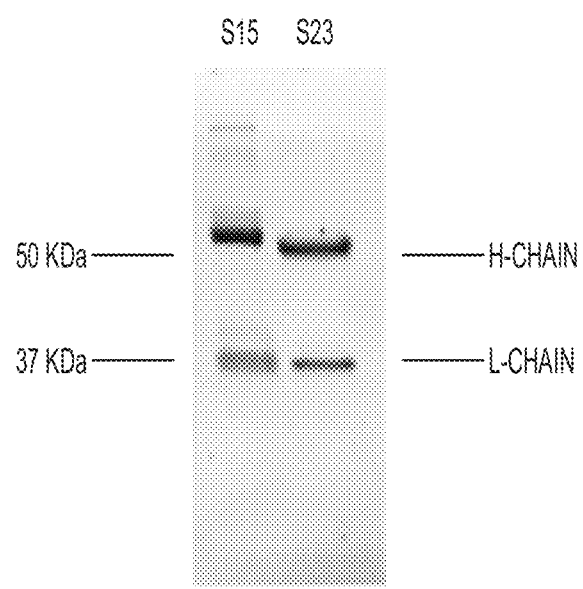
Figure 6E:
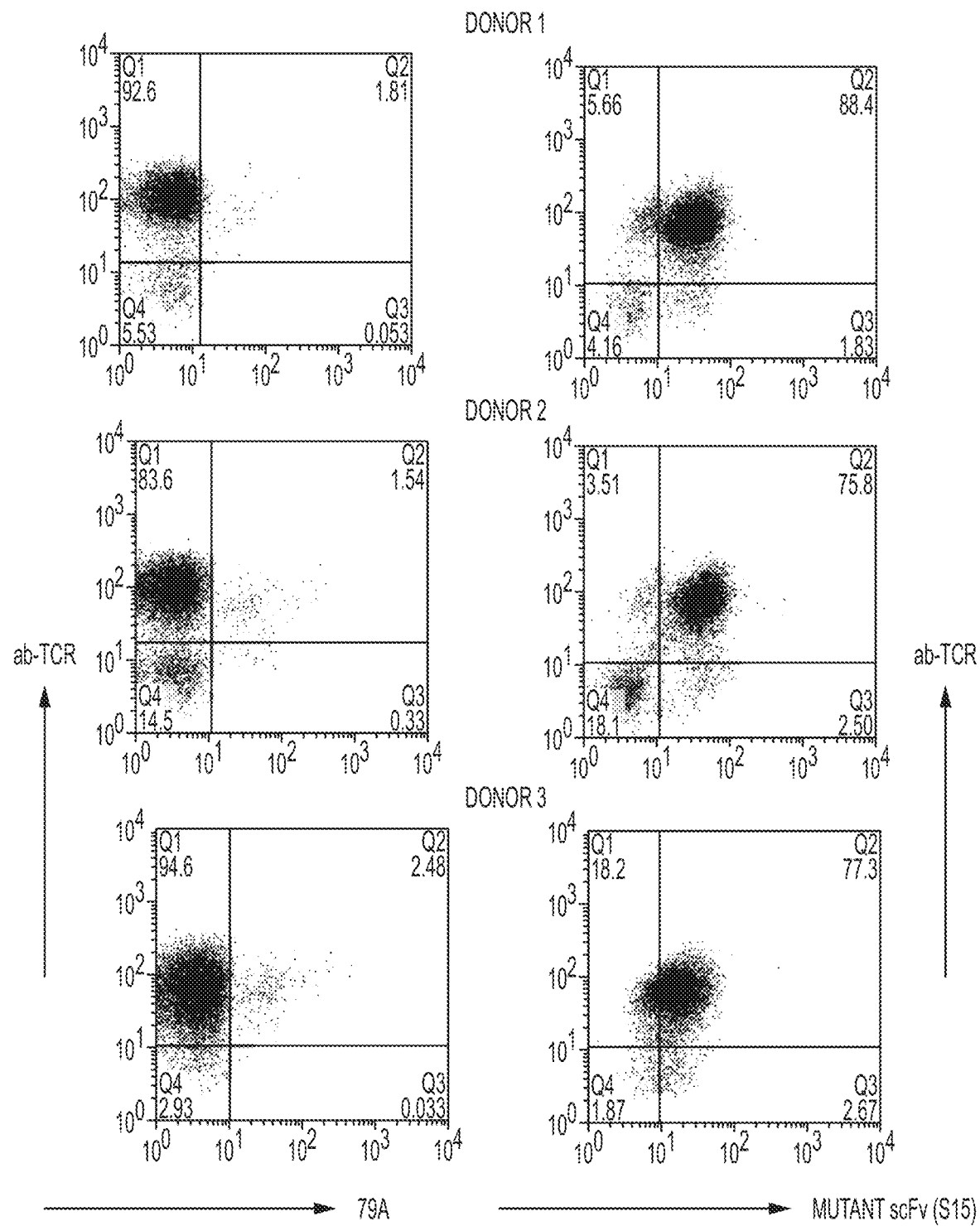

Site directed mutagenesis in 79A CDRs resulted in reformatting a mutant recombinant antibody S15 (Single chain Affinity optimized novel mutant 15) which showed improve affinity and conformation-specific binding to pan-specific TCR alpha chain (FIGS. 6A-6C). Gel electrophoresis image shows homogeneity and purity of recombinant mutant 23 (S23) (FIG. 6D). Additional binding data provided using S15 in FIG. 6E.

Figure 7A:
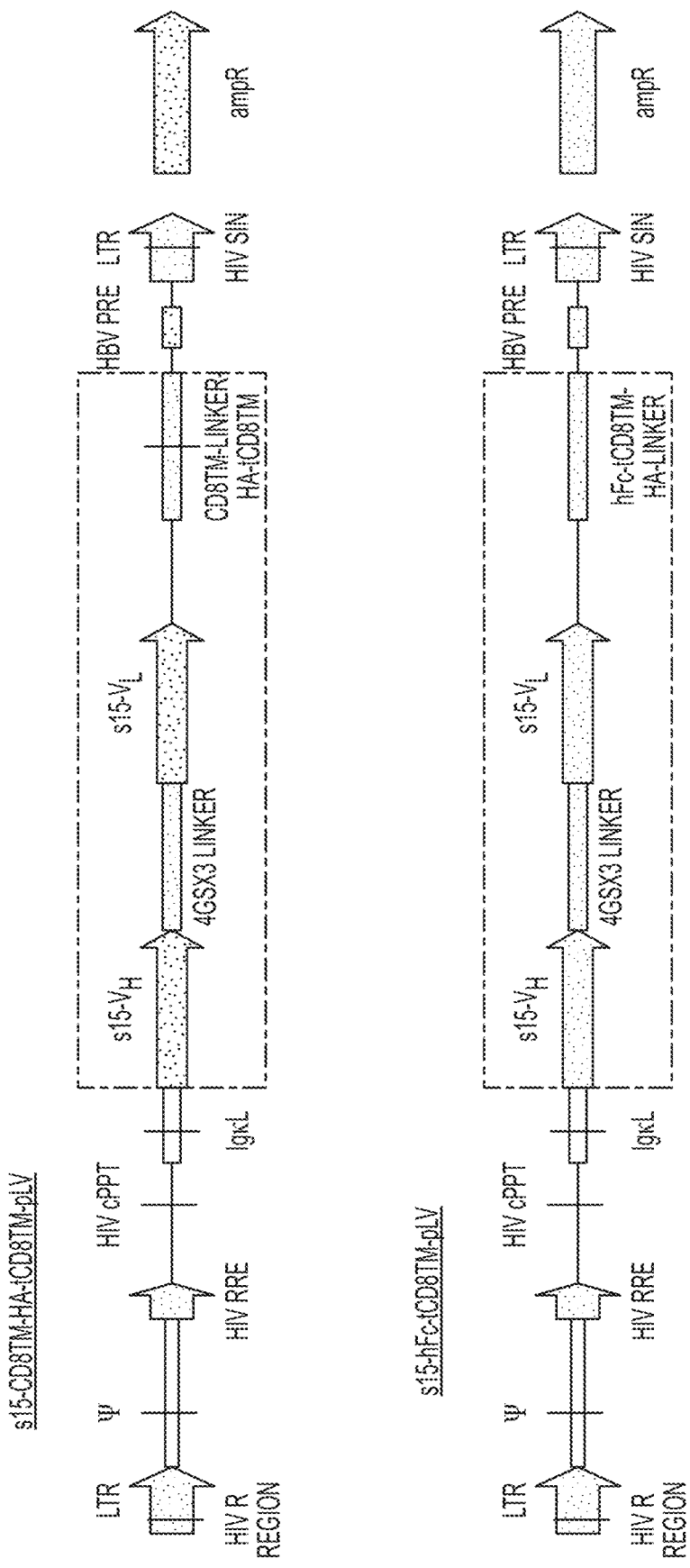
Figure 7B:
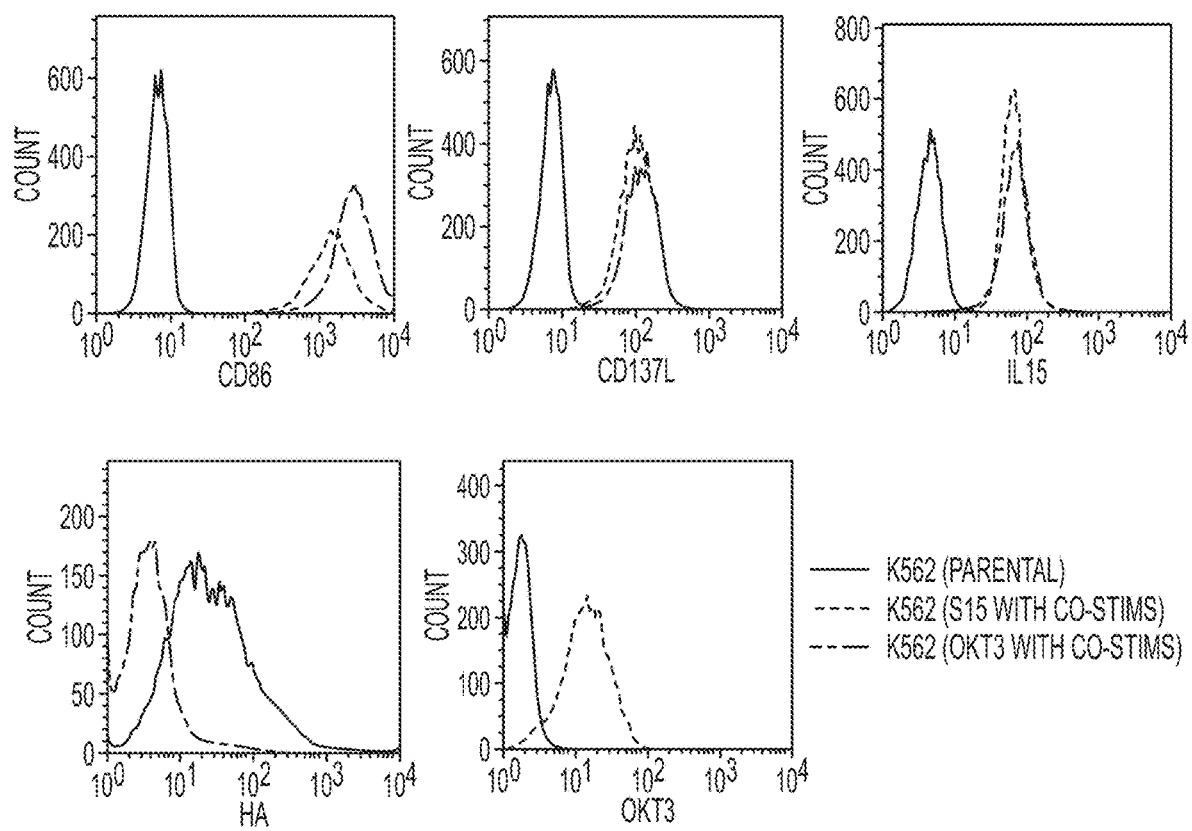

Vector design and surface expression of recombinant antibody S15 on K562 HLAC-cells—S15 sequences were fused either to truncated CD8 transmembrane (tCD8-TM) or truncated human Fc-tCD8-TM domain (with and without HA tag (FIG. 7A)) and expressed on K562C-cells along with co-stimulatory ligands C86, CD137L and IL15-15Ra (FIG. 7B). Vector design and expression was similar for S23 sequences.

Figure 7C:
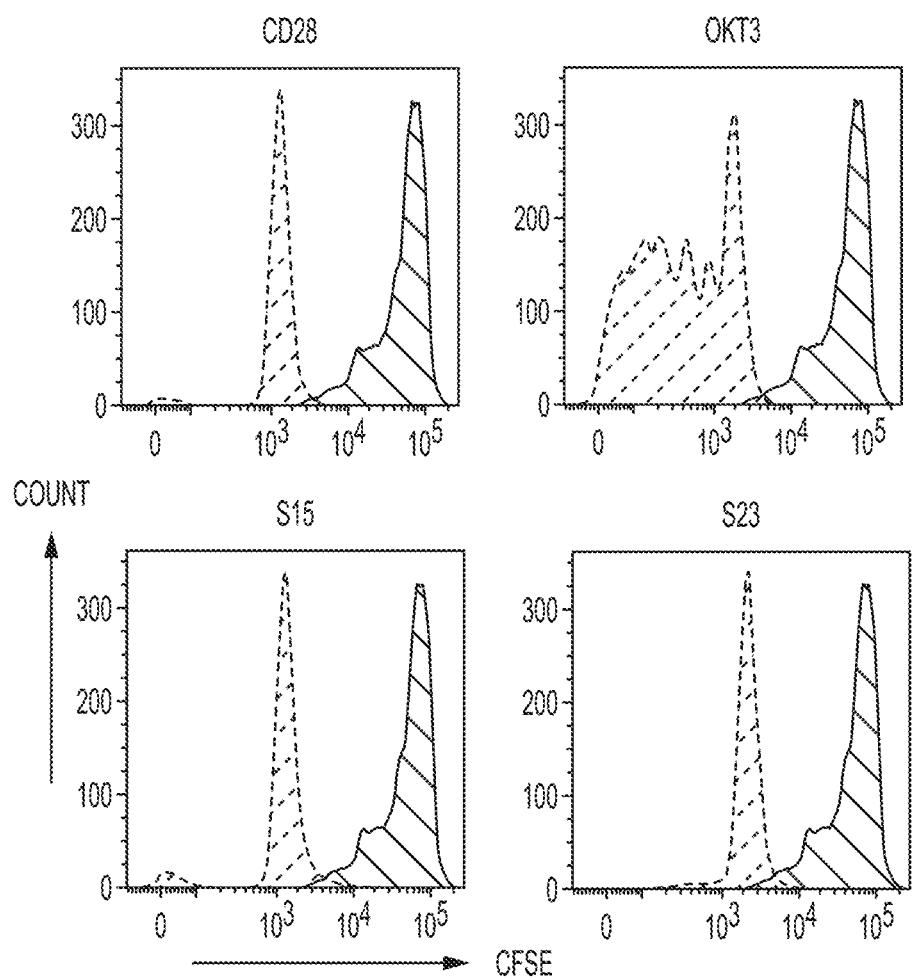
Figure 7D:
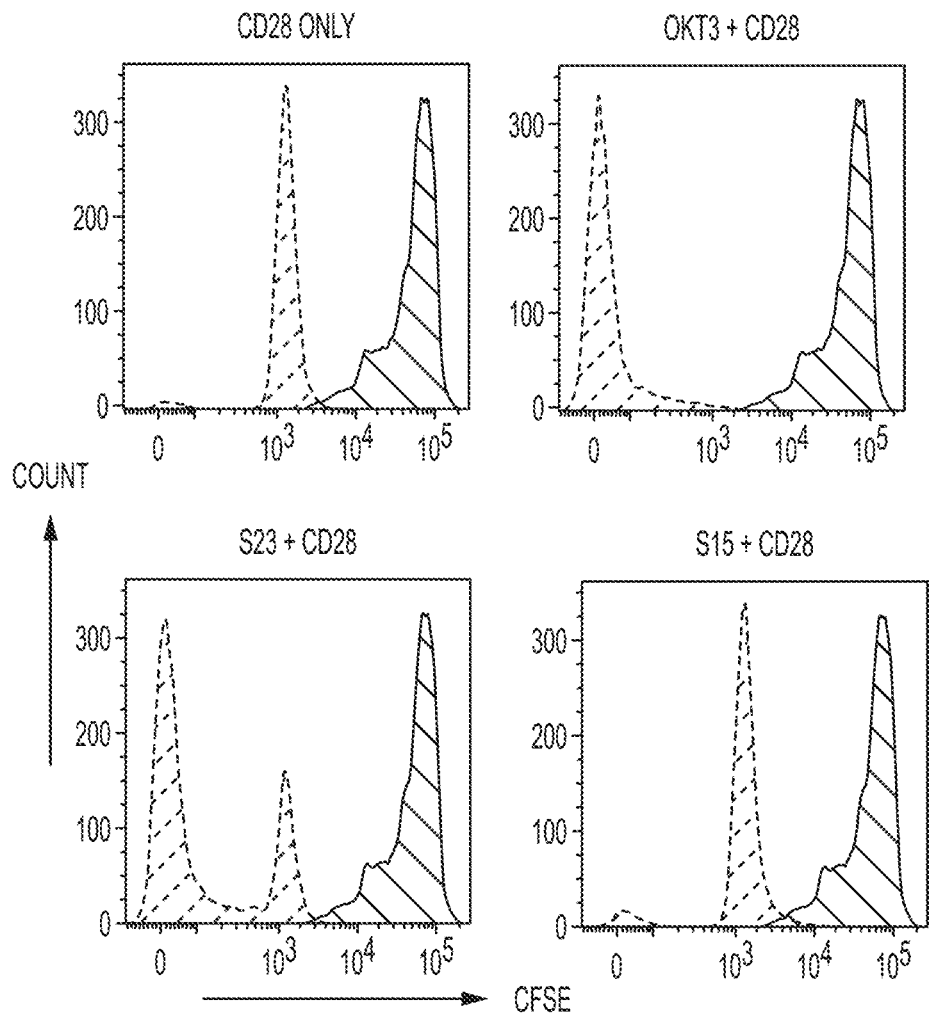

Cell proliferation assay—To assess proliferation of cells after stimulation through CD3-complex OKT3 or αβ-TCR engagement via mutant scFvs, a CFSE dye dilution method (CellTrace, ThermoFisher Scientific) was used. Live cells were loaded with 5 uM of CFSE dye (as per manufacturer's protocol) and then seeded at a density of 1 million cells/mL in complete RPMI-1640 media (10% FBS, 1× Glutamax and IL-2; 50IU/mL IL-2) on to polystyrene plate (Nunc) coated with either OKT3, S15, S23 alone or in combination with CD28 at 10 µg/mL concentration. Activated cells were sampled on Day 1, 2 and Day 6 and run on flow cytometry for quantification of CFSE diminution. Live CD3+ T cells were analyzed for CFSE fluorescence with 488 nm excitation on an appropriate filter on a BD LSR-Fortessa. Data were represented as histogram showing CFSE expression as distinct peak for each successive generation of T cells (FIGS. 7C and 7D). CFSE loaded PBMC was used as positive control. A commercially available anti-CD28 antibody was used as an experimental antibody control for T cell simulation.

K562-engineered artificial antigen presenting cells—S15 sequences were fused either to truncated human CD8 transmembrane (tCD8TM) domain or truncated human Fc-tCD8TM domain along with HA tag (FIG. 7A). cDNA representing S15-tCD8TM-HA or S15-tCD8TM-tFc fusion protein was synthesized as gene string products (Geneart). Using gateway recombination method S15 was cloned back into plasmid vector pLV300 containing HIV regulatory elements, Ig kappa leader peptide sequences flanked with gateway cloning sites. 293-METR cells were transfected with plasmids for transient expression, following which viral particles were harvested from culture and then concentrated on Amicon ultra centrifuge filters (Millipore). K562 cells were transfected to express T-cell co-stimulatory ligands such as CD86, CD137L, IL15-15Ra. Surface expression of introduced ligands was assessed by flow cytometry using commercially available antibodies for CD86, CD137L, IL15-15Ra (BD) and HA (Biolegend) or anti-human Fc antibodies (Life Tech) to detect S15 fusion protein. To assess efficacy of recombinant antibody to stimulate T cells in absence of co-stimulation, K562 cells were engineered to express CD64 and then loaded with whole antibodies as described previously.

Figure 7E:
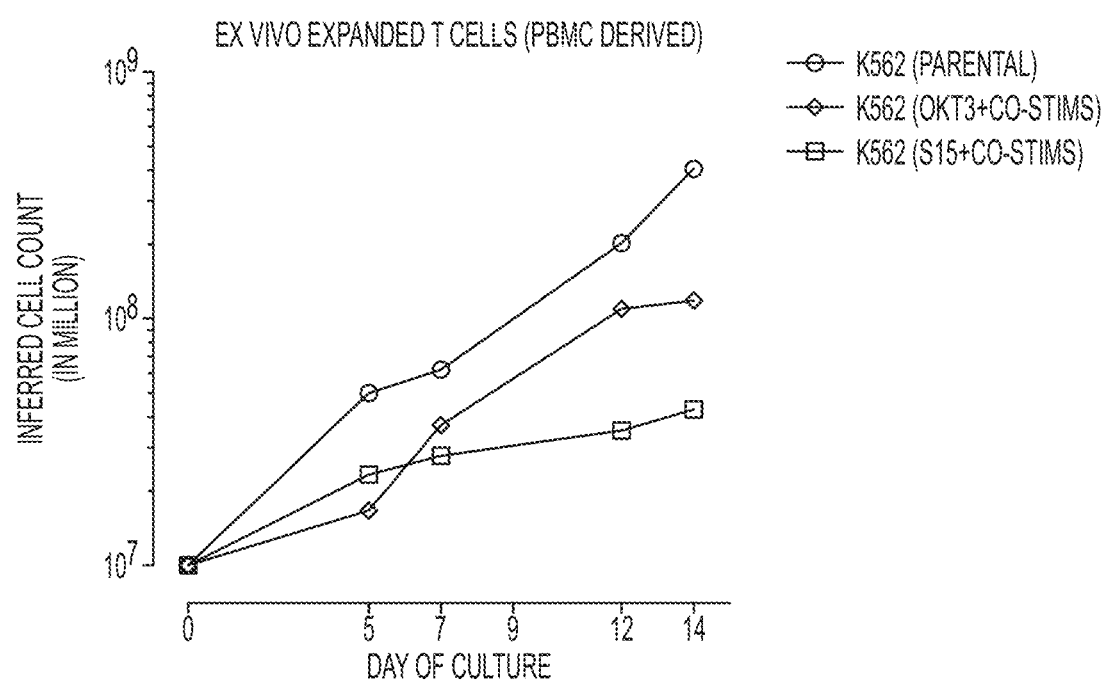
Figure 7F:
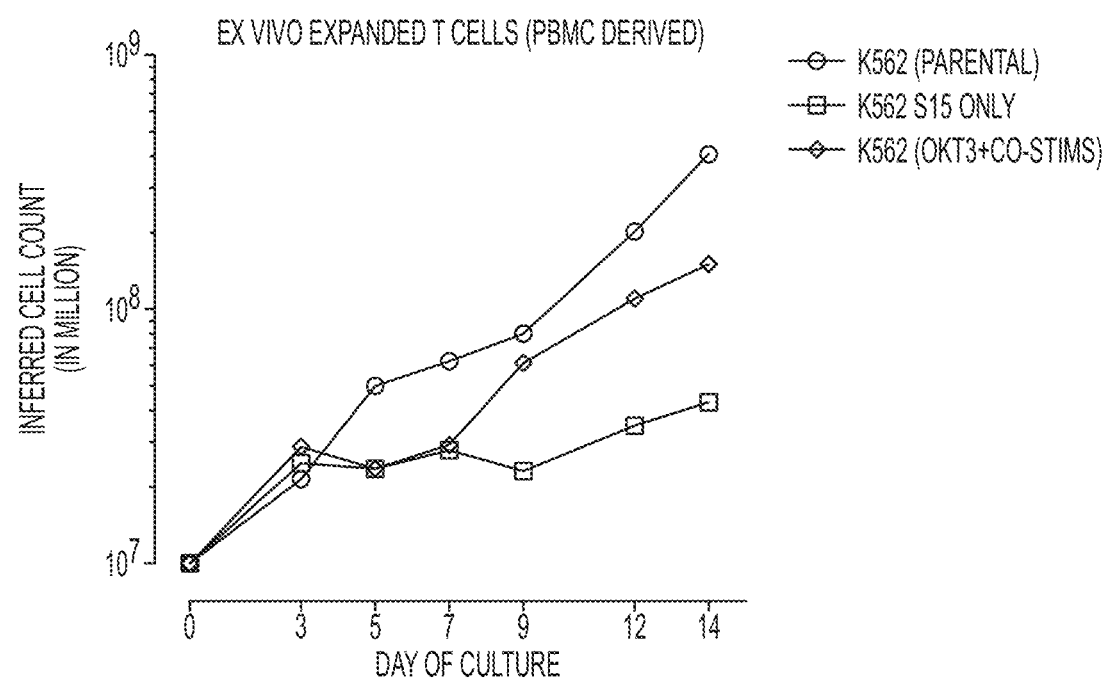

Ex vivo propagation of T cells on K562-S15 feeder cells (AaPC)—K562 cells were engineered to express S15 or its derivative along with T cell co-stimulatory ligands so that T cell activation is complete ex vivo. K562 cells stably expressing S15 alone or in combination with co-stimulatory ligands or K562-CD64 cells loaded with whole antibody were used as feeder cells after irradiation (FIG. 7B). PBMC or umbilical cord blood T cells (UCB) derived mononuclear cells were co-cultured with engineered irradiated K562s at a ratio of 1:1 along with IL-2 (50 IU/mL). Cells were stimulated twice at 7-day interval in a K562-PBMC co-culture system. Growth kinetics was monitored by counting live cells (Nexcelom™ trypan blue dye exclusion) (FIGS. 7C-7D). Immunophenotype was completed to ascertain the characteristics of expanded T cells (FIG. 7E). Emergence of $CD3^+$ $CD56^{neg}$T cell population was assessed by flow cytometry. Absolute cell number was monitored for estimating cell growth on different aAPCs (K562 cell only, K562 with S15 alone/or S15 with co-stimulatory ligands, K562 with anti-CD3ε mAb (OKT3) alone/or with co-stimulation, or K562-CD64 loaded with 515, S23 or OKT3. Immunophenotyping for ex vivo expanded T cells were performed to assess markers related exhaustion and memory phenotypes. (FIGS. 7E and 7F).

Figure 7G:
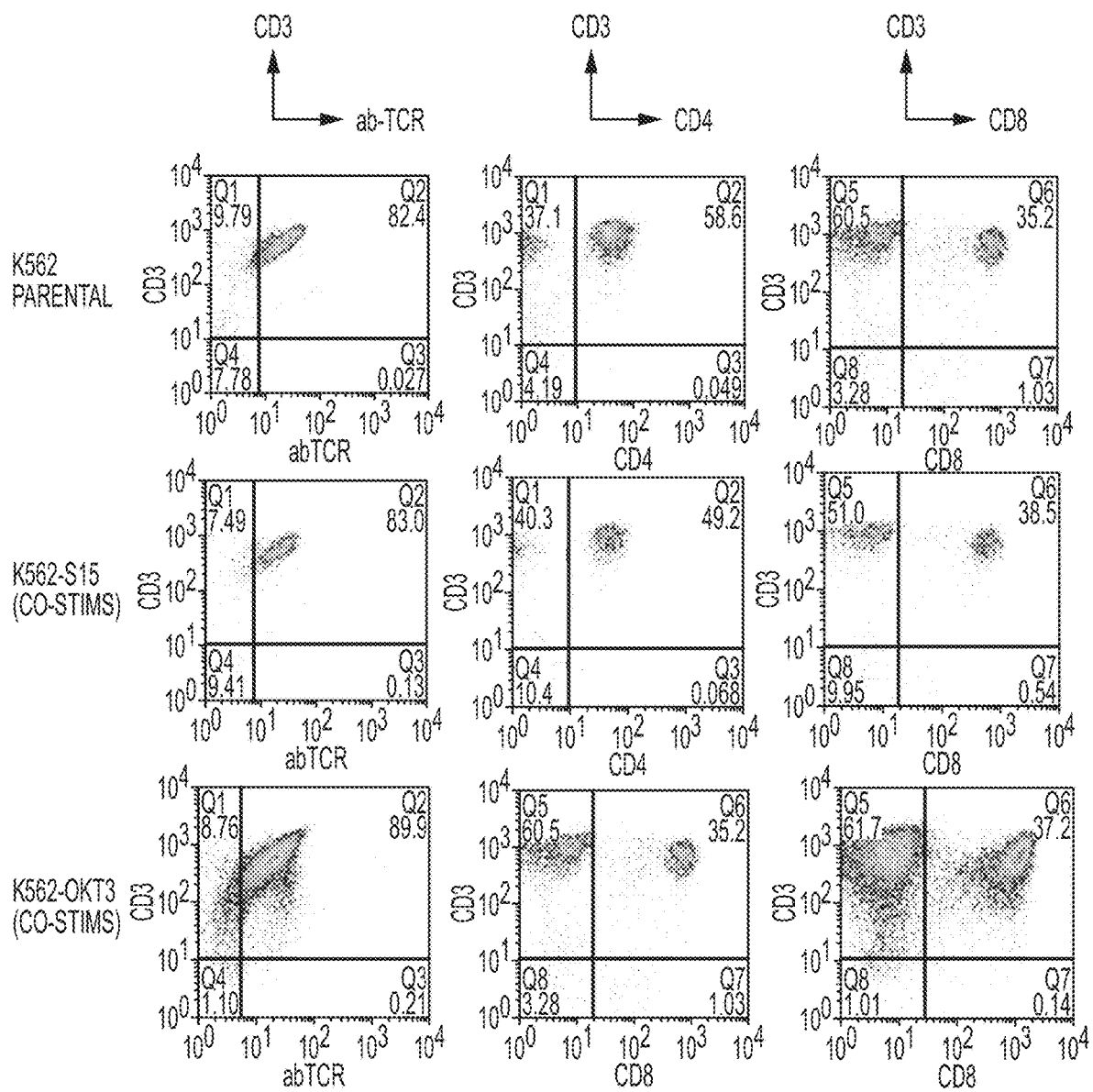
Figure 7H:
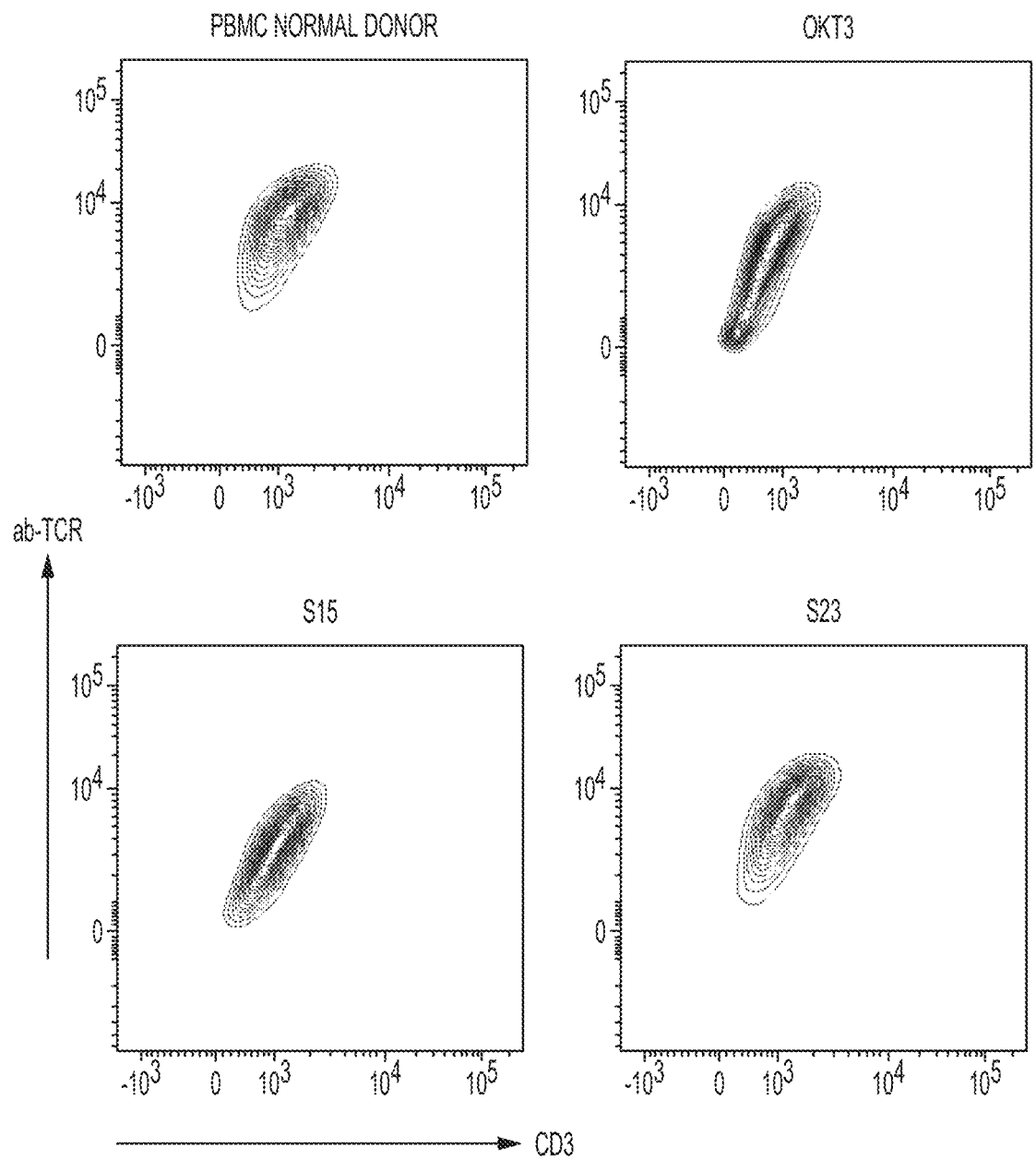
Figure 7I:
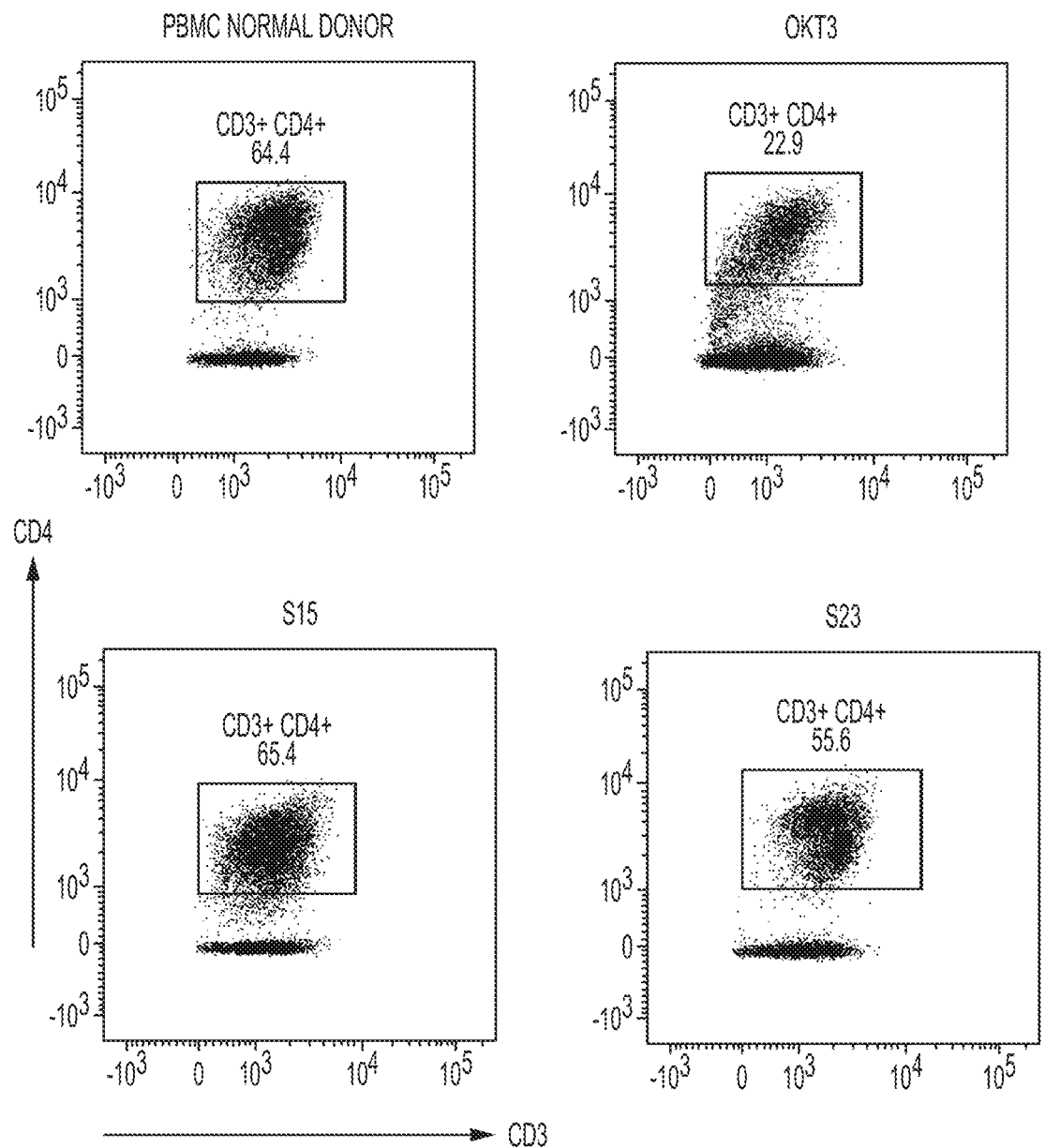
Figure 7J:
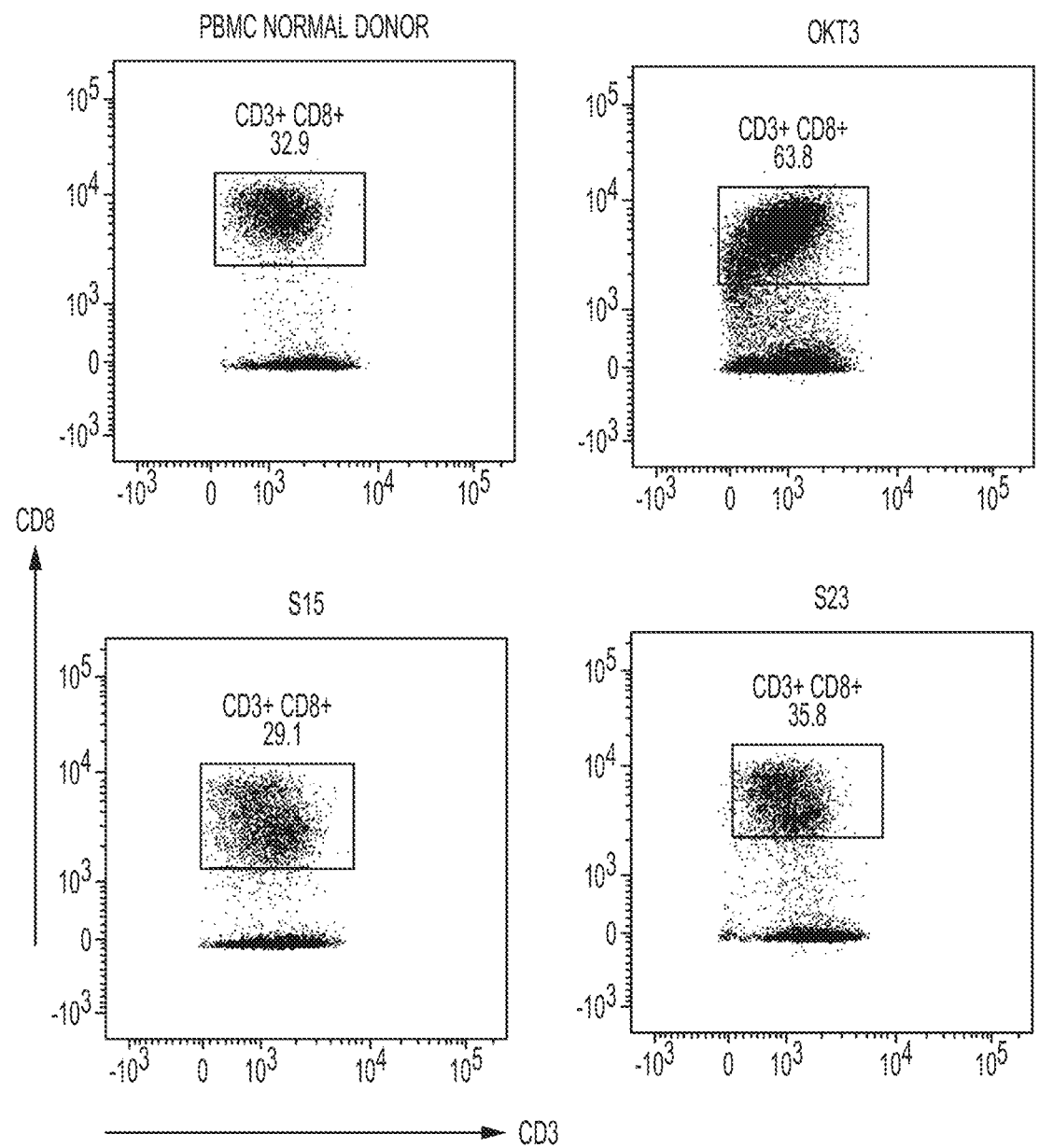
Figure 7K:
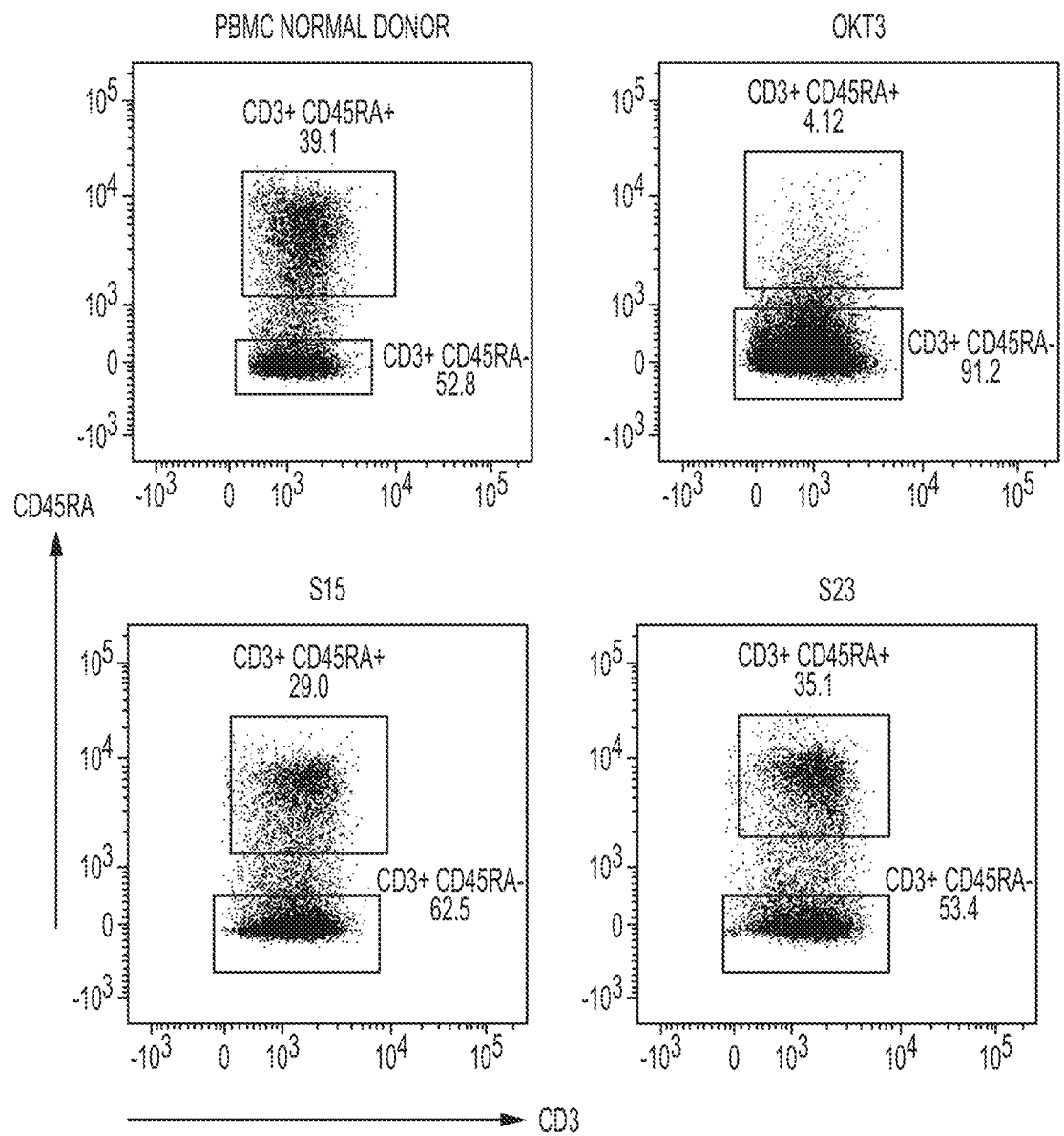
Figure 7L:
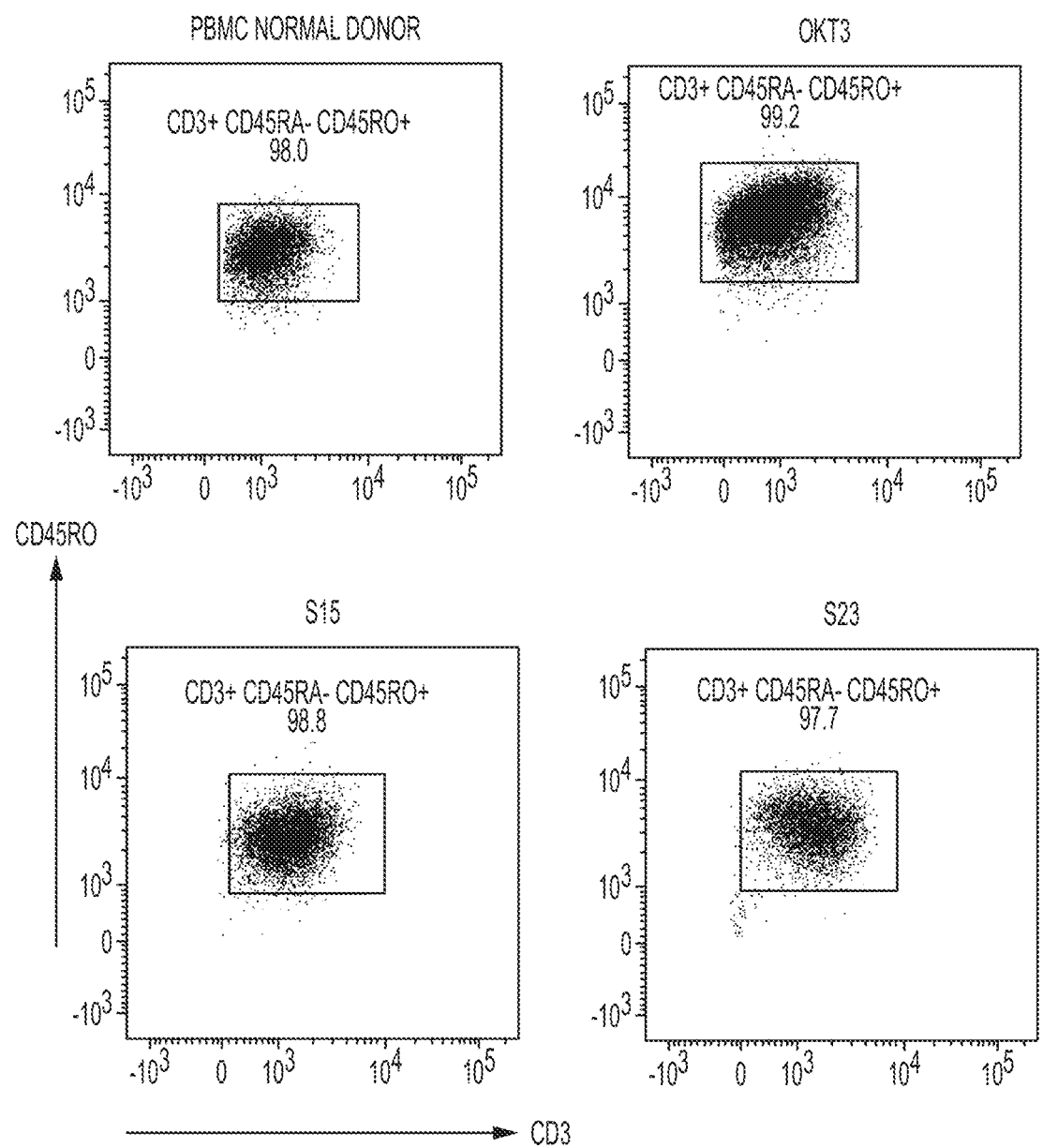
Figure 7M:
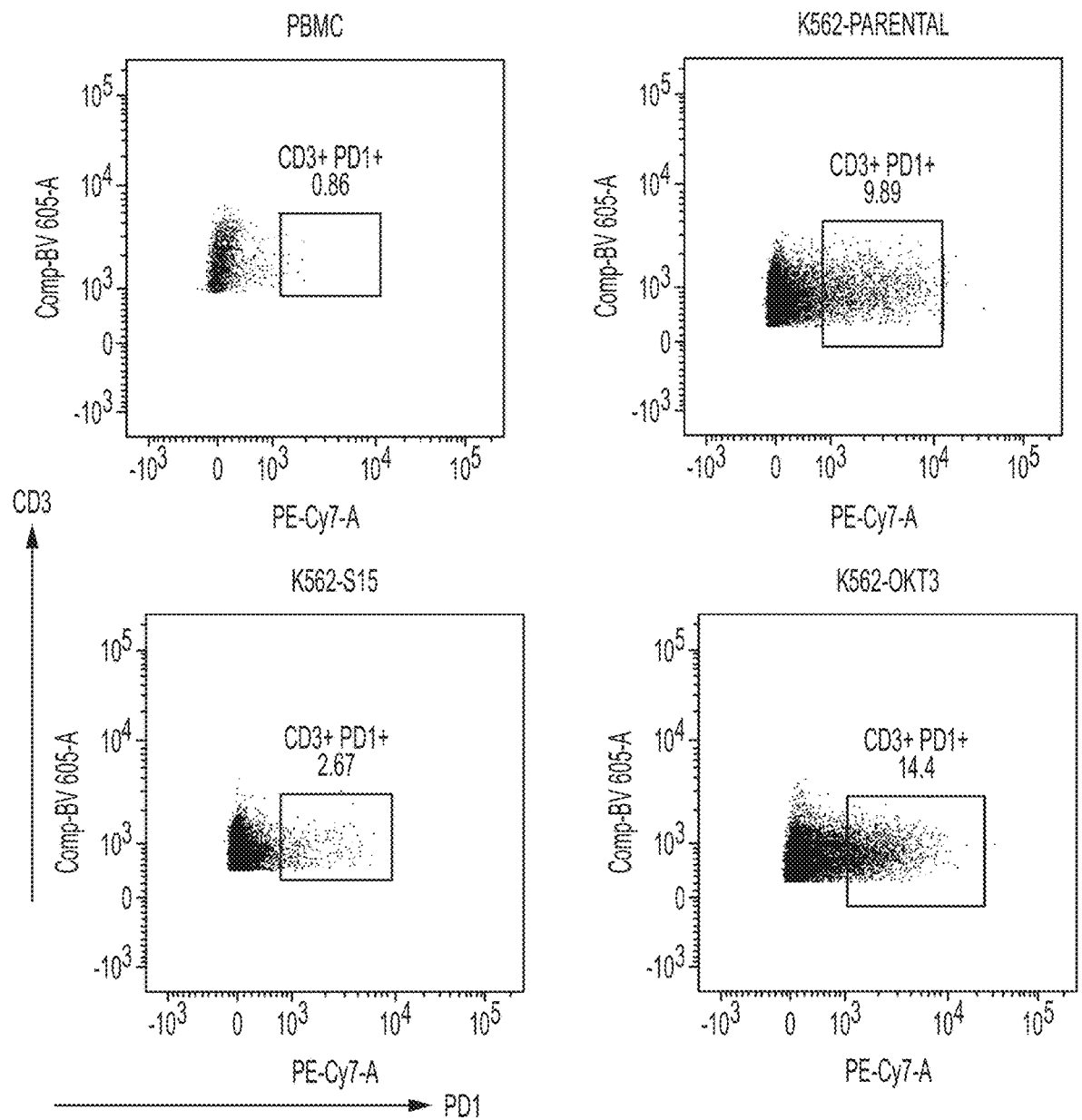

Flow Cytometry—BD LSR Fortessa X-20 was used for multiparametric immunophenotyping analysis of T cells. In brief, healthy donor PBMC or ex vivo cultured live T cells were washed by chilled FACS buffer containing (PBS with 2% FBS), incubated with fluorochrome conjugated antibodies for 20 min ice in dark. Next, cells were washed twice with FACS buffer and then incubated 5 min at room temp with Fixable viable dye for live dead staining. Gating was performed on live cells and excluded for monocytes ($CD14^{PoS}$) and B-cells ($CD19^{PoS}$) on a dump channel. T cells were identified as $CD3^{PoS}$ $CD56^{neg}$ and then analyzed for expression of αβ-TCR, markers for cell differentiation (CD25, CD69, CD45RA, and CD45RO), Th Phenotype (CD294 and CD25) and exhaustion (PD1, LAG3, TIM3, BLIMP). Antibody dilution and usages were performed as per manufacturer's guidelines. Compensation for multi-parameter analysis was done using calibration beads (eBioscience). Compensated data were analyzed by Flow Jo software V10 and expressed as dot plots. Each experiment was performed for three or more donors. (FIG. 7G)

TCR repertoire analysis by high throughput deep sequencing—Activated T cells' V gene rearrangements were analyzed in-depth by targeting human TCR-CDR3 region encoded by TCRβ gene (Adaptive Biotechnology's human TCRβ Deep level assay). The assay involves proprietary multiplex PCR primers, amplification steps that include a second PCR to incorporate synthetic immune receptor analogs to avoid amplification bias and accurate quantification of TCRB repertoire ImmuSEQ™ software (Robins, H. S., Campregher, P. V., Srivastava, S. K., Wacher, A., Turtle, C. J., Kahsai, O., Riddell, S. R., Warren, E. H. and Carlson, C. S. (2009) Comprehensive assessment of T-cell receptor beta-chain diversity in alphabeta T cells. Blood, 114, 4099-4107.). The results are shown in FIGS. 8A-8B.

Immune repertoire of ex vivo propagated T cells was assessed by next generation deep sequencing of TCRβ gene encoding TCR-CDR3 (hTCRβ deep level assay, Adaptive Biotech). Genomic DNA isolated from $CD3^+$ T cells (PBMC control) or ex vivo expanded T cells were used for TCR repertoire analysis. Various APC groups used in the assay were K562 C⁻ (unmodified control), K562C⁻ expressing S15 only, K562C⁻ expressing S15 along with co-stimulatory molecules (CD86, CD137L and IL15-15Ra), K562C⁻ loaded with OKT3 (anti-CD3ε mAb) and co-stimulatory molecules (CD86, CD137L and IL15-15Ra). Amplicons were generated by multiplexing through proprietary primer mixture provided in the vendor provided kit. Carlson, C. S., Emerson, R. O., Sherwood, A. M., Desmarais, C., Chung, M. W., Parsons, J. M., Steen, M. S., LaMadrid-Herrmannsfeldt, M. A., Williamson, D. W., Livingston, R. J. et al. (2013) Using synthetic templates to design an unbiased multiplex PCR assay. Nature communications, 4, 268. A two-step amplification process was followed where synthetic immune receptor analogs were introduced for unbiased estimation of TCRβ repertoire. Robins, H. S., Campregher, P. V., Srivastava, S. K., Wacher, A., Turtle, C. J., Kahsai, O., Riddell, S. R., Warren, E. H. and Carlson, C. S. (2009) Comprehensive assessment of T-cell receptor beta-chain diversity in alphabeta T cells. *Blood,* 114, 4099-4107. TCR libraries were generated on Illumina miSEQ platform and data analyzed by ImmunoSeQ analyzer after a standard QC check (Adaptive Biotech). Immune sequencing data were obtained from each group of activated T cells as well as from un-manipulated healthy donor PBMC T cells. All data were compared before and after manipulation (primary versus activated T cells). Data representing TCRV gene frequency, CDR3 chain length, paired gene frequency was reported. Top clone distribution was also tracked based on percentage of sequencing reads accounted for each individual clone within sample groups. Scatter plot analysis was provided to estimate frequency of appearance of clones for each sample group. Clonality score with respect to Shannon's entropy, Pearson co-efficient values ($r^2$) were calculated to ascertain clonal overlap occurring among each group of T cells activated by different strategies (S15 vs. OKT3 as compared to un-manipulated donor PBMC T cells). (FIG. 8D).

Discussion—The inventors describe an alternate method of T-cell activation and ex vivo propagation to generate clinical grade T cells. In contrast to CD3 complex activation via CDR3ε-specific mAb OKT3 along with super-agonist anti-CD28 mAb, they activated T cells by αβ-TCR cross-linking via an engineered TCR alpha chain specific recombinant antibody fragment tethered on K562-AaPC (activating and propagating cells).

Single chain affinity optimized novel mutants 15 and 23 (S15 and S23) with high affinity towards αβ-TCR$^+$T cells, which were used to activate and propagate primary T cells in culture by cross-linking TCR. Growth kinetics and phenotype of S15-AaPC mediated T cell activation was parallel to that achieved by CD3ε specific OKT3 mAb stimulation.

Figure 11:
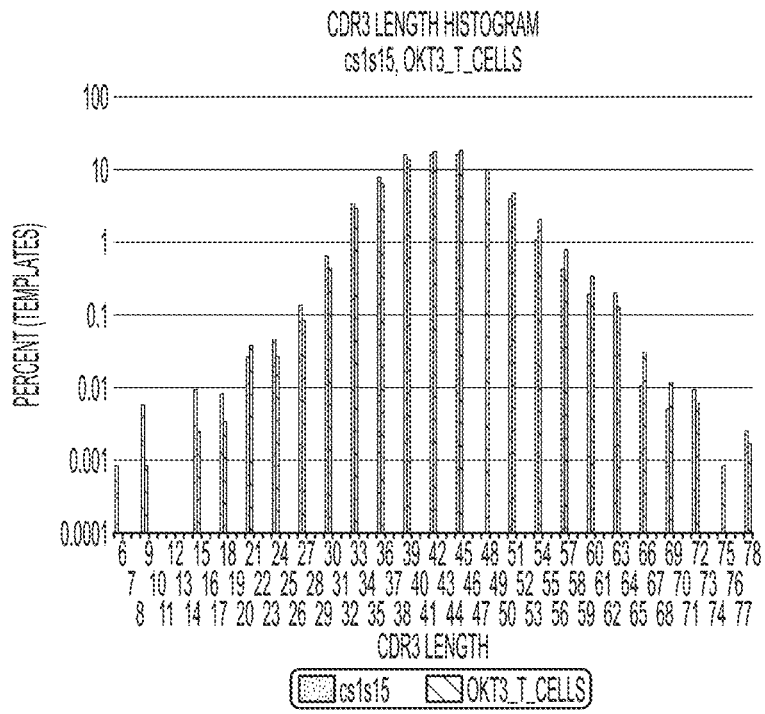
FIG. 11. Bell curve distribution of CDR3 chain length both for S15 activated T cells and OKT3 activated T cells. CDR3 chain length of activated T cells when compared to PBMC-derived T cells, no perturbation over all distribution of CDR3 chain is observed.
Figure 11:
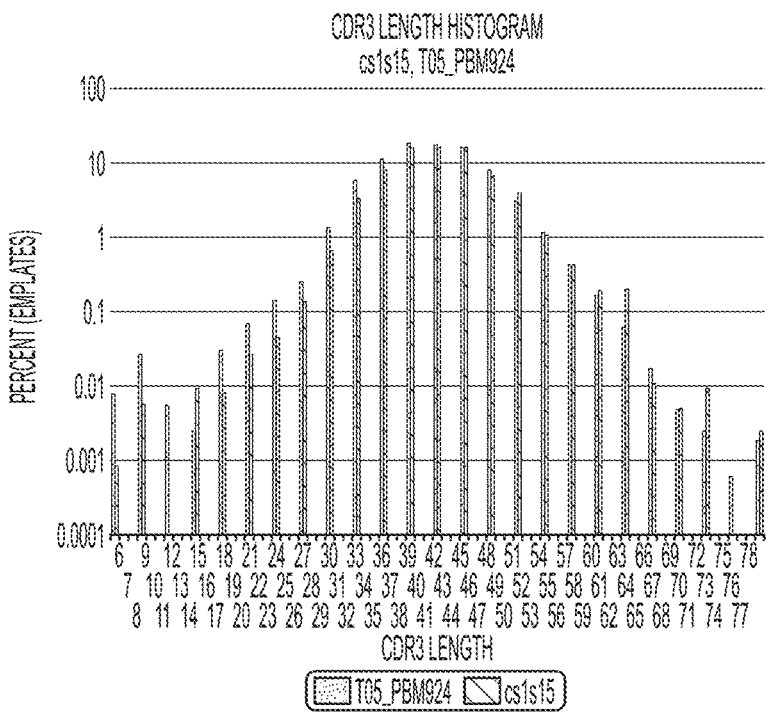

High throughput deep sequencing of activated T cells' genomic DNA revealed distinct V-gene rearrangements and preservation of clonal population by TCR-cross linking via S15. The analysis showed neither any unexpected change in functional V gene rearrangement nor any skewing of immune repertoire. αβ$^+$ TCR$^+$ T-cells generated via TCR cross-linking can be helpful in situations where preservation of clonal population is desirable after ex vivo activation and propagation. (see FIGS. 9-11).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An isolated antibody or antigen-binding fragment thereof that specifically binds to an epitope of T-cell receptor alpha (TCRα) polypeptide, wherein the antibody or antigen-binding fragment thereof comprises a heavy chain variable region (VH) and a light chain variable region (VL) wherein the VH comprises three complementarity determining regions (CDRs) HCDR1, HCDR2, and HCDR3, found within the amino acid sequence of SEQ ID NO: 19 and wherein the VL comprises three CDRs, LCDR1, LCDR2 and LCDR3, found within the amino acid sequence of SEQ ID NO: 20, wherein
   (a) HCDR1 comprises the amino acid sequence of SEQ ID NO: 15;
   (b) HCDR2 comprises the amino acid sequence of SEQ ID NO: 16;
   (c) HCDR3 comprises the amino acid sequence of SEQ ID NO: 17;
   (d) LCDR1 comprises the amino acid sequence of SEQ ID NO: 18;
   (e) LCDR2 comprises the amino acid sequence of SEQ ID NO: 5; and
   (f) LCDR3 comprises the amino acid sequence of SEQ ID NO: 6.

2. The antibody or antigen-binding fragment thereof according to claim 1, wherein the antibody or antigen-binding fragment thereof is human or humanized.

3. The antibody or antigen-binding fragment thereof according to claim 1, wherein the antigen-binding fragment thereof is a Fab, Fab', F(ab')2, scFv, or disulfide-linked Fv (sdFv).

4. The antibody or antigen-binding fragment thereof according to claim 1, wherein the antibody is an IgG, IgM or IgA antibody.

5. The antibody or antigen-binding fragment thereof according to claim 1, wherein the antibody or antigen-binding fragment thereof is membrane bound.

6. The antibody or antigen-binding fragment thereof according to claim 1, wherein the antibody or antigen-binding fragment thereof is conjugated to a reporter.

7. The antibody or antigen-binding fragment thereof according to claim 1, wherein the antibody antigen-binding fragment thereof comprises a VH comprising the amino acid sequence of SEQ ID NO: 19, and a VL comprising the amino acid sequence of SEQ ID NO: 20.

8. The antibody or antigen-binding fragment thereof according to claim 1, wherein the epitope of the TCRα polypeptide comprises GSTLRG (SEQ ID NO:1).

9. The antibody or antigen-binding fragment thereof according to claim 1, further comprising a transmembrane domain.

10. An isolated polynucleotide comprising a nucleic acid sequence encoding the antibody or antigen binding fragment thereof according to claim 1.

11. An isolated host cell comprising one or more polynucleotides according to claim 10.

12. A method for selecting a cell comprising a TCRα comprising:
   (i) contacting the cell with an antibody or antigen-binding fragment thereof according to claim 1; and
   (ii) selecting a cell comprising the TCRα.

13. A method for expanding and/or activating T-cells comprising contacting the T-cells with artificial antigen presenting cells (aAPCs) in the presence of an antibody or antigen binding fragment thereof according to claim 1.

14. A method of treating an autoimmune disease or a T-cell leukemia in a subject in need of treatment, comprising administering an antibody or antigen-binding fragment thereof according to claim 1.

* * * * *

SEQUENCE LISTING

```
<160> NUMBER OF SEQ ID NOS: 72

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1

Gly Ser Thr Leu Arg Gly
1               5

<210> SEQ ID NO 2
<211> LENGTH: 15
<212> TYPE: PRT
<213> ORGANISM: Artificial Sequence
<220> FEATURE:
<223> OTHER INFORMATION: Synthetic peptide

<400> SEQUENCE: 2

Lys Ala Ser Gly Tyr Thr Phe Thr Asp Tyr Tyr Met Asn Trp Val
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Trp Ile Gly Glu Ile Asn Pro Asn Asn
1               5
```

```
<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Asn Thr Tyr Leu Glu Trp Tyr
1               5

<210> SEQ ID NO 5
<211> LENGTH: 12
<212> TYPE: PRT
<213> ORGANISM: Artificial Sequence
<220> FEATURE:
<223> OTHER INFORMATION: Synthetic peptide

<400> SEQUENCE: 5

Lys Leu Leu Ile Tyr Lys Val Ser Asn Arg Phe Ser
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide

<400> SEQUENCE: 6

Phe Gln Gly Ser His Val Pro Trp
1               5

<210> SEQ ID NO 7
<211> LENGTH: 111
<212> TYPE: PRT
<213> ORGANISM: Artificial Sequence
<220> FEATURE:
<223> OTHER INFORMATION: Synthetic peptide

<400> SEQUENCE: 7

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Glu Ile Asn Pro Asn Asn Gly Gly Thr Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Cys Asp Tyr Trp Gly Gln Gly Thr Thr Leu Thr Val Ser Ser
            100                 105                 110

<210> SEQ ID NO 8
<211> LENGTH: 112
<212> TYPE: PRT
<213> ORGANISM: Artificial Sequence
<220> FEATURE:
<223> OTHER INFORMATION: Synthetic peptide
```

<400> SEQUENCE: 8

Asp Ile Val Leu Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Asn Thr Tyr Leu Glu Trp Phe
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide

<400> SEQUENCE: 10

Met Gln Gly Ser His Val Pro Trp
1               5

<210> SEQ ID NO 11
<211> LENGTH: 111
<212> TYPE: PRT
<213> ORGANISM: Artificial Sequence
<220> FEATURE:
<223> OTHER INFORMATION: Synthetic peptide

<400> SEQUENCE: 11

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Glu Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Cys Ala Tyr Leu Gly Gln Gly Thr Thr Leu Thr Val Ser Ser
            100                 105                 110

```
<210> SEQ ID NO 12
<211> LENGTH: 112
<212> TYPE: PRT
<213> ORGANISM: Artificial Sequence
<220> FEATURE:
<223> OTHER INFORMATION: Synthetic peptide

<400> SEQUENCE: 12

Asp Ile Val Leu Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Met Gln Gly
                85                  90                  95

Ser His Val Pro Trp Thr Phe Gly Gly Gly Thr Lys Leu Glu Ile Lys
            100                 105                 110

<210> SEQ ID NO 13
<211> LENGTH: 111
<212> TYPE: PRT
<213> ORGANISM: Artificial Sequence
<220> FEATURE:
<223> OTHER INFORMATION: Synthetic peptide

<400> SEQUENCE: 13

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Glu Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Cys Ala Tyr Trp Gly Gln Gly Thr Thr Leu Thr Val Ser Ser
            100                 105                 110

<210> SEQ ID NO 14
<211> LENGTH: 112
<212> TYPE: PRT
<213> ORGANISM: Artificial Sequence
<220> FEATURE:
<223> OTHER INFORMATION: Synthetic peptide

<400> SEQUENCE: 14

Asp Ile Val Leu Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30
```

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Met Gln Gly
                 85                  90                  95

Ser His Val Pro Trp Thr Phe Gly Gly Gly Thr Lys Leu Glu Ile Lys
            100                 105                 110

<210> SEQ ID NO 15
<211> LENGTH: 15
<212> TYPE: PRT
<213> ORGANISM: Artificial Sequence
<220> FEATURE:
<223> OTHER INFORMATION: Synthetic peptide

<400> SEQUENCE: 15

Lys Ala Ser Gly Tyr Thr Phe Thr Gly Tyr Tyr Met Asn Trp Val
1               5                   10                  15

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide

<400> SEQUENCE: 16

Trp Ile Gly Gly Ile Asn Pro Asn Asn
1               5

<210> SEQ ID NO 17
<211> LENGTH: 4
<212> TYPE: PRT
<213> ORGANISM: Artificial Sequence
<220> FEATURE:
<223> OTHER INFORMATION: Synthetic peptide

<400> SEQUENCE: 17

Cys Arg Tyr Trp
1

<210> SEQ ID NO 18
<211> LENGTH: 11
<212> TYPE: PRT
<213> ORGANISM: Artificial Sequence
<220> FEATURE:
<223> OTHER INFORMATION: Synthetic peptide

<400> SEQUENCE: 18

Gln Ser Ile Val His Gly Gly Gly Asn Thr Tyr
1               5                   10

<210> SEQ ID NO 19
<211> LENGTH: 111
<212> TYPE: PRT
<213> ORGANISM: Artificial Sequence
<220> FEATURE:
<223> OTHER INFORMATION: Synthetic peptide

<400> SEQUENCE: 19

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Gly Tyr
            20                  25                  30

Tyr Met Asn Trp Val Lys Gln Ser His Gly Lys Ser Leu Glu Trp Ile
        35                  40                  45

Gly Gly Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Cys Arg Tyr Trp Gly Gln Gly Thr Thr Leu Thr Val Ser Ser
                100                 105                 110

<210> SEQ ID NO 20
<211> LENGTH: 112
<212> TYPE: PRT
<213> ORGANISM: Artificial Sequence
<220> FEATURE:
<223> OTHER INFORMATION: Synthetic peptide

<400> SEQUENCE: 20

Asp Ile Val Leu Thr Gln Thr Pro Leu Ser Leu Pro Val Ser Leu Gly
1               5                   10                  15

Asp Gln Ala Ser Ile Ser Cys Arg Ser Ser Gln Ser Ile Val His Gly
            20                  25                  30

Gly Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
                100                 105                 110

<210> SEQ ID NO 21
<211> LENGTH: 4
<212> TYPE: PRT
<213> ORGANISM: Artificial Sequence
<220> FEATURE:
<223> OTHER INFORMATION: Synthetic peptide

<400> SEQUENCE: 21

Cys Asp Tyr Trp
1

<210> SEQ ID NO 22
<211> LENGTH: 4
<212> TYPE: PRT
<213> ORGANISM: Artificial Sequence
<220> FEATURE:
<223> OTHER INFORMATION: Synthetic peptide

<400> SEQUENCE: 22

Cys Ala Tyr Leu
1

<210> SEQ ID NO 23
<211> LENGTH: 4

```
<212> TYPE: PRT
<213> ORGANISM: Artificial Sequence
<220> FEATURE:
<223> OTHER INFORMATION: Synthetic peptide

<400> SEQUENCE: 23

Cys Ala Tyr Trp
1

<210> SEQ ID NO 24
<211> LENGTH: 27
<212> TYPE: PRT
<213> ORGANISM: Homo sapiens

<400> SEQUENCE: 24

Cys Asp Ile Tyr Ile Trp Ala Pro Leu Ala Gly Ile Cys Val Ala Leu
1               5                   10                  15

Leu Leu Ser Leu Ile Ile Thr Leu Ile Cys Tyr
            20                  25

<210> SEQ ID NO 25
<211> LENGTH: 21
<212> TYPE: PRT
<213> ORGANISM: Homo sapiens

<400> SEQUENCE: 25

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 26
<211> LENGTH: 161
<212> TYPE: PRT
<213> ORGANISM: Homo sapiens

<400> SEQUENCE: 26

Ser Gln Phe Arg Val Ser Pro Leu Asp Arg Thr Trp Asn Leu Gly Glu
1               5                   10                  15

Thr Val Glu Leu Lys Cys Gln Val Leu Leu Ser Asn Pro Thr Ser Gly
            20                  25                  30

Cys Ser Trp Leu Phe Gln Pro Arg Gly Ala Ala Ala Ser Pro Thr Phe
        35                  40                  45

Leu Leu Tyr Leu Ser Gln Asn Lys Pro Lys Ala Ala Glu Gly Leu Asp
    50                  55                  60

Thr Gln Arg Phe Ser Gly Lys Arg Leu Gly Asp Thr Phe Val Leu Thr
65                  70                  75                  80

Leu Ser Asp Phe Arg Arg Glu Asn Glu Gly Tyr Tyr Phe Cys Ser Ala
                85                  90                  95

Leu Ser Asn Ser Ile Met Tyr Phe Ser His Phe Val Pro Val Phe Leu
            100                 105                 110

Pro Ala Lys Pro Thr Thr Thr Pro Ala Pro Arg Pro Pro Thr Pro Ala
        115                 120                 125

Pro Thr Ile Ala Ser Gln Pro Leu Ser Leu Arg Pro Glu Ala Cys Arg
    130                 135                 140

Pro Ala Ala Gly Gly Ala Val His Thr Arg Gly Leu Asp Phe Ala Cys
145                 150                 155                 160

Asp
```

```
<210> SEQ ID NO 27
<211> LENGTH: 28
<212> TYPE: PRT
<213> ORGANISM: Artificial sequence
<220> FEATURE:
<223> OTHER INFORMATION: Synthetic peptide

<400> SEQUENCE: 27

Cys Val Val Ser Asp Arg Gly Ser Thr Leu Gly Arg Leu Tyr Cys Val
1               5                   10                  15

Val Ser Asp Arg Gly Ser Thr Leu Gly Arg Leu Tyr
            20                  25

<210> SEQ ID NO 28
<211> LENGTH: 15
<212> TYPE: PRT
<213> ORGANISM: Artificial sequence
<220> FEATURE:
<223> OTHER INFORMATION: Synthetic peptide

<400> SEQUENCE: 28

Cys Val Val Ser Asp Arg Gly Ser Thr Leu Gly Arg Leu Ala Asp
1               5                   10                  15

<210> SEQ ID NO 29
<211> LENGTH: 30
<212> TYPE: PRT
<213> ORGANISM: Artificial sequence
<220> FEATURE:
<223> OTHER INFORMATION: Synthetic peptide

<400> SEQUENCE: 29

Cys Val Val Ser Asp Arg Gly Ser Thr Leu Gly Arg Leu Arg Asp Cys
1               5                   10                  15

Val Val Ser Asp Arg Gly Ser Thr Leu Gly Arg Leu Arg Asp
            20                  25                  30

<210> SEQ ID NO 30
<211> LENGTH: 14
<212> TYPE: PRT
<213> ORGANISM: Artificial sequence
<220> FEATURE:
<223> OTHER INFORMATION: Synthetic peptide

<400> SEQUENCE: 30

Cys Val Val Ser Asp Arg Gly Ser Thr Leu Gly Arg Leu Tyr
1               5                   10

<210> SEQ ID NO 31
<211> LENGTH: 15
<212> TYPE: PRT
<213> ORGANISM: Artificial sequence
<220> FEATURE:
<223> OTHER INFORMATION: Synthetic peptide

<400> SEQUENCE: 31

Cys Ala Val Ser Asp Arg Gly Ser Thr Leu Gly Arg Leu Ala Asp
1               5                   10                  15

<210> SEQ ID NO 32
<211> LENGTH: 15
<212> TYPE: PRT
<213> ORGANISM: Artificial sequence
<220> FEATURE:
<223> OTHER INFORMATION: Synthetic peptide

<400> SEQUENCE: 32
```

```
Cys Val Ala Ser Asp Arg Gly Ser Thr Leu Gly Arg Leu Ala Asp
1               5                   10                  15

<210> SEQ ID NO 33
<211> LENGTH: 15
<212> TYPE: PRT
<213> ORGANISM: Artificial sequence
<220> FEATURE:
<223> OTHER INFORMATION: Synthetic peptide

<400> SEQUENCE: 33

Cys Val Val Ala Asp Arg Gly Ser Thr Leu Gly Arg Leu Ala Asp
1               5                   10                  15

<210> SEQ ID NO 34
<211> LENGTH: 15
<212> TYPE: PRT
<213> ORGANISM: Artificial sequence
<220> FEATURE:
<223> OTHER INFORMATION: Synthetic peptide

<400> SEQUENCE: 34

Cys Val Val Ser Asp Arg Gly Ser Thr Leu Gly Arg Ala Ala Asp
1               5                   10                  15

<210> SEQ ID NO 35
<211> LENGTH: 15
<212> TYPE: PRT
<213> ORGANISM: Artificial sequence
<220> FEATURE:
<223> OTHER INFORMATION: Synthetic peptide

<400> SEQUENCE: 35

Cys Val Val Ser Ala Arg Gly Ser Thr Leu Gly Arg Leu Ala Asp
1               5                   10                  15

<210> SEQ ID NO 36
<211> LENGTH: 15
<212> TYPE: PRT
<213> ORGANISM: Artificial sequence
<220> FEATURE:
<223> OTHER INFORMATION: Synthetic peptide

<400> SEQUENCE: 36

Cys Val Val Ser Asp Ala Gly Ser Thr Leu Gly Arg Leu Ala Asp
1               5                   10                  15

<210> SEQ ID NO 37
<211> LENGTH: 15
<212> TYPE: PRT
<213> ORGANISM: Artificial sequence
<220> FEATURE:
<223> OTHER INFORMATION: Synthetic peptide

<400> SEQUENCE: 37

Cys Val Val Ser Asp Arg Ala Ser Thr Leu Gly Arg Leu Ala Asp
1               5                   10                  15

<210> SEQ ID NO 38
<211> LENGTH: 15
<212> TYPE: PRT
<213> ORGANISM: Artificial sequence
<220> FEATURE:
<223> OTHER INFORMATION: Synthetic peptide

<400> SEQUENCE: 38
```

Cys Val Val Ser Asp Arg Gly Ala Thr Leu Gly Arg Leu Ala Asp
1               5                   10                  15

<210> SEQ ID NO 39
<211> LENGTH: 15
<212> TYPE: PRT
<213> ORGANISM: Artificial sequence
<220> FEATURE:
<223> OTHER INFORMATION: Synthetic peptide

<400> SEQUENCE: 39

Cys Val Val Ser Asp Arg Gly Ser Ala Leu Gly Arg Leu Ala Asp
1               5                   10                  15

<210> SEQ ID NO 40
<211> LENGTH: 15
<212> TYPE: PRT
<213> ORGANISM: Artificial sequence
<220> FEATURE:
<223> OTHER INFORMATION: Synthetic peptide

<400> SEQUENCE: 40

Cys Val Val Ser Asp Arg Gly Ser Thr Ala Gly Arg Leu Ala Asp
1               5                   10                  15

<210> SEQ ID NO 41
<211> LENGTH: 15
<212> TYPE: PRT
<213> ORGANISM: Artificial sequence
<220> FEATURE:
<223> OTHER INFORMATION: Synthetic peptide

<400> SEQUENCE: 41

Cys Val Val Ser Asp Arg Gly Ser Thr Leu Ala Arg Leu Ala Asp
1               5                   10                  15

<210> SEQ ID NO 42
<211> LENGTH: 15
<212> TYPE: PRT
<213> ORGANISM: Artificial sequence
<220> FEATURE:
<223> OTHER INFORMATION: Synthetic peptide

<400> SEQUENCE: 42

Cys Val Val Ser Asp Arg Gly Ser Thr Leu Gly Ala Leu Ala Asp
1               5                   10                  15

<210> SEQ ID NO 43
<211> LENGTH: 14
<212> TYPE: PRT
<213> ORGANISM: Artificial sequence
<220> FEATURE:
<223> OTHER INFORMATION: Synthetic peptide

<400> SEQUENCE: 43

Cys Ala Ser Ser Ser Leu Ser Ala Asn Ser Pro Leu His Phe
1               5                   10

<210> SEQ ID NO 44
<211> LENGTH: 13
<212> TYPE: PRT
<213> ORGANISM: Artificial sequence
<220> FEATURE:
<223> OTHER INFORMATION: Synthetic peptide

<400> SEQUENCE: 44

Cys Ala Ser Ser Pro Gly His Thr Gly Glu Leu Phe Phe

```
<210> SEQ ID NO 45
<211> LENGTH: 15
<212> TYPE: PRT
<213> ORGANISM: Artificial sequence
<220> FEATURE:
<223> OTHER INFORMATION: Synthetic peptide

<400> SEQUENCE: 45

Cys Ala Ser Ser Ile Asp Arg Glu Asp Asn Ser Pro Leu His Phe
1               5                   10                  15

<210> SEQ ID NO 46
<211> LENGTH: 16
<212> TYPE: PRT
<213> ORGANISM: Artificial sequence
<220> FEATURE:
<223> OTHER INFORMATION: Synthetic peptide

<400> SEQUENCE: 46

Cys Ala Ser Ser Val Ser Gly Gly Ser Asn Thr Gly Glu Leu Phe Phe
1               5                   10                  15

<210> SEQ ID NO 47
<211> LENGTH: 16
<212> TYPE: PRT
<213> ORGANISM: Artificial sequence
<220> FEATURE:
<223> OTHER INFORMATION: Synthetic peptide

<400> SEQUENCE: 47

Cys Ala Ser Ser Leu Ala Gly Gly Gly Thr Asn Glu Lys Leu Phe Phe
1               5                   10                  15

<210> SEQ ID NO 48
<211> LENGTH: 15
<212> TYPE: PRT
<213> ORGANISM: Artificial sequence
<220> FEATURE:
<223> OTHER INFORMATION: Synthetic peptide

<400> SEQUENCE: 48

Cys Ala Ser Ser Glu Phe Lys Gln Gly Asn Thr Glu Ala Phe Phe
1               5                   10                  15

<210> SEQ ID NO 49
<211> LENGTH: 15
<212> TYPE: PRT
<213> ORGANISM: Artificial sequence
<220> FEATURE:
<223> OTHER INFORMATION: Synthetic peptide

<400> SEQUENCE: 49

Cys Ala Ser Ser Asn His Pro Gly Pro Phe Asn Glu Gln Tyr Phe
1               5                   10                  15

<210> SEQ ID NO 50
<211> LENGTH: 15
<212> TYPE: PRT
<213> ORGANISM: Artificial sequence
<220> FEATURE:
<223> OTHER INFORMATION: Synthetic peptide

<400> SEQUENCE: 50

Cys Ala Ser Ser Gln Asp Pro Gly Gly Val Glu Thr Gln Tyr Phe
1               5                   10                  15
```

<210> SEQ ID NO 51
<211> LENGTH: 14
<212> TYPE: PRT
<213> ORGANISM: Artificial sequence
<220> FEATURE:
<223> OTHER INFORMATION: Synthetic peptide

<400> SEQUENCE: 51

Cys Ala Ser Ser His Val Ala Ser Thr Asp Thr Gln Tyr Phe
1               5                   10

<210> SEQ ID NO 52
<211> LENGTH: 13
<212> TYPE: PRT
<213> ORGANISM: Artificial sequence
<220> FEATURE:
<223> OTHER INFORMATION: Synthetic peptide

<400> SEQUENCE: 52

Cys Ala Ser Thr Thr Gly Gly Arg Thr Glu Ala Phe Phe
1               5                   10

<210> SEQ ID NO 53
<211> LENGTH: 15
<212> TYPE: PRT
<213> ORGANISM: Artificial sequence
<220> FEATURE:
<223> OTHER INFORMATION: Synthetic peptide

<400> SEQUENCE: 53

Cys Ala Ser Ser Trp Tyr Arg Glu Val Ile Asp Gly Tyr Thr Phe
1               5                   10                  15

<210> SEQ ID NO 54
<211> LENGTH: 13
<212> TYPE: PRT
<213> ORGANISM: Artificial sequence
<220> FEATURE:
<223> OTHER INFORMATION: Synthetic peptide

<400> SEQUENCE: 54

Cys Ala Arg Ser Phe Arg Ala Gly Arg Asp Gly Thr Phe
1               5                   10

<210> SEQ ID NO 55
<211> LENGTH: 14
<212> TYPE: PRT
<213> ORGANISM: Artificial sequence
<220> FEATURE:
<223> OTHER INFORMATION: Synthetic peptide

<400> SEQUENCE: 55

Cys Ala Gly Ser Gly Gly Ala Ser Tyr Asn Glu Gln Phe Phe
1               5                   10

<210> SEQ ID NO 56
<211> LENGTH: 12
<212> TYPE: PRT
<213> ORGANISM: Artificial sequence
<220> FEATURE:
<223> OTHER INFORMATION: Synthetic peptide

<400> SEQUENCE: 56

Cys Ala Ser Ser Leu Asn Trp Asp Ser Gly Phe Phe
1               5                   10

```
<210> SEQ ID NO 57
<211> LENGTH: 14
<212> TYPE: PRT
<213> ORGANISM: Artificial sequence
<220> FEATURE:
<223> OTHER INFORMATION: Synthetic peptide

<400> SEQUENCE: 57

Cys Ala Ser Ser Gln Trp Asp Tyr Asn Ser Pro Leu His Phe
1               5                   10

<210> SEQ ID NO 58
<211> LENGTH: 14
<212> TYPE: PRT
<213> ORGANISM: Artificial sequence
<220> FEATURE:
<223> OTHER INFORMATION: Synthetic peptide

<400> SEQUENCE: 58

Cys Ala Ser Ser Asp Ser Gly Thr His Tyr Gly Tyr Thr Phe
1               5                   10

<210> SEQ ID NO 59
<211> LENGTH: 13
<212> TYPE: PRT
<213> ORGANISM: Artificial sequence
<220> FEATURE:
<223> OTHER INFORMATION: Synthetic peptide

<400> SEQUENCE: 59

Cys Ala Ser Ser Gln Asp Arg Gln Gly Thr Asp Thr Phe
1               5                   10

<210> SEQ ID NO 60
<211> LENGTH: 16
<212> TYPE: PRT
<213> ORGANISM: Artificial sequence
<220> FEATURE:
<223> OTHER INFORMATION: Synthetic peptide

<400> SEQUENCE: 60

Cys Ala Ser Ser Gly Leu Ala Gly Ser Gly Ala Asn Val Leu Thr Phe
1               5                   10                  15

<210> SEQ ID NO 61
<211> LENGTH: 17
<212> TYPE: PRT
<213> ORGANISM: Artificial sequence
<220> FEATURE:
<223> OTHER INFORMATION: Synthetic peptide

<400> SEQUENCE: 61

Cys Ala Ser Ser Leu Trp Ala Gly Asp Arg Val Lys Asn Ile Gln Tyr
1               5                   10                  15

Phe

<210> SEQ ID NO 62
<211> LENGTH: 15
<212> TYPE: PRT
<213> ORGANISM: Artificial sequence
<220> FEATURE:
<223> OTHER INFORMATION: Synthetic peptide

<400> SEQUENCE: 62

Cys Ala Ser Thr Arg Glu Gly Gln Gln Asn Thr Glu Ala Phe Phe
1               5                   10                  15
```

<210> SEQ ID NO 63
<211> LENGTH: 16
<212> TYPE: PRT
<213> ORGANISM: Artificial sequence
<220> FEATURE:
<223> OTHER INFORMATION: Synthetic peptide

<400> SEQUENCE: 63

Cys Ala Ser Ser Leu Ala Gly Leu Leu Asn Tyr Gly Tyr Thr Phe
1               5                   10                  15

<210> SEQ ID NO 64
<211> LENGTH: 15
<212> TYPE: PRT
<213> ORGANISM: Artificial sequence
<220> FEATURE:
<223> OTHER INFORMATION: Synthetic peptide

<400> SEQUENCE: 64

Cys Ala Ser Thr Ser Arg Gln Gly Val Asn Thr Glu Ala Phe Phe
1               5                   10                  15

<210> SEQ ID NO 65
<211> LENGTH: 15
<212> TYPE: PRT
<213> ORGANISM: Artificial sequence
<220> FEATURE:
<223> OTHER INFORMATION: Synthetic peptide

<400> SEQUENCE: 65

Cys Ala Ser Ser Leu Thr Ser Gly Gly Asp Asn Glu Gln Phe Phe
1               5                   10                  15

<210> SEQ ID NO 66
<211> LENGTH: 14
<212> TYPE: PRT
<213> ORGANISM: Artificial sequence
<220> FEATURE:
<223> OTHER INFORMATION: Synthetic peptide

<400> SEQUENCE: 66

Cys Ala Gly Ser Gly Gly Ala Ser Tyr Asn Glu Gln Phe Phe
1               5                   10

<210> SEQ ID NO 67
<211> LENGTH: 13
<212> TYPE: PRT
<213> ORGANISM: Artificial sequence
<220> FEATURE:
<223> OTHER INFORMATION: Synthetic peptide

<400> SEQUENCE: 67

Cys Ala Ser Ser Pro Ala Arg Asn Thr Glu Ala Phe Phe
1               5                   10

<210> SEQ ID NO 68
<211> LENGTH: 13
<212> TYPE: PRT
<213> ORGANISM: Artificial sequence
<220> FEATURE:
<223> OTHER INFORMATION: Synthetic peptide

<400> SEQUENCE: 68

Cys Ala Thr Ser Pro Leu Ala Gly Glu Glu Gln Phe Phe
1               5                   10

```
<210> SEQ ID NO 69
<211> LENGTH: 13
<212> TYPE: PRT
<213> ORGANISM: Artificial sequence
<220> FEATURE:
<223> OTHER INFORMATION: Synthetic peptide

<400> SEQUENCE: 69

Cys Ala Arg Ser Phe Arg Ala Gly Arg Asp Gly Thr Phe
1               5                   10

<210> SEQ ID NO 70
<211> LENGTH: 15
<212> TYPE: PRT
<213> ORGANISM: Artificial sequence
<220> FEATURE:
<223> OTHER INFORMATION: Synthetic peptide

<400> SEQUENCE: 70

Cys Ala Ser Ser Gln Trp Thr Gly Pro Pro Tyr Glu Gln Tyr Phe
1               5                   10                  15

<210> SEQ ID NO 71
<211> LENGTH: 16
<212> TYPE: PRT
<213> ORGANISM: Artificial sequence
<220> FEATURE:
<223> OTHER INFORMATION: Synthetic peptide

<400> SEQUENCE: 71

Cys Ala Ser Arg Leu Gly Ser Gly Gly Gly Asn Tyr Gly Tyr Thr Phe
1               5                   10                  15

<210> SEQ ID NO 72
<211> LENGTH: 14
<212> TYPE: PRT
<213> ORGANISM: Artificial sequence
<220> FEATURE:
<223> OTHER INFORMATION: Synthetic peptide

<400> SEQUENCE: 72

Cys Ala Ser Ser Ser Ala Gly Ser Asn Gln Pro Gln His Phe
1               5                   10
```